US010839669B2

(12) United States Patent
Edwards et al.

(10) Patent No.: US 10,839,669 B2
(45) Date of Patent: Nov. 17, 2020

(54) DEVICES, SYSTEMS AND METHODS FOR LOCATING AND INTERACTING WITH MEDICAMENT DELIVERY SYSTEMS

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US); Vaishali Vilas Kamat, Arlington, MA (US); Steven David Gardner, Yaxley Peterborough (GB); Robert George Milner, Hilton (GB)

(73) Assignee: kaleo, Inc., Richmond, VA (US)

( * ) Notice: Subject to any disclaimer, the term of this patent is extended or adjusted under 35 U.S.C. 154(b) by 420 days.

(21) Appl. No.: 15/884,769

(22) Filed: Jan. 31, 2018

(65) Prior Publication Data

US 2018/0151053 A1 May 31, 2018

Related U.S. Application Data

(63) Continuation of application No. 14/142,287, filed on Dec. 27, 2013, now Pat. No. 9,911,308.
(Continued)

(51) Int. Cl.
*A61M 5/20* (2006.01)
*A61M 5/315* (2006.01)
(Continued)

(52) U.S. Cl.
CPC .............. *G08B 21/185* (2013.01); *A61M 5/20* (2013.01); *A61M 5/2053* (2013.01); *A61M 5/31* (2013.01);
(Continued)

(58) Field of Classification Search
CPC ... G08B 21/185; A61M 15/0001; A61M 5/20; A61M 5/2053; A61M 5/31;
(Continued)

(56) References Cited

U.S. PATENT DOCUMENTS

| 2,960,087 A | 11/1960 | Uytenbogaart |
| 3,055,362 A | 11/1960 | Uytenbogaart |

(Continued)

FOREIGN PATENT DOCUMENTS

| AU | 2004231230 | 6/2006 |
| EP | 1287840 A1 | 3/2003 |

(Continued)

OTHER PUBLICATIONS

Office Action for United Kingdom Patent Application No. 1511913.4, dated Sep. 11, 2018.
(Continued)

*Primary Examiner* — Phillip A Gray

(57) ABSTRACT

In some embodiments, a method includes producing, from an adapter, a first wireless signal characterized by a first communication mode with a computing device when a portion of at least one of a medicament delivery device or a simulated medicament delivery is disposed within the adapter. An indication is received when the portion of the medicament delivery device or the simulated medicament delivery device is removed from the adapter. A second wireless signal characterized by a second communication mode with the computing device is produced in response to the indication. The second communication mode is different from the first communication mode. The second communication mode can be, for example, a hold mode, a sniff mode or a park mode.

20 Claims, 47 Drawing Sheets

Related U.S. Application Data

(60) Provisional application No. 61/746,308, filed on Dec. 27, 2012.

(51) Int. Cl.

| | | |
|---|---|---|
| *A61M 15/08* | (2006.01) | |
| *G08B 21/18* | (2006.01) | |
| *H04W 4/80* | (2018.01) | |
| *A61M 5/31* | (2006.01) | |
| *G09B 9/00* | (2006.01) | |
| *H04B 1/3827* | (2015.01) | |
| *A61M 15/00* | (2006.01) | |
| *G16H 20/17* | (2018.01) | |
| *A61M 5/32* | (2006.01) | |
| *A61M 5/50* | (2006.01) | |
| *A61M 11/00* | (2006.01) | |

(52) U.S. Cl.
CPC .......... *A61M 5/3157* (2013.01); *A61M 15/00* (2013.01); *A61M 15/0001* (2014.02); *A61M 15/08* (2013.01); *G09B 9/00* (2013.01); *G16H 20/17* (2018.01); *H04B 1/3827* (2013.01); *H04W 4/80* (2018.02); *A61M 5/3202* (2013.01); *A61M 5/5086* (2013.01); *A61M 11/007* (2014.02); *A61M 2005/206* (2013.01); *A61M 2005/2073* (2013.01); *A61M 2205/14* (2013.01); *A61M 2205/18* (2013.01); *A61M 2205/3306* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/43* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/8206* (2013.01); *A61M 2205/8212* (2013.01); *A61M 2230/04* (2013.01); *A61M 2230/20* (2013.01); *A61M 2230/201* (2013.01); *A61M 2230/42* (2013.01); *Y02A 90/10* (2018.01)

(58) Field of Classification Search
CPC .... A61M 5/3157; A61M 15/00; A61M 15/08; G16H 20/17; H04W 4/80
USPC ....................................................... 604/187
See application file for complete search history.

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,945,379 A | 3/1976 | Pritz et al. |
| 4,108,177 A | 8/1978 | Pistor |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,524,243 A | 6/1985 | Shapiro |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,625 A | 12/1992 | Jacobsen et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,318,533 A * | 6/1994 | Adams ............ A61M 25/10182 128/903 |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,544,647 A | 8/1996 | Jewett et al. |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,610,992 A | 3/1997 | Hickman |
| 5,615,771 A | 4/1997 | Hollister |
| 5,616,132 A | 4/1997 | Newman |
| 5,642,731 A | 7/1997 | Kehr |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,740,794 A | 4/1998 | Smith et al. |
| 5,752,235 A | 5/1998 | Kehr et al. |

(56) References Cited

U.S. PATENT DOCUMENTS

| | | |
|---|---|---|
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,820,602 A | 10/1998 | Kovelman |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,905,653 A | 5/1999 | Higham et al. |
| 5,925,021 A | 7/1999 | Castellano et al. |
| 5,928,195 A | 7/1999 | Malamud et al. |
| 5,941,857 A | 8/1999 | Nguyen et al. |
| 5,954,641 A | 9/1999 | Kehr et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,002,781 A | 12/1999 | Takayama et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,144,310 A | 11/2000 | Morris |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,297,737 B1 | 10/2001 | Irvin |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 | 3/2003 | Wan et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,509 B1 | 5/2003 | Plante et al. |
| 6,569,123 B2 | 5/2003 | Alchas et al. |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,589,229 B1 | 7/2003 | Connelly et al. |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,923,764 B2 | 8/2005 | Aceti et al. |

(56) References Cited

U.S. PATENT DOCUMENTS

| | | |
|---|---|---|
| 6,936,029 B2 | 8/2005 | Mann et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,048,141 B2 | 5/2006 | Abdulhay |
| 7,072,738 B2 | 7/2006 | Bonney et al. |
| 7,074,211 B1 | 7/2006 | Heiniger et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,630,788 B1 | 12/2009 | Reese |
| 7,635,348 B2 | 12/2009 | Raven et al. |
| 7,648,482 B2 | 1/2010 | Edwards et al. |
| 7,648,483 B2 | 1/2010 | Edwards et al. |
| 7,657,849 B2 | 2/2010 | Chaudhri et al. |
| 7,670,328 B2 | 3/2010 | Miller et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,875,022 B2 | 1/2011 | Wenger et al. |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,206,360 B2 | 6/2012 | Edwards et al. |
| 8,212,658 B2 | 7/2012 | Monroe |
| 8,226,610 B2 | 7/2012 | Edwards et al. |
| 8,229,392 B2 | 7/2012 | Burniller et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,627,816 B2 | 1/2014 | Edwards et al. |
| 8,639,288 B1 | 1/2014 | Friedman |
| 8,670,865 B2 | 3/2014 | Coe |
| 8,690,827 B2 | 4/2014 | Edwards et al. |
| 8,789,748 B2 | 7/2014 | Waugh et al. |
| 8,807,131 B1 | 8/2014 | Tunnell et al. |
| 8,849,449 B2 | 9/2014 | Waugh et al. |
| 8,910,299 B2 | 12/2014 | Michalske |
| 8,922,367 B2 | 12/2014 | Denny et al. |
| 8,926,594 B2 | 1/2015 | Edwards et al. |
| 8,939,943 B2 | 1/2015 | Edwards et al. |
| 9,022,980 B2 | 5/2015 | Edwards et al. |
| 9,035,765 B2 | 5/2015 | Engelhard et al. |
| 9,053,530 B2 | 6/2015 | Vik et al. |
| 9,084,849 B2 | 7/2015 | Edwards et al. |
| 9,173,999 B2 | 11/2015 | Edwards et al. |
| 9,179,260 B2 | 11/2015 | Ostrander et al. |
| 9,327,077 B2 | 5/2016 | Edwards et al. |
| 9,542,826 B2 | 1/2017 | Edwards et al. |
| 9,566,395 B2 | 2/2017 | Denny et al. |
| 9,643,770 B2 | 5/2017 | Denny et al. |
| 2001/0005781 A1 | 6/2001 | Bergens et al. |
| 2002/0000225 A1 | 1/2002 | Schuler et al. |
| 2002/0016567 A1 | 2/2002 | Hochman et al. |
| 2002/0042596 A1 | 4/2002 | Hartlaub et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0065536 A1 | 4/2003 | Hansen et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0171717 A1 | 9/2003 | Farrugia et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0042596 A1 | 3/2004 | Kim et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0084047 A1 | 5/2004 | Hickle |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0147818 A1 | 7/2004 | Levy et al. |
| 2004/0159364 A1 | 8/2004 | Landau et al. |
| 2004/0210199 A1 | 10/2004 | Atterbury et al. |
| 2004/0215369 A1 | 10/2004 | Rosenbium |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0190941 A1 | 9/2005 | Yang |
| 2005/0192530 A1 | 9/2005 | Castellano |
| 2005/0197654 A1 | 9/2005 | Edman et al. |
| 2005/0209558 A1 | 9/2005 | Marx |
| 2005/0209569 A1 | 9/2005 | Ishikawa et al. |
| 2005/0261742 A1 | 11/2005 | Nova et al. |
| 2005/0267403 A1 | 12/2005 | Landau et al. |

(56) References Cited

U.S. PATENT DOCUMENTS

| | | |
|---|---|---|
| 2005/0273059 A1 | 12/2005 | Mernoe et al. |
| 2005/0277891 A1 | 12/2005 | Sibbitt |
| 2006/0022806 A1 | 2/2006 | Auerbach |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0169611 A1 | 8/2006 | Prindle |
| 2006/0169773 A1 | 8/2006 | Lyons et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguedas et al. |
| 2006/0247579 A1 | 11/2006 | Friedman |
| 2006/0265186 A1 | 11/2006 | Holland et al. |
| 2006/0281435 A1 | 12/2006 | Shearer et al. |
| 2007/0008113 A1 | 1/2007 | Spoonhower et al. |
| 2007/0074722 A1 | 4/2007 | Giroux et al. |
| 2007/0111175 A1 | 5/2007 | Raven et al. |
| 2007/0149954 A1 | 6/2007 | Hood et al. |
| 2007/0184847 A1 | 8/2007 | Hansen et al. |
| 2007/0186923 A1 | 8/2007 | Poutiatine et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Checheiski et al. |
| 2007/0260210 A1 | 11/2007 | Conroy |
| 2007/0285238 A1 | 12/2007 | Batra |
| 2007/0285258 A1 | 12/2007 | Hartman |
| 2008/0021521 A1* | 1/2008 | Shah ............... A61N 1/37229 607/60 |
| 2008/0059133 A1* | 3/2008 | Edwards ............. A61M 15/009 703/7 |
| 2008/0097311 A1 | 4/2008 | Dacquay et al. |
| 2008/0111685 A1 | 5/2008 | Olson et al. |
| 2008/0140018 A1 | 6/2008 | Enggaard et al. |
| 2008/0160492 A1 | 7/2008 | Campbell et al. |
| 2008/0228143 A1 | 9/2008 | Stamp |
| 2008/0230057 A1 | 9/2008 | Sutherland |
| 2008/0234625 A1 | 9/2008 | Dacquay et al. |
| 2009/0030285 A1 | 1/2009 | Andersen |
| 2009/0062728 A1 | 3/2009 | Woo |
| 2009/0069787 A1 | 3/2009 | Estes et al. |
| 2009/0131875 A1 | 5/2009 | Green |
| 2009/0143761 A1 | 6/2009 | Cantor et al. |
| 2009/0194104 A1 | 8/2009 | Van Sickle |
| 2009/0299156 A1 | 12/2009 | Simpson et al. |
| 2010/0060464 A1 | 3/2010 | Larsen |
| 2010/0111066 A1 | 5/2010 | Mehta |
| 2010/0169111 A1 | 7/2010 | Brue et al. |
| 2010/0192948 A1 | 8/2010 | Sutherland et al. |
| 2010/0208146 A1 | 8/2010 | Reams |
| 2010/0211005 A1 | 8/2010 | Edwards et al. |
| 2010/0214095 A1 | 8/2010 | Davide |
| 2010/0250280 A1 | 9/2010 | Sutherland |
| 2010/0250697 A1 | 9/2010 | Hansen et al. |
| 2010/0267357 A1 | 10/2010 | Holmstrom et al. |
| 2010/0268303 A1 | 10/2010 | Mitchell et al. |
| 2010/0286612 A1 | 11/2010 | Cirillo |
| 2011/0046698 A1 | 2/2011 | Kivi et al. |
| 2011/0144574 A1 | 6/2011 | Kamen et al. |
| 2011/0264033 A1 | 10/2011 | Jensen et al. |
| 2011/0295215 A1 | 12/2011 | Nielsen et al. |
| 2012/0015335 A1 | 1/2012 | Smith et al. |
| 2012/0046613 A1 | 2/2012 | Plumptre |
| 2012/0052837 A1 | 3/2012 | Reich et al. |
| 2012/0071819 A1 | 3/2012 | Bruggemann et al. |
| 2012/0081225 A1 | 4/2012 | Waugh et al. |
| 2012/0083666 A1 | 4/2012 | Waugh et al. |
| 2012/0101444 A1 | 4/2012 | Muller-Pathle et al. |
| 2012/0107783 A1 | 5/2012 | Julian et al. |
| 2012/0165747 A1 | 6/2012 | Lenin et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0072897 A1 | 3/2013 | Day et al. |
| 2013/0079708 A1 | 3/2013 | Wimpenny et al. |
| 2013/0079725 A1 | 3/2013 | Shang et al. |
| 2013/0110050 A1 | 5/2013 | Boyd et al. |
| 2013/0131601 A1 | 5/2013 | Pommereau et al. |
| 2013/0138040 A1 | 5/2013 | Weinandy |
| 2013/0138444 A1 | 5/2013 | George |
| 2013/0151162 A1 | 6/2013 | Harris et al. |
| 2013/0236872 A1 | 9/2013 | Laurusonis et al. |
| 2013/0266919 A1 | 10/2013 | Baker et al. |
| 2014/0004808 A1 | 1/2014 | Li et al. |
| 2014/0082501 A1 | 3/2014 | Bae et al. |
| 2014/0155827 A1 | 6/2014 | Ostrander et al. |
| 2014/0207099 A1 | 7/2014 | Nagar |
| 2014/0243749 A1 | 8/2014 | Edwards et al. |
| 2014/0257241 A1 | 9/2014 | Sutkin et al. |
| 2014/0276385 A1 | 9/2014 | Baker et al. |
| 2014/0296824 A1 | 10/2014 | Edwards et al. |
| 2014/0354998 A1 | 12/2014 | Bock et al. |
| 2014/0371714 A1 | 12/2014 | Edwards et al. |
| 2014/0379874 A1 | 12/2014 | Starr et al. |
| 2015/0045729 A1 | 2/2015 | Denzer et al. |
| 2015/0051538 A1 | 2/2015 | Hata et al. |
| 2015/0112707 A1 | 4/2015 | Manice et al. |
| 2015/0196711 A1 | 7/2015 | Edwards et al. |
| 2015/0202367 A1 | 7/2015 | Plaschkes et al. |
| 2015/0208981 A1 | 7/2015 | Oh et al. |
| 2016/0121056 A1 | 5/2016 | Edwards et al. |
| 2016/0129182 A1 | 5/2016 | Schuster et al. |
| 2016/0157816 A1 | 6/2016 | Denny |
| 2016/0166768 A1 | 6/2016 | Edwards et al. |
| 2016/0184535 A1 | 6/2016 | Edwards et al. |
| 2016/0235916 A1 | 8/2016 | Edwards et al. |
| 2016/0256639 A1 | 9/2016 | Van Sickle et al. |
| 2016/0296716 A1 | 10/2016 | Cabiri et al. |
| 2016/0342748 A1 | 11/2016 | Gulfo et al. |
| 2017/0049954 A1 | 2/2017 | Edwards et al. |
| 2017/0068799 A1 | 3/2017 | Mesinger et al. |
| 2017/0092101 A1 | 3/2017 | Edwards et al. |
| 2017/0109498 A1 | 4/2017 | Childress et al. |
| 2018/0033286 A1 | 2/2018 | Edwards et al. |
| 2018/0158374 A1 | 6/2018 | Zamierowski et al. |
| 2018/0204636 A1 | 7/2018 | Edwards et al. |
| 2019/0030247 A1 | 1/2019 | Edwards et al. |
| 2019/0030265 A1 | 1/2019 | Edwards et al. |
| 2019/0139453 A1 | 5/2019 | Edwards et al. |
| 2019/0151548 A1 | 5/2019 | Edwards et al. |
| 2019/0206220 A1 | 7/2019 | Edwards et al. |
| 2019/0217004 A1 | 7/2019 | Edwards et al. |
| 2019/0279756 A1 | 9/2019 | Edwards et al. |
| 2019/0358399 A1 | 11/2019 | Edwards et al. |

FOREIGN PATENT DOCUMENTS

| | | |
|---|---|---|
| EP | 1712178 A2 | 10/2006 |
| EP | 1095668 | 4/2007 |
| EP | 1777984 A1 | 4/2007 |
| EP | 1883268 A2 | 1/2008 |
| WO | WO 93/02720 | 2/1993 |
| WO | WO 95/26009 | 9/1995 |
| WO | WO 96/25965 | 8/1996 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 2001/003758 | 1/2001 |
| WO | WO 2001/024690 | 4/2001 |
| WO | WO 2001/026020 | 4/2001 |
| WO | WO 2001/088828 | 11/2001 |
| WO | WO 2001/093926 | 12/2001 |
| WO | WO 2002/100469 | 12/2002 |
| WO | WO 2003/095001 | 11/2003 |

(56) References Cited

FOREIGN PATENT DOCUMENTS

| WO | WO 2004/022138 | 3/2004 |
|---|---|---|
| WO | WO 2005/050526 | 6/2005 |
| WO | WO 2005/074790 | 8/2005 |
| WO | WO 2006/045525 | 5/2006 |
| WO | WO 2006/109778 | 10/2006 |
| WO | WO 2006/123956 | 11/2006 |
| WO | WO 2006/125692 | 11/2006 |
| WO | WO 2007/087304 | 8/2007 |
| WO | WO 2008/005315 | 1/2008 |
| WO | WO 2008/008451 | 1/2008 |
| WO | WO 2008/148864 | 12/2008 |
| WO | WO 2010/114392 | 10/2010 |
| WO | WO 2012/063172 | 5/2012 |
| WO | WO 2012/164402 A2 | 12/2012 |
| WO | WO 2013/033467 A1 | 3/2013 |
| WO | WO 2013/043063 | 3/2013 |
| WO | WO 2013/154954 | 10/2013 |
| WO | WO 2013/164628 A1 | 11/2013 |
| WO | 2014/008393 A1 | 1/2014 |
| WO | WO 2014/036308 A2 | 3/2014 |
| WO | WO 2014/089083 A1 | 6/2014 |
| WO | WO 2014/116987 A1 | 7/2014 |
| WO | WO 2014/143815 A2 | 9/2014 |
| WO | WO 2014/144096 A1 | 9/2014 |
| WO | WO 2015/044102 A1 | 4/2015 |
| WO | WO 2015/044112 A1 | 4/2015 |

OTHER PUBLICATIONS

Office Action for Australian Patent Application No. 2017258859, dated Oct. 16, 2018.
"Solutions for Medical Devices," 3M Brochure, © 3M, (2006), 80-6201-3490-0, 8 pages.
Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.
"Flexible circuits / Flex circuits / Flexible Technology Ltd.," Flexible Technology Limited [online] [retrieved on Aug. 28, 2006] Retrieved from the Internet <URL: http://www/flexibletechnology.com/ >, 2 pages.
"Flexible circuits capabilities of Flexible Technology Limited," Our Flexible Circuits Capabilities [online] [retrieved on Aug. 28, 2006] Retrieved from the Internet <URL: http://www/flexibletechnology.com/Flexible circuitsCapability.htm >, 2 pages.
"Flex Circuits/flexible circuits design guide," [retrieved on Aug. 28, 2006] Retrieved from the Internet <URL: http://flexiblecircuit.co.uk/Flex Circuits Design Guide.htm >, 7 pages.
"Insect Stings Auto-Injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.
"Anaphylaxis Canada Product Catalogue, "Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.
Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.
RFID Gazette, "Smart Labels in Healthcare," Sep. 29, 2005 [online] [retrieved on Nov. 28, 2006] Retrieved from the Internet <URL: http://www.rfidgazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.
Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.
Heartsine Technology, samaritan™ Pad Accessories [online] [retrieved on Jun. 1, 2007] Retrieved from the Internet <URL: http://wm.heartsine.com/aboutsam-accesscries.htm>, 4 pages.
CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.
AED Professionals™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-.
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.
Gosbee, L. L., "Nuts! I Can't Figure Out How to Use My Life-Saving Epinephrine Auto-Injector," Joint Commision Journal on Quality and Safety, 30(4):220-223 (Apr. 2004).
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.
Apple, Inc., "Bluetooth Accessory Design Guidelines for Apple Products," Release R7, (Sep. 18, 2013), 40 pages.
Stuart, M., "Cellnovo's Mobile Health Approach to Diabetes Care," In Vivo: The Business & Medicine Report, (Dec. 2010), pp. 40-44.
International Search Report and Written Opinion for International Patent Application No. PCT/US2008/051612, dated Dec. 9, 2008, 7 pp.
Office Action for U.S. Appl. No. 13/550,999, dated Apr. 18, 2014, 17 pages.
International Search Report and Written Opinion for International Patent Application No. PCT/US2013/078071, dated May 6, 2014, 19 pages.
International Preliminary Report on Patentability for International Patent Application No. PCT/US2013/077996, mailed Jun. 30, 2015.
Search Report for European Patent Application No. 13868849.4, dated Aug. 5, 2016
Search Report for European Patent Application No. 13867489.0, dated Jan. 4, 2017
Office Action for U.S. Appl. No. 14/142,287, dated Apr. 6, 2017.
Office Action for Australia Patent Application No. 2015249064, dated Aug. 25, 2017.
Anonymous: "Bluetooth—Wikipedia, the free encyclopedia", Oct. 11, 2012 (Oct. 11, 2012), XP055295137, Retrieved from the Internet: URL: https://en.wikipedia.org/w/index.php?title=Bluetooth&oldid=517244384 [retrieved on Aug. 11, 2016].
Anonymous: "Emergency Call Button on Lock Screen—Apple Community", May 14, 2011 (May 14, 2011), XP055494181, Retrieved from the Internet: URL: https://discussions.apple.com/thread/2783061 [retrieved on Jul. 20, 2018].
Office Action for Australian Patent Application No. 2017258859, dated Jul. 16, 2019.
Office Action for Australian Patent Application No. 2017258859, dated Sep. 26, 2019.

* cited by examiner

DEVICES, SYSTEMS AND METHODS FOR LOCATING AND INTERACTING WITH MEDICAMENT DELIVERY SYSTEMS

CROSS-REFERENCE TO RELATED APPLICATIONS

This application is a continuation of U.S. patent application Ser. No. 14/142,287, entitled "Devices, Systems and Methods for Locating and Interacting with Medicament Delivery Systems," filed Dec. 27, 2013, which claims priority to U.S. Provisional Application No. 61/746,308, entitled "Devices, Systems and Methods for Locating and Interacting with Medicament Delivery Systems," filed Dec. 27, 2012, both of which are incorporated herein by reference in their entirety.

BACKGROUND

The embodiments described herein relate generally to a medical device, and more particularly to a medicament delivery device, and/or a simulated medicament delivery device having and/or associated with a wireless communication module. The embodiments described herein also relate to devices for interacting with and/or monitoring (e.g., wirelessly) with such medicament delivery devices and/or simulated medicament delivery devices via the wireless communication module.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

As another example, naloxone is a medicament that prevents and/or reverses the effects of opioids. Known formulations of naloxone can be used, for example, to treat respiratory depression and other indications that result from opioid toxicity. For example, known formulations for naloxone can be used to reverse and/or mitigate the effects of an overdose of a drug containing opioids, such as, for example, prescription opioids like oxycodone or illicit opioids like heroin. In such situations, it is desirable to deliver the naloxone formulation quickly and in a manner that will produce a rapid onset of action. Known methods for delivering naloxone intranasally or via injection, however, often involve completing a series of operations that, if not done properly, can limit the effectiveness of the naloxone formulation. Moreover, because naloxone is often administered during an emergency situation, even experienced and/or trained users may be subject to confusion and/or panic, thereby compromising the delivery of the naloxone formulation.

As yet another example, glucagon is a medicament that is administered to treat patients suffering from hypoglycemia. In certain situations, the onset of hypoglycemia can cause the patient to lose motor coordination and/or lose consciousness. Thus, glucagon is often administered by a care giver during an emergency situation.

In the above-identified examples, the individual requiring the medicament may be inexperienced and/or may infrequently require medical intervention (e.g., in the case of a naloxone delivery device), and thus may be forget to carry the medicament delivery device and/or forget how to use the delivery device. For example, to actuate some known auto-injectors, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. If the medicament delivery device is not available or if the individual is unable to properly operate the medicament delivery device, important medical aid may not be properly delivered.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, or primary care-giver, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic, and/or the physiological effects of the condition requiring treatment.

Additionally or alternatively, the individual requiring the medicament may be incapacitated and unable to inform bystanders of the nature of the medical emergency, that a medicament delivery device is available, and/or how to use the medicament delivery device. If bystanders remain unaware of the availability and location of the medicament delivery device, or are unable to administer the medicament, important medical aid may not be delivered. To enhance the likelihood of proper use, some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, nasal delivery systems, wearable injectors or bolus pumps, transdermal delivery systems, inhalers or the like, can be compact, such printed instructions may be too small to read and comprehend during a situation requiring the need for immediate and accurate administration.

Furthermore, some known medicament delivery devices, such as, for example, auto-injectors, pen injectors, inhalers, and/or simulated medicament delivery devices are configured to be carried with the user. Although such devices may improve the likelihood of compliance, such portable devices can exacerbate the shortcomings described above (e.g., inadequate instructions for use). Additionally, because such portable devices are small, there is an increased likelihood that such devices will be forgotten and/or misplaced. Moreover, the cost and size constraints of known devices prevents the inclusion of more detailed features to address the shortcomings described herein. As one example, such portable medicament delivery devices may have limited space for electronics. For example, unlike stationary devices, such as infusion pumps and the like, compact medicament delivery devices may have insufficient space for full-scale computational devices, such as general purpose processors, large form-factor printed circuit boards, and the like.

In addition to the issues relating to improper use of medicament delivery devices, monitoring the patient's compliance with known medicament delivery devices can also be problematic. For example, some known treatment regimens include multiple doses of a medicament that must be administered in a timely fashion and/or in a particular order to ensure effectiveness (e.g., certain vaccination regimens). Thus, monitoring the patient's compliance is an important aspect in ensuring that the treatment method will be effective. Some known medicament delivery systems include a medicament delivery device and an accompanying electronic system to assist the user in setting the proper dosage and/or maintaining a compliance log. Such known medicament delivery systems and the accompanying electronic systems can be large and therefore not conveniently carried by the user. Such known medicament delivery systems and the accompanying electronic systems can also be complicated to use and/or expensive to manufacture.

In addition, an extended shelf life may be desirable for some medicament delivery devices, such as devices intended to be carried by a user on a daily basis. For example, an auto-injector intended to be carried by a user on a daily basis may be expected to work after weeks, months, or years without user maintenance. As another example, known emergency-use auto-injectors are single-use devices that are expected to be carried for years before a potential use. The disposable nature and/or extended shelf-life of such devices can further exacerbate the shortcomings described above. For example, the electronics of known stationary devices, particularly known devices having electronic communication means (e.g., for compliance tracking), may not be efficient enough to provide sufficiently long battery life for use in a portable, extended shelf life device. Furthermore, efficient power management may be desirable to extend the useful life of a medicament delivery device, particularly for a device having limited battery capacity, limited or no user replaceable batteries, and/or limited or no charging capacity.

As another way to enhance the likelihood of proper use, some known medicament delivery devices are associated with simulated medicament delivery devices (e.g., "trainers") to provide a method for users to practice using the medicament delivery device without being exposed to the medicament and/or needles typically contained therein. Such simulated medicament delivery devices, however, can also include inadequate use instructions as described above.

Thus, a need exists for medicament delivery systems and/or devices that allow a medicament delivery device to be quickly identified and located, alert the user if the medicament delivery device is forgotten, and provide instructions that can be easily understood by a user in any type of situation. Additionally, a need exists for simulated medicament delivery systems and/or devices that can provide instructions and that can be reused multiple times. Moreover, a need exists for medicament delivery systems and/or devices that can provide compliance information associated with the use of the device and/or that can communicate electronically with other communications devices.

SUMMARY

System and methods to facilitate wireless communications with medicament delivery devices and simulated medicament delivery devices are described herein. In some embodiments, a method includes producing, from an adapter, a first wireless signal characterized by a first communication mode with a computing device when a portion of at least one of a medicament delivery device or a simulated medicament delivery is disposed within the adapter. An indication is received when the portion of the medicament delivery device or the simulated medicament delivery device is removed from the adapter. A second wireless signal characterized by a second communication mode with the computing device is produced in response to the indication. The second communication mode is different from the first communication mode. The second communication mode can be, for example, a hold mode, a sniff mode or a park mode.

DETAILED DESCRIPTION

Figure 1:
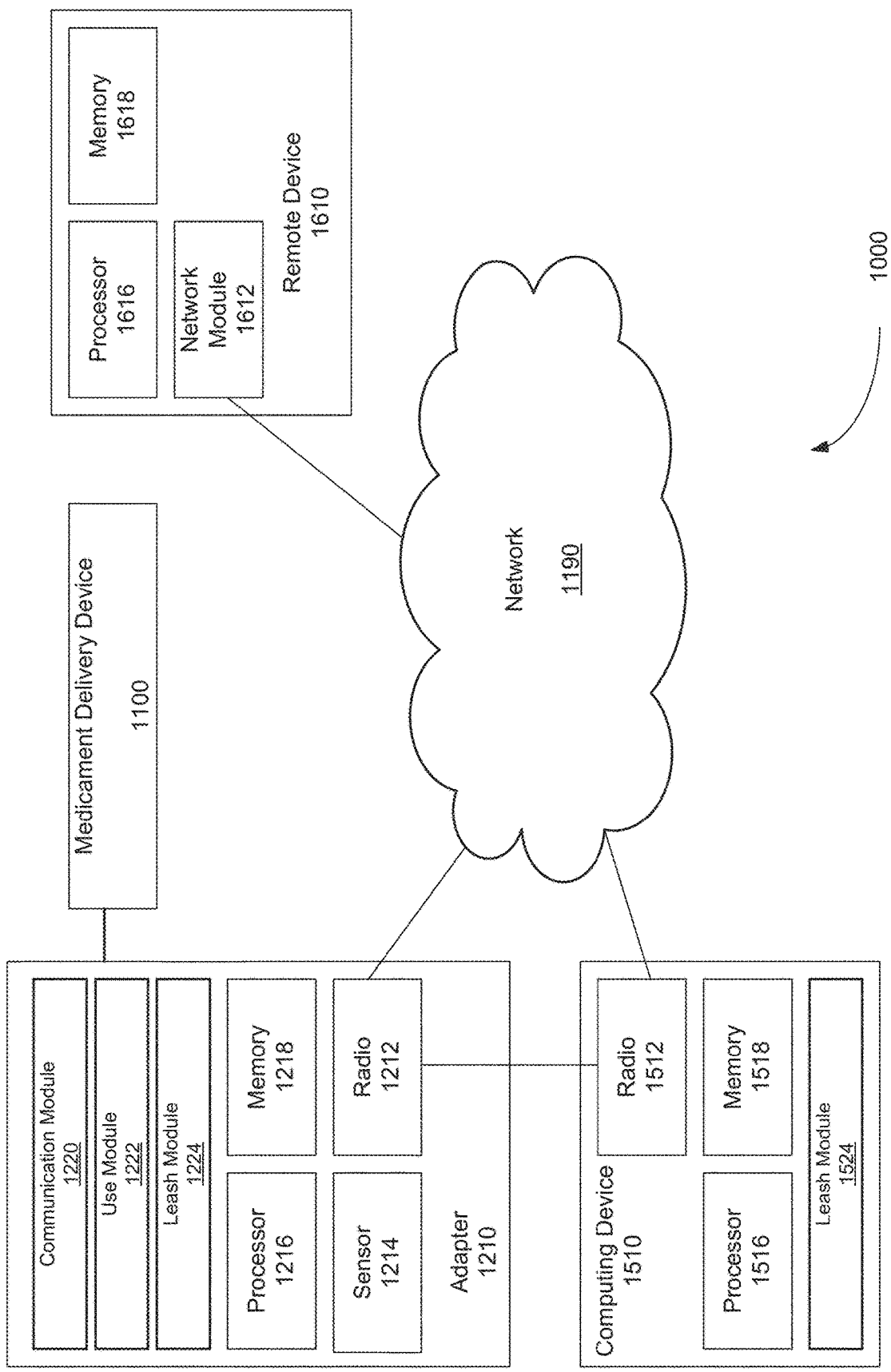
FIG. 1 is a schematic illustration of medicament delivery system according to an embodiment of the invention.

This application describes devices that are related to and/or can be used with the devices and systems described in U.S. Pat. No. 8,172,082, entitled "Devices Systems and Methods for Medicament Delivery," filed Feb. 5, 2007, U.S. Pat. No. 8,231,573, entitled "Medicament Delivery Device Having an Electronic Circuit System," filed May 12, 2008, and U.S. Pat. No. 8,361,026, entitled "Apparatus and Methods for Self-Administration of Vaccines and Other Medicaments," filed Nov. 10, 2009, each of which is incorporated herein by reference in its entirety.

The medicament delivery systems shown and described herein can be used in conjunction with any suitable medicament delivery device and/or medicament container such that the medicament delivery device and/or medicament container can be easily accessed, identified and located, as described herein. In some embodiments, the medicament delivery device can be a medical injector, such as a pen injector, a prefilled syringe, an auto-injector, nasal delivery device or the like.

In some embodiments, an apparatus includes a medicament delivery device and an electronic circuit system. The electronic circuit system includes a radio such that the apparatus can be electronically linked to a computing device using a wireless protocol. The medicament delivery device can have a first configuration and a second configuration. The radio can send a signal characterized by a first communication interval when the medicament delivery device is in the first configuration. The radio can send a signal characterized by a second, different, communication interval when the medicament delivery device is in the second configuration.

In some embodiments, a method includes producing a first wireless signal characterized by a first communication interval when a medicament delivery device is in a first configuration. An indication can be received indicating that the medicament delivery device has transitioned from the first configuration to a second configuration. A second wireless signal, characterized by a second, different, communication interval can be sent in response to receiving the indication that the medicament delivery device has transitioned from the first configuration to a second configuration. In some embodiments, the first communication interval is associated with a first communication mode, and the second communication interval is associated with a second communication mode. The first communication mode and/or the second communication mode can be an advertising mode, a hold mode, a sniff mode or a park mode.

In some embodiments, a non-transitory processor-readable medium includes code to cause a processor of a device to produce a first wireless signal characterized by a first communication interval when a medicament delivery device is in a first configuration. The non-transitory processor-readable medium includes code to receive an indication that the medicament delivery device has transitioned from the first configuration to a second configuration. The code (executed on a processor) can cause the device to produce a second wireless signal, characterized by a second, different, communication interval in response to receiving the indication that the medicament delivery device has transitioned.

In some embodiments, an apparatus includes a radio, a memory and a communication module. The radio is configured to electronically communicate with a computing device via a wireless protocol (e.g., Bluetooth®). The radio is configured to send a first wireless signal associated with a first communication interval and a second wireless signal associated with a second communication interval. The memory is configured to store transition information associated with a transition of a medicament delivery device from a first configuration to a second configuration. The communication module, which is implemented in at least one of the memory or a processing device, is configured to receive the transition information and determine, based on the transition information, at least the second communication interval.

In some embodiments, an apparatus includes an adapter configured to receive at least a portion of a medicament delivery device or a simulated medicament delivery device. The apparatus also includes an electronic circuit system having a sensor and a radio. The sensor can detect when the adapter is removed from the medicament delivery device or the simulated medicament delivery device. The radio can electronically communicate with a computing device via a wireless protocol. The radio can send a first signal characterized by a first communication interval when the adapter is coupled to the medicament delivery device or the simulated medicament delivery device, and can send a second signal characterized by a second communication interval when the adapter is not coupled to the medicament delivery device or the simulated medicament delivery device. In some such embodiments, the medicament delivery device or the simulated medicament delivery can include a second electronic circuit system configured to produce an electronic output when the medicament delivery device or the simulated medicament delivery device is actuated. In such embodiments, the adapter can include a protrusion that can isolate the circuit of the medicament delivery device or the simulated medicament delivery device from a battery when the adapter is coupled to the medicament delivery device or a simulated medicament delivery device.

In some embodiments, an apparatus includes an adapter configured to receive at least a portion of a medicament delivery device or a simulated medicament delivery device. The medicament delivery device or the simulated medicament delivery device includes a first electronic circuit system configured to produce an electronic output when the device is actuated. The adapter has a protrusion configured to isolate at least a portion of the first electronic circuit system from a power source when the portion of the at least one of the medicament delivery device or the simulated medicament delivery device is disposed within the adapter. The apparatus further includes a second electronic circuit system coupled to the adapter. The second electronic circuit system includes a radio configured to electronically communicate with a computing device via a wireless protocol. The radio is configured to send a first signal when the portion of the medicament delivery device or the simulated medicament delivery device is within the adapter and a second signal when the portion of the medicament delivery device or the simulated medicament delivery device is spaced apart from the adapter, the second signal different from the first signal.

In some embodiments, a method includes producing, from an adapter, a first wireless signal characterized by a first communication mode with a computing device when a portion of at least one of a medicament delivery device or a simulated medicament delivery is disposed within the adapter. An indication is received when the portion of the medicament delivery device or the simulated medicament delivery device is removed from the adapter. A second wireless signal characterized by a second communication mode with the computing device is produced in response to the indication. The second communication mode is different from the first communication mode. The second communication mode can be, for example, a hold mode, a sniff mode or a park mode.

In some embodiments, a simulated medicament delivery device can produce an indication associated with an operation of the simulated medicament delivery device. In response, a recorded speech output can be generated and information associated with the operation can be stored in a memory. A training script can be updated based on the information stored in the memory.

In some embodiments, a method includes receiving an indication associated with an operation from a set of operations associated with a simulated medicament delivery device. The set of operations can be, for example, a series of operations to be taken when actuating an actual medicament delivery device that corresponds to the simulated device. In response to the indication, a recorded speech output associated with a first training script is produced. Additionally, in response to the indication, use information associated with the plurality of operations associated with a simulated medicament delivery device is updated. The method further includes producing, in response to the updated use information, a second training script.

In some embodiments, a method includes receiving at a first time a wireless signal associated with a slave device. A first location associated with a master device at the first time is determined. An alarm is produced when the wireless signal is not received within a time period after the first time and a second location associated with the master device at a second time is different from the first location by a distance.

The term "about" when used in connection with a referenced numeric indication means the referenced numeric indication plus or minus up to 10% of that referenced numeric indication. For example, "about 100" means from 90 to 110.

FIG. 1 is a schematic illustration of a medicament delivery system 1000 (also referred to herein simply as "the system 1000") according to an embodiment. The system 1000 includes a medicament delivery device 1100, an adapter 1210, a computing device 1510, and a remote device 1610.

The medicament delivery device 1100 can be any of the medicament delivery devices described herein. The medicament delivery device 1100 can be any of the medicament delivery devices described in further detail herein. For example, the medicament delivery device 1100 can be an auto-injector similar to the auto-injector 4000 described below with reference to FIGS. 3-34. In other embodiments, the medicament delivery device can be a pen-injector, a syringe, a nasal delivery device (such a nasal spray device), an inhaler, etc. In yet other embodiments, the device 1100 can be a simulated medicament delivery device (i.e., a device that is devoid of a medicament and/or that can simulate the use of a corresponding actual medicament delivery device).

The adapter 1210 can be a housing, cover, case, and/or any other suitable device operable to be coupled to, receive, and/or detect the medicament delivery device. The adapter 1210 can be any of the covers, housings, kits and/or containers described in further detail herein. The adapter 1210 includes an electronic circuit system coupled thereto. In particular, the adapter 1210 includes a processor 1216, a memory 1218, a sensor 1214, and a radio 1212. The adapter also includes a communication module 1220, a use (or history) module 1222 and a leash module 1224. Although shown as including each of the communication module 1220, the use (or history) module 1222 and the leash module 1224, in other embodiments an adapter need not include all (or any) of these modules. For example, in some embodiments, an adapter includes only a leash module 1224, and is configured to perform the leash method associated therewith, and need not include the use module 122 or the communication module 1220. Alternatively, in other embodiments an adapter includes only the communication module 1220.

Figure 2:
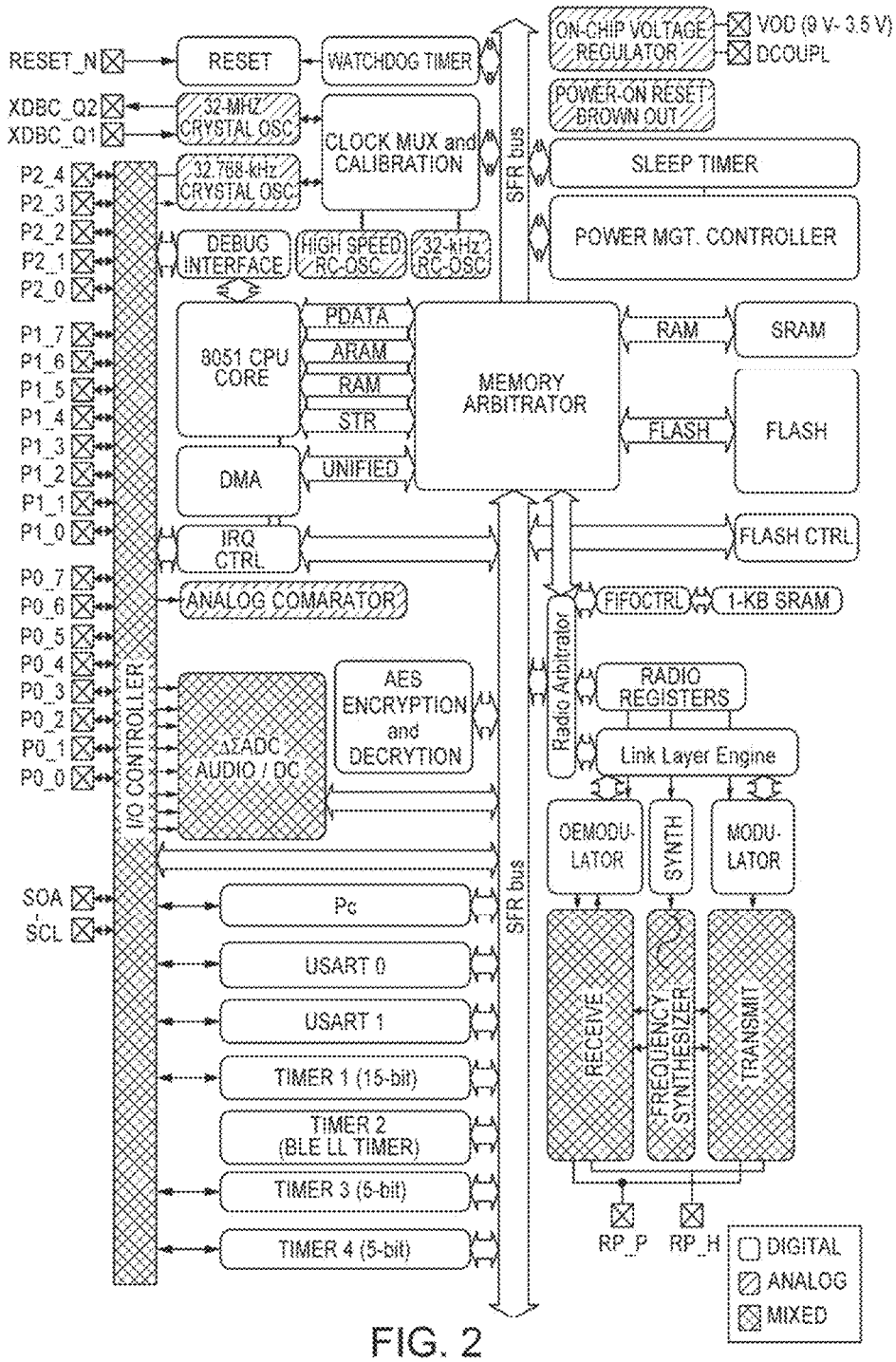
FIG. 2 is a schematic illustration of processor used to perform the methods described, according to an embodiment.

The processor 1216, and any of the processors described herein, can be any suitable processor for performing the methods described herein. In some embodiments, processor 1216 can be configured to run and/or execute application modules, processes and/or functions associated with such a medicament delivery system 1000. For example, the processor 1216 can be configured to run and/or execute the communication module 1220, the use (or history) module 1222 and/or the leash module 1224, and perform the methods associated therewith. The processor 1216 can be, for example, a general purpose processor, a Field Programmable Gate Array (FPGA), an Application Specific Integrated Circuit (ASIC), a Digital Signal Processor (DSP), and/or the like. The processor 1216 can be configured to retrieve data from and/or write data to memory, e.g., the memory 1218. As described herein, in some embodiments, the processor 1216 can cooperatively function with the radio 1212 and/or execute instructions from code to provide signals to communicatively couple the adapter 1210 to the computing device 1510 (e.g., via wireless communication) and/or any other computing entity via a network 1190. In some embodiments, the processor 1216 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. A schematic of a Bluetooth® processor is shown in FIG. 2.

In some embodiments, the processor 1216 can be operable to facilitate any suitable communication mode with the computing device 1510 and/or any other computing entity (e.g., by executing the communication module 1220). Such modes can include, for example, an active mode, hold mode, sniff mode, and/or park mode in accordance with the Bluetooth® wireless protocol. Moreover, the processor 1216 can also be operable to engage in any suitable type of data transfer, such as asynchronous connection-less logical transport (ACL), synchronous connection-oriented link (SCO), and/or any other suitable means.

The memory 1218 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 1218 stores instructions to cause the processor 1216 to execute modules, processes and/or functions associated with such medicament delivery system 1000. For example, the memory 1218 can store instructions to cause the processor 1216 to execute one or more of the communication module 1220, the use module 1222 and/or the leash module 1224, and perform the methods associated therewith.

The sensor 1214 can be a switch, an audible input sensor (e.g., a microphone), optical sensor, and/or any other suitable input device. In some embodiments, the sensor 1214 can be operable to monitor and/or measure the configuration and/or status of the medicament delivery device 1100. The sensor 1214 can be operable to detect if the medicament delivery device 1100 is removed from the adapter 1210, if the medicament delivery device 1100 is actuated, and so forth. For example, the sensor 1214 can include an electrical contact or switch operable to detect (e.g., in conjunction with the processor 1216) when the medicament delivery device 1100 is physically separated from the adapter 1210. As another example, the sensor 1214 can include a microphone operable to detect (e.g., in conjunction with the processor 1216) a mechanical and/or electronic sound associated with the actuation of the medicament delivery device, such as a characteristic hiss of a compressed gas container being discharged and/or a sound emitted from a speaker of the medicament delivery device 1100 (not shown). As yet another example, the sensor 1214 can include an optical sensor operable to detect the configuration of a status window of the medicament delivery device 1100. For example, the sensor 1214 can be operable to detect when a status window of the medicament delivery device 1100 turns color or opaque, which may be associated with use of the medicament delivery device 1100.

The radio 1212 (also referred to as a receiver, transmitter and/or transceiver) can be operable to send signals to, and/or receive radio signals, such as Bluetooth®, ZigBee, WiFi, cellular telephone signals, etc. In some embodiments, such as embodiments where the processor 1216 is Bluetooth® processor, the radio 1212 can be integral with the processor 1216. In other embodiments, the radio 1212 can include a processor distinct from the processor 1216. In some embodiments, the radio 1212 can be operable to communicatively couple (also referred to herein as "linking" or "pairing") the adapter 1210 to the computing device 1510 and/or any other computing entity via a network 1190. The radio 1212 can include or be coupled to a ceramic chip antenna, a stamped antenna, a sintered antenna, a PCB conductive trace antenna, and/or any other suitable antenna.

The communication module 1220 can be a hardware and/or software module (stored in memory 1218 and/or executed in the processor 1216). As described in more detail herein, the communication module 1220 is configured to receive an indication (e.g., from the sensor 1214) and/or transition information associated with a change in status of the medicament delivery device 1100 and determine, based on the indication or the transition information, a connection and/or communications characteristic. Such communication characteristics can include, for example, a communication interval and/or connection interval (e.g., a time period between successive signals or portions of a signal, such an "advertising interval," also referred to herein as a "connection interval"), a communication mode (e.g., a park mode, sniff mode or the like), etc.

The use module 1222 can be a hardware and/or software module (stored in memory 1218 and/or executed in the processor 1216). As described in more detail herein, the use module 1222 is configured to receive an indication (e.g., from the sensor 1214) and/or use information associated with a use or history of the medicament delivery device 1100 and produce a script (e.g., a recorded speech instruction) based thereupon. In this manner, the use module 1222 can facilitate the adapter 1210 and/or the medicament delivery device 1100 (or simulated medicament delivery device) being a "smart" device that can produce updated instructions and/or guidance based on the past history of usage.

The leash module 1224 can be a hardware and/or software module (stored in memory 1218 and/or executed in the processor 1216). As described in more detail herein, the leash module 1224 is configured to receive information associated with the connection (or pairing) between the adapter 1210 and the computing device 1510 and produce an alarm based thereupon. In some embodiments, the leash module 1224 can base the alarms on the position and/or location of the adapter 1210 and/or the computing device 1510.

The network 1190 can be a piconet, the Internet, an intranet, a local area network (LAN), a wide area network (WAN), a virtual network, a telecommunications network, any other suitable communication system and/or combination of such networks. The network 1190 can be implemented as a wired and/or wireless network.

The computing device 1510 can a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), and/or any other suitable computing entity. The computing device 1510 includes a processor 1516, a memory 1518, and a radio 1512.

The processor 1516 can be, for example, a general purpose processor, a FPGA, an ASIC, a DSP, and/or the like. The processor 1516 can be configured to retrieve data from and/or write data to memory, e.g., the memory 1518, which can be, for example, RAM, memory buffers, hard drives, databases, EPROMs, EEPROMs, ROM, flash memory, hard disks, floppy disks, cloud storage, and/or so forth.

The radio 1512 can be structurally and/or functionally similar to the radio 1212. In some embodiments, the radio 1512 can include a processor (e.g., a Bluetooth® processor) distinct from the processor 1516. In some embodiments, a short-range radio link can be established between the computing device 1510 and the adapter 1210. For example, the computing device 1510 and the adapter 1210 can be paired via the Bluetooth® wireless protocol. In such an embodiment, as described in further detail herein, the computing device 1510 can be operable to send and/or receive data from the adapter 1210 related to the medicament delivery device 1100, such as data associated with use, preparation for use, status, and so forth. Furthermore, the adapter 1210 and/or the computing device 1510 can be operable to determine when a short-range communication link is broken (e.g., when the adapter 1210 is out of range of the computing device 1510).

The leash module 1524 can be a hardware and/or software module (stored in memory 1518 and/or executed in the processor 1516). As described in more detail herein, the leash module 1524 is configured to receive information associated with the connection (or pairing) between the adapter 1210 and the computing device 1510 and produce an alarm based thereupon. In some embodiments, the leash module 1524 can base the alarms on the position and/or location of the adapter 1210 and/or the computing device 1510.

In some embodiments, such as an embodiment where the computing device 1510 is a Bluetooth® enabled mobile phone, the radio 1512 can be suitable to establish a short-range radio link with the adapter 1210 and establish a long-range with another computing device (e.g., the remote device 1610) via the network. For example, the radio 1512 can be a dual-function radio and/or the computing device 1510 can include multiple radios to relay information associated with the adapter 1210 (which may be equipped with only a short-range radio) to the remote device 1610 using, for example, a cellular data network and/or a WiFi link to the Internet. In other embodiments, the adapter 1210 may be equipped with a radio operable to communicate with the remote device 1610 via the network 1190.

The computing device 1510 can be operable to store (e.g., in the memory 1218) information associated with the adapter 1210, such as connection time, medicament device 1100 use record, and so forth. In some embodiments, the computing device 1510 can be operable to determine its location (e.g., via a global positioning system (GPS) sensor (not shown)). In such an embodiment, the computing device 1510 can be operable to associate location data with information associated with the adapter 1210, such as use data.

The remote device 1610 can be any suitable computing entity, such as a server or personal computer. The remote device 1616 includes a processor 1616, which can be, for example, a general purpose processor, a FPGA, an ASIC, a DSP, and/or the like. The processor 1616 can be configured to retrieve data from and/or write data to memory, e.g., the memory 1618, which can be, for example, RAM, memory buffers, hard drives, databases, EPROMs, EEPROMs, ROM, flash memory, hard disks, floppy disks, cloud storage, and/or so forth. The network module 1612 can be any suitable module operable to communicatively couple the remote device 1610 to the network 1190. For example, the network module 1612 can be a network interface controller (NIC).

In some embodiments, the remote device 1610 can be operable to receive reports associated with the medicament delivery device 1100 from the adapter 1210 and/or the computing device 1510 via the network 1190. For example, the remote device 1610 can be associated with a healthcare provider and/or emergency contact and used to monitor medicament delivery device 1100 use and/or compliance.

In some embodiments, the processor 1216 of the adapter 1210 and/or the processor 1516 of the computing device 1510 (and any of the processors described herein) can be operable to execute code to implement a wireless communications protocol. For example, the processor 1216 and/or the processor 1516 can execute a Bluetooth® stack (which may be stored in memory 1218, 1518) having service, profile, and/or application layers operable to control and/or improve connectivity, power management, and/or any other suitable feature associated with the Bluetooth® protocol. For example, as described in further detail herein, the processor(s) 1216, 1516, can be operable to alter mode (e.g., from park to sniff, from sniff to active, or any other suitable change), alter communication type (e.g., from ACL communication to SCO communication), alter advertising interval, and/or any other suitable communication parameter. In this manner, in accordance with the methods described herein, the processor 1216 and/or the processor 1516 can alter and/or implement a characteristic of the wireless communication in response to a change associated with the medicament delivery device 1100 (or simulated medicament delivery device). As one example, the processor(s) 1216, 1516 can be operable to alter a communication mode from advertising a connectable status on a first channel (or set of channels) to sending and/or receiving communication packets on a second channel (or set of channels).

As described in further detail herein, in some embodiments, the computing device 1510 can be operable to track the location and/or status of the adapter 1210. For example, by recording when the computing device 1510 is communicatively coupled to the adapter 1210, which may be associated with location information, the computing device 1510 can provide an indication of the last location at which it was linked to the adapter 1210. Furthermore, the computing device 1510 can be operable to use triangulation, homing, and/or any other suitable technique to locate the adapter 1210 when the adapter 1210 is within radio range. In addition or alternatively, the computing device 1510 can send a signal to the adapter 1210 operable to cause the adapter to emit a noise or other signal to aid the user in locating the adapter 1210 (and the medicament delivery device 1000).

In some embodiments, as described in further detail herein, the computing device 1510 and/or the adapter 1210 can include a leash functionality (e.g., implemented in the leash module 1224 and/or the leash module 1524) such that when the communications between the computing device 1510 and the adapter 1210 is disrupted (e.g., the communication device 1510 moves out of range and/or vice versa), the adapter 1210 and/or the communication device 1510 can generate an alert to notify a user that a link has been lost. For example, an individual may be advised to carry a medicament delivery device, such as an epinephrine auto-injector, but may rarely use the medicament delivery device. As a result, the user may occasionally forget to carry the medicament delivery device, which can have serious consequences in the event of a medical emergency. If the user additionally carries the computing device 1510, and is less likely to forget the computing device 1510 (for example, where the computing device 1510 is a mobile phone that the user uses on a regular basis), a leash function can alert the user if the medicament delivery device 1100 is forgotten. In some embodiments, the computing device 1510 and/or the adapter 1210 can generate an alert any time the computing device 1510 is moved out of range of the adapter 1210 (i.e., indicating that the adapter 1210 is not being carried together with the computing device 1510). In another embodiment, the computing device 1510 can be operable to verify its location (e.g. via GPS) and alert if the computing device 1510 is out of range of the adapter 1210 and the computing device 1510 has moved a distance from the position where it was last coupled to the adapter 1210. Such an embodiment can reduce false alarms, which may be caused by radio interference, traveling only a short distance from the medicament delivery device 1100, and so forth. For example, the computing device 1510 can be configured to produce an alert when it loses connectivity with the medicament delivery device 1100 and is more than ⅛ of a mile from the last location at which the computing device 1510 was linked to the adapter 1210. Any other suitable threshold, such as 200 feet, ½ mile, 5 miles, etc. is possible. In addition or alternatively, an alert can be generated if the communication link is lost and the computing device 1510 is moving at more than a threshold velocity, such as 10 mph, 20 mph, 50 mph, etc. which may be associated with traveling by automobile. In this manner, the leash feature may reduce false alarms that can occur where the user is within walking distance of the medicament delivery device 1100 (e.g., the user may be walking within a large building and the communications between the computing device 1510 and the adapter 1410 may be temporarily disrupted.

In some embodiments, as described in further detail herein, the computing device 1510 and/or the adapter 1210 can include a status tracking functionality such that when the medicament delivery device 1100 (and/or a simulated medicament delivery device 1100) changes status, the adapter 1210 can adjust the communications protocol and/or characteristics. For example, in some embodiments, the adapter 1210 can enhance the electronic communications with the computing device 1510 by changing a signaling rate, signal power and/or the information contained in a signal sent via the radio 1212 in response to the actuation of the medicament delivery device 1100 (and/or a simulated medicament delivery device 1100).

In some embodiments, for example, the adapter 1210 can be operable to switch between several connection and/or communication modes (each of which may be associated with different broadcast intervals, power consumption levels or the like). For example, the adapter 1210 can have an off mode, where there is substantially no electrical activity (e.g., no power draw) associated with the processor 1216 and/or the radio 1212. When the adapter 1210 is in the off mode, there is no communications between the adapter 1210 and the computing device 1510 and/or the remote device 1610. In some embodiments, an electrical connection between a power source (e.g., a battery) and the processor 1216 and/or the radio 1212 may be mechanically isolated when the adapter 1210 is in the off mode. In other embodiments, the power source can remain electrically coupled to the processor 1216 and/or the radio 1212, but communications activity can be otherwise curtailed to limit power consumption.

As another example, the adapter 1210 can be operable in a connectable mode where the adapter 1210 is available to link with and/or is soliciting a link with the computing device 1510. For example, when in the connectable mode, the adapter 1210 can repeatedly send a signal to advertise its availability to establish a communication link (or "pair with") the computing device 1510 via the radio 1212. In some embodiments, the advertising signal can be sent in a non-periodic advertising interval, which can avoid synchronization with the computing device 1510 (e.g., avoid the adapter 1210 advertising on a cycle that does not overlap with a computing device 1510 "listening" cycle). In some embodiments, the advertising interval can be based, at least in part, on the status of the medicament delivery device 1100. In this manner, the adapter 1210 can control the electronic communications with the computing device 1510 to limit the power consumption during periods when such communications are less likely. For example, if the medicament delivery device 1100 is disposed within the adapter 1210 a relatively long advertising interval (such as about 7 ms, about 10 ms, about 20 ms, about 152.5 ms, about 211.25 ms, about 500 ms, about 760 ms, about 1 s, about 5 s, 5 min, and/or any other suitable interval therebetween) can be chosen. If, on the other hand, the medicament delivery device 1100 has been removed from the adapter 1210, a relatively short advertising interval (such as about 1 ms, about 3, ms, about 10 ms, about 20 ms and/or any other suitable interval) can be chosen and/or power can be increased to the radio 1212. In this way, the adapter 1210 can conserve power when the medicament delivery device 1100 is not configured to deliver a medicament, while prioritizing connectivity and/or reducing latency when the medicament delivery device 1100 is poised to deliver a medicament.

As another example, the adapter 1210 can have a connected mode, for example, where the adapter 1210 is linked with the computing device 1510 (i.e., the adapter 1210 and the computing device 1510 form a piconet). When the adapter 1210 is in the connected mode, the adapter 1210 can periodically exchange messages with the computing device 1510 to maintain the connection. In some embodiments, the communication interval (i.e., the time interval between successive signals and/or portions of a signal, also referred to herein as a "connection interval") can be selected in accordance with a status of the adapter 1210 and/or medicament delivery device 1100 to minimize power consumption. For example, the communication interval can be 0.5 s, 1 s, 2 s, and/or any other suitable interval. In some embodiments, the adapter 1210 can selectively enter a particular "mode" of communications when connected with the computing device 1510. For example, the Bluetooth® Low Energy protocol employs a sleep mode, a sniff mode and park mode to facilitate conservation of power of the slave device (i.e., the adapter 1210, in this example). In some embodiments, the adapter 1210 can selectively enter the sleep, sniff, and/or park mode once connected, in response to a change in status of the medicament delivery device 1100 (e.g., removed, armed, actuated) and/or if the data associated with the medicament delivery device 1100 is not transferred for a period of time.

In some embodiments, for example, the adapter 1210 can be configured such that the radio 1212 is configured to send a first signal characterized by a first communication interval and/or mode when the medicament delivery device 1100 is in a first configuration. The first signal can be, for example, an advertising signal characterized by a first advertising interval. In other embodiments, the first signal can be a signal to maintain an already-exiting pairing between the adapter 1210 and the computing device 1510. The first configuration of the medicament delivery device 1100 can be, for example, a "standby" configuration (when the device is within and/or coupled to the adapter 1210). Alternatively, the first configuration can be any other suitable configuration (e.g., an armed configuration, a "power off" configuration or the like). The radio is configured to send a second signal characterized by a second communication interval and/or mode when the medicament delivery device is in a second configuration. The second communication interval can be different from the first communication interval.

In some embodiments, the computing device 1510 can send a signal to the adapter 1210 to cause the adapter to emit an audible output. In some embodiments, there may be limited space in the memory 1218 of the adapter 1210 to store voice prompts and/or customized voice prompts, and/or the memory 1218 may be ROM memory or another type of memory that is not writeable and/or requires significant time, computational resources, and/or power to alter. In such an embodiment, sending a signal from the computing device 1510, which may have more memory and/or computational power, to cause the adapter 1210 to generate an output, can extend the battery life of the adapter 1210 and/or can allow the adapter 1210 to be more flexible and/or customizable than the processor 1216, the memory 1218. Such methods can further address the power constraints of the adapter 1210 by using less power than if the output were generated entirely by the adapter 1210.

In other embodiments, the electronic configuration of the adapter 1210 can facilitate methods of updating an instruction script and/or voice prompt stored in the memory 1218 of the adapter 1210. For example, in some embodiments, the adapter 1210 can receive signals from the computing device 1510 via the radio 1212 that include information associated with an instruction script and/or voice prompt of the types described herein. This information can then be written to the memory 1218, thus allowing the voice prompts to be updated using the wireless communications capabilities described herein. These methods avoid the need to have the voice prompts contained in a ROM mask, which can be difficult to update. Moreover, these methods allow for the user to customize their voice prompts (e.g., with a specific user's voice, with customized content or the like).

In some embodiments, the adapter 1210 can be associated with a unique identifier and/or part number. In such an embodiment, when the computing device 1510 pairs with the adapter 1210 the computing device 1510 (e.g., by communicating with the remote device 1610, which may include a database of adapters 1210) can retrieve information associated with the medicament delivery device 1100, such as type of medicament, expiration date, particular use instructions, and so forth.

Although described as facilitating a user-implemented update to a voice prompt, in other embodiments, the adapter 1210 (and any of the system described herein) can be configured to update the voice prompts based on the user's past history (e.g., via the use module 1222). In this manner, the systems and methods described herein can be used to produce a "smart" or "trainable" device. In some embodiments, the medicament delivery device 1100 can be a simulated medicament delivery device intended for use training a user in the operation of an actual medicament delivery device. In such an embodiment, the adapter 1210 (and/or the simulated medicament delivery device 1100 itself) can be operable to detect whether the simulated medicament delivery device was used properly. For example, via input received from the sensor 1214 (and/or a series of sensors), the adapter 1210 can be operable to detect whether the simulated medicament delivery device was properly armed, whether it was properly positioned to simulate delivery of medicament, whether sufficient force was applied to actuate the simulated medicament delivery device, whether the medicament delivery device was held in position for a sufficient period of time, and so forth. The adapter 1210 can send a signal to the computing device 1510 such that personalized instructions can be provided to the user by the computing device 1510 and/or the adapter 1210. For example, if the user applies insufficient force to actuate the simulated medicament delivery device, this information can be stored within the memory 1218 and the adapter 1210, the simulated device 1100, and/or the computing device 1510 can be operable to instruct the user to apply additional force and/or to remind the user that insufficient force was applied in previous instances. Furthermore, in some embodiments, a record of simulated medicament delivery device use can be stored by the adapter 1210, the computing device 1510, and/or the remote device 1610, such that personalized instructions in the event the user attempts to use an actual medicament delivery device 1100. For example, the computing device 1510 can remind the user of mistakes made with a simulated medicament delivery device, for example, to remind the user that he or she has a history of applying insufficient force when practicing with the simulated medicament delivery device. Similarly stated, the computing device and/or the remote device 1610 can be operable to provide information to the user of the medicament delivery device 1100 based on data associated with a simulated medicament delivery device.

In some embodiments, an application (executing on the processor 1516 of the computing device 1510) can be operable to detect and/or pair with multiple adapters. For example, the communication device 1510 can be operable to detect one or more adapters (coupled to medicament delivery devices) at a retail location, such as a pharmacy. In such an embodiment, the computing device 1510 can send a signal to and/or receive a signal from the remote device 1610 indicating the location of the adapters. The remote device 1610, in turn can provide information to users (e.g., via the Internet) of the location of the adapters. Thus, the remote device 1610 can be operable to provide, for example, to a user, sales rep, healthcare professional, etc. information about the availability of a particular medicament delivery device or particular type of medicament delivery device. Furthermore, in the event of a medicament recall or expiration, the remote device 1610 can have a database of locations having the recalled or expired medicament.

Figure 3:
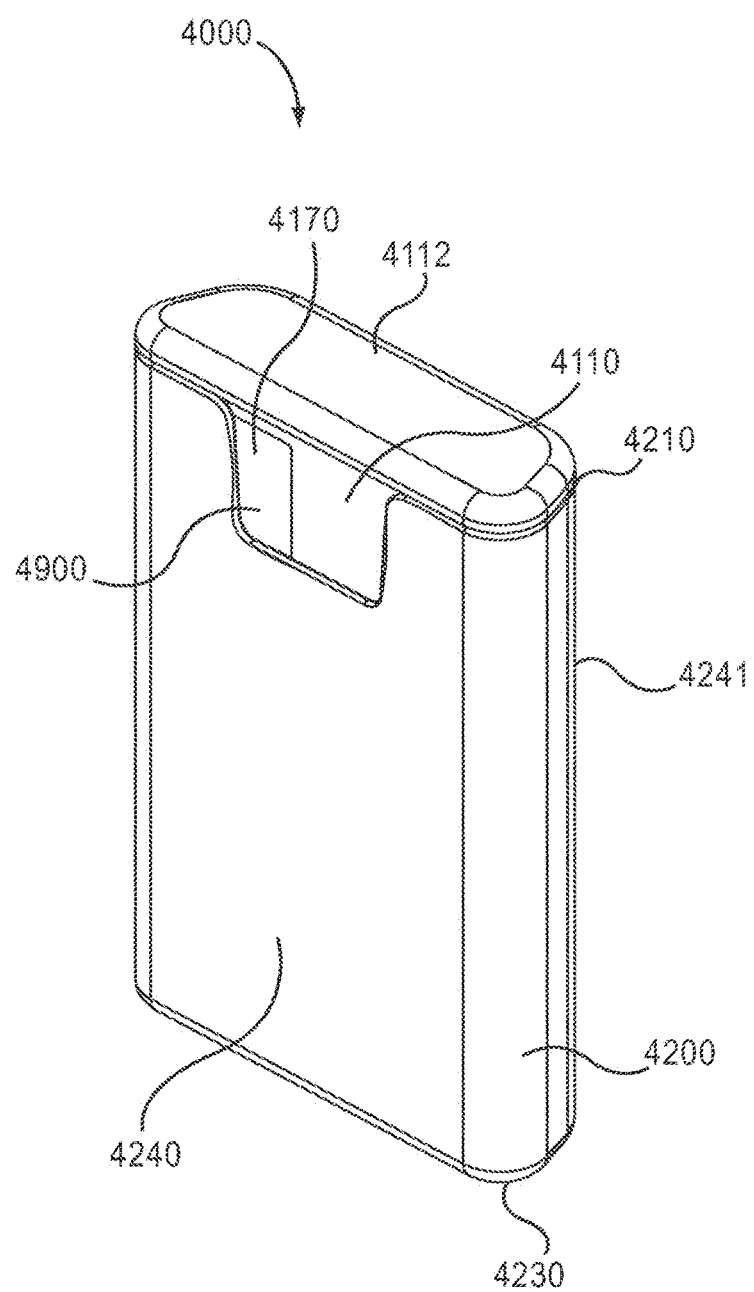
FIGS. 3 and 4 are perspective views of a medical injector according to an embodiment of the invention, in a first configuration.
Figure 4:
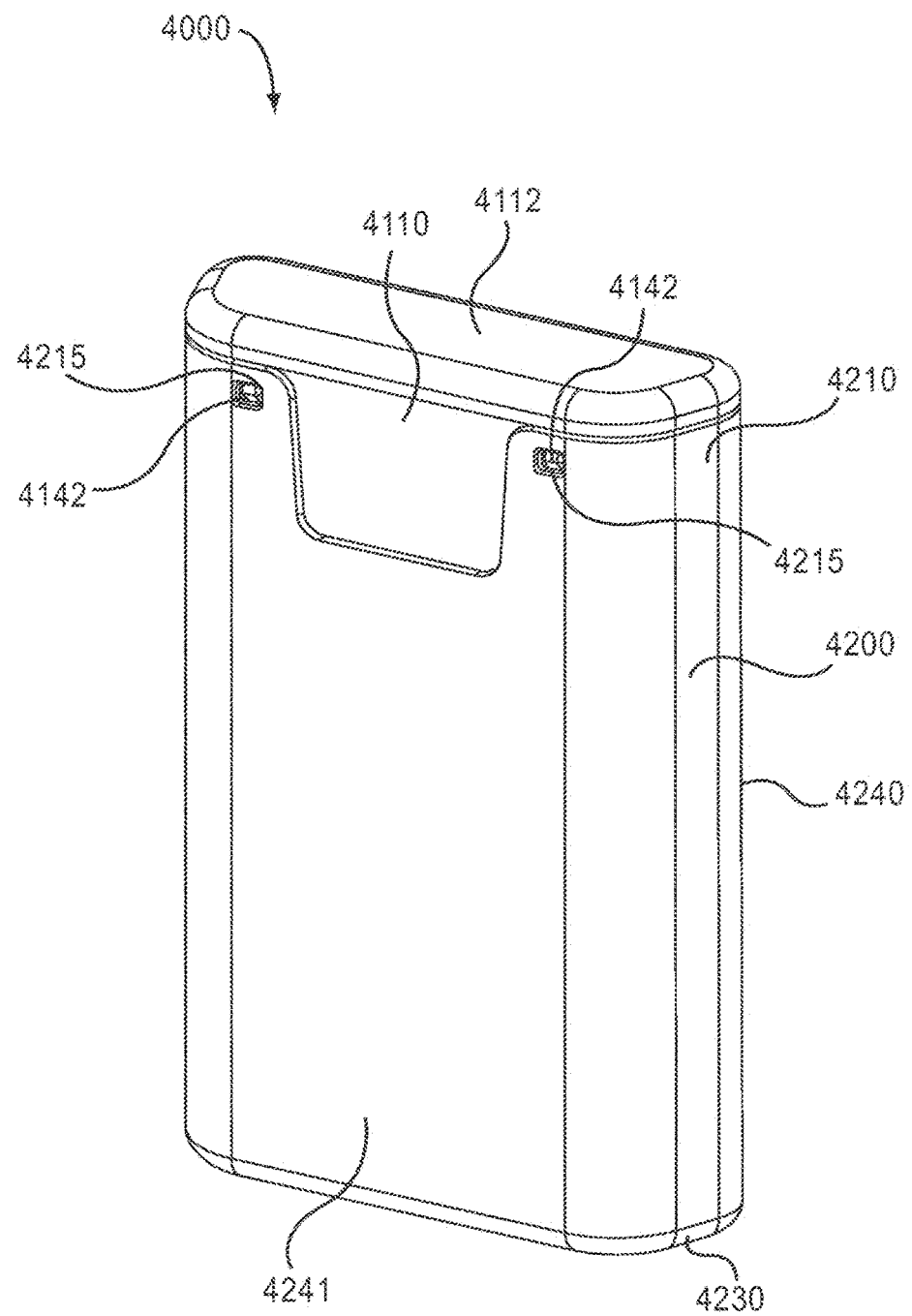
Figure 5:
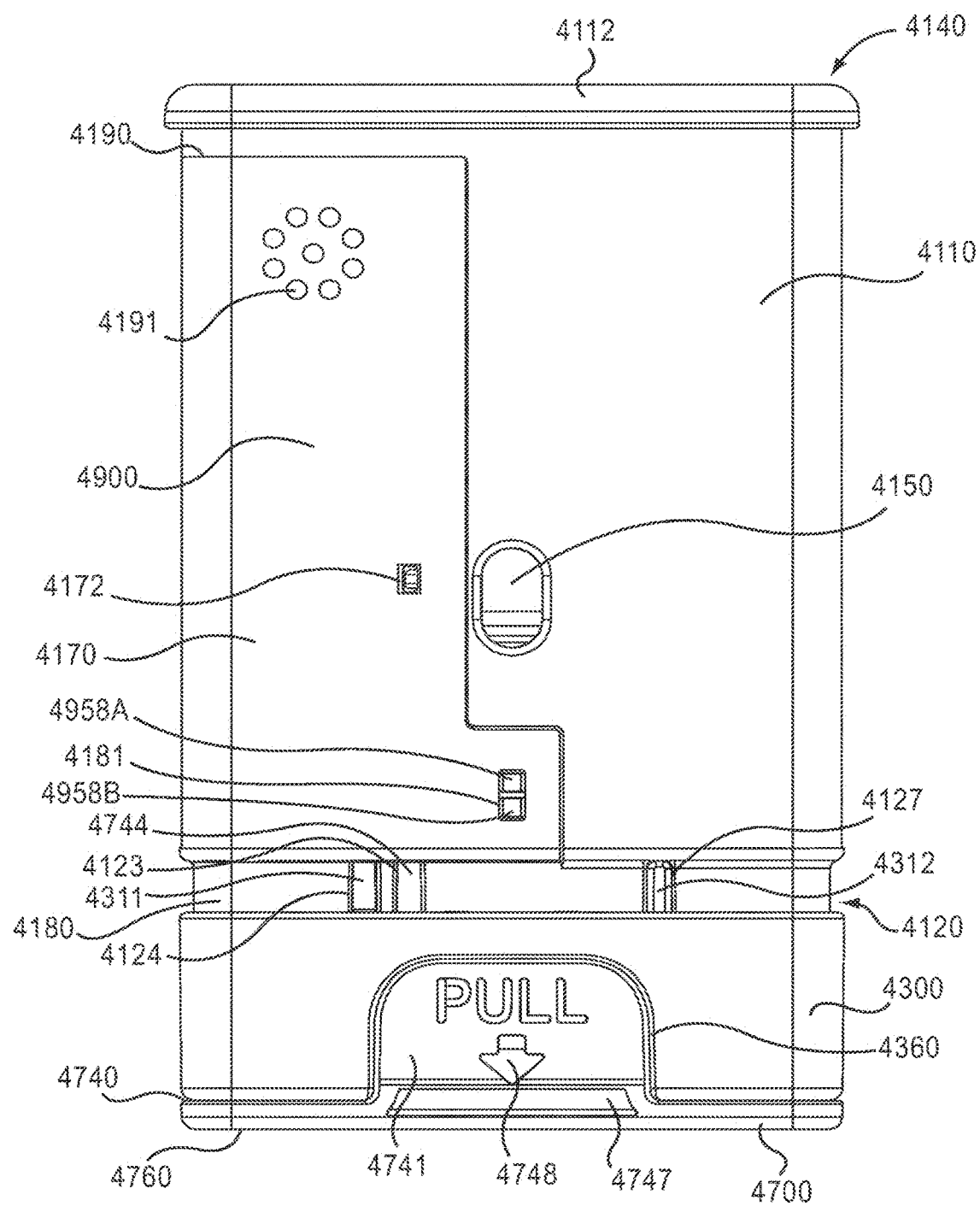
FIG. 5 is a front view of the medical injector illustrated in FIG. 3 with the cover removed.

The methods and systems described herein can be used in conjunction with any suitable medicament delivery device. For example, FIGS. 3-34 show a medical injector 4000 as another example of a delivery device that can be used in conjunction with and/or as a part of the delivery systems and methods described herein. FIGS. 3-4 are perspective views of the medical injector 4000 in a first configuration (i.e., prior to use). The medical injector 4000 includes a housing 4110, a delivery mechanism 4500 (see e.g., FIG. 12), an electronic circuit system 4900 (see e.g., FIGS. 13-23), a cover 4200 (see e.g., FIGS. 24-25), a safety lock 4700 (see e.g., FIGS. 26-29) and a base 4300 (see e.g., FIGS. 30-31). A discussion of the components of the medical injector 4000 will be followed by a discussion of the operation of the medical injector 4000.

As shown in FIGS. 5-11, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient to monitor the status and/or contents of a medicament container 4560. For example, by visually inspecting the status indicator apertures 4150, 4151, a patient can determine whether the medicament container 4560 contains a medicament and/or whether a medicament has been dispensed.

Figure 9:
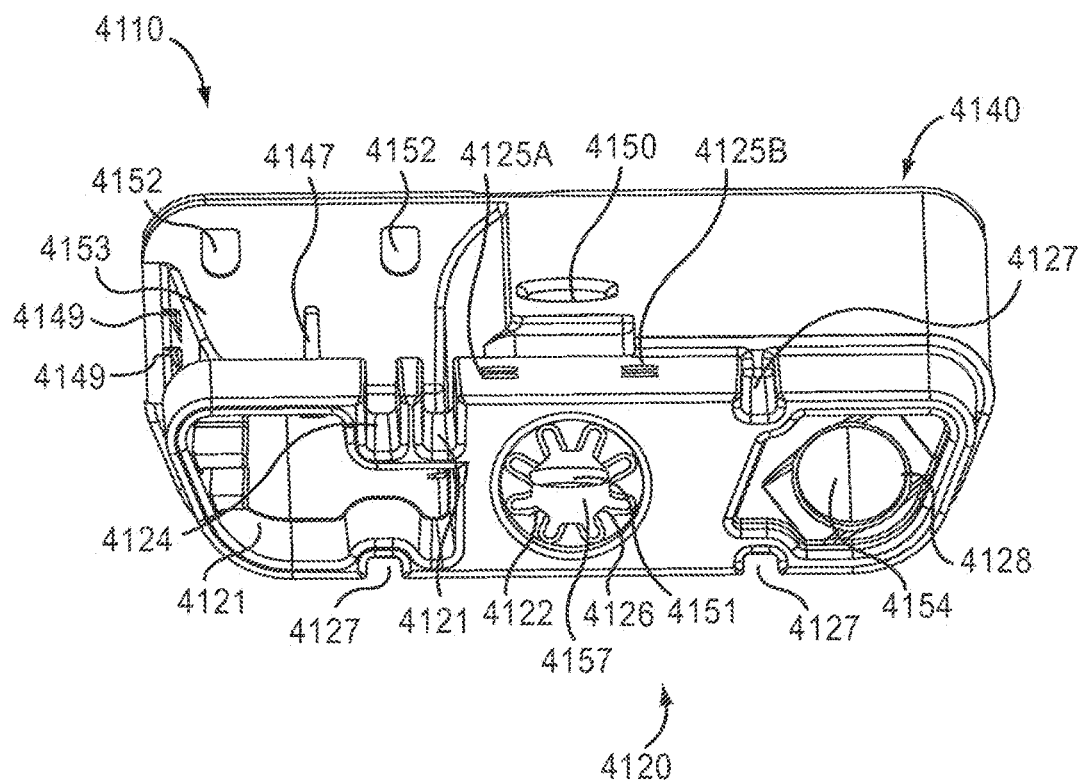
FIG. 9 is a bottom perspective view of a housing of the medical injector illustrated in FIG. 3.
Figure 10:
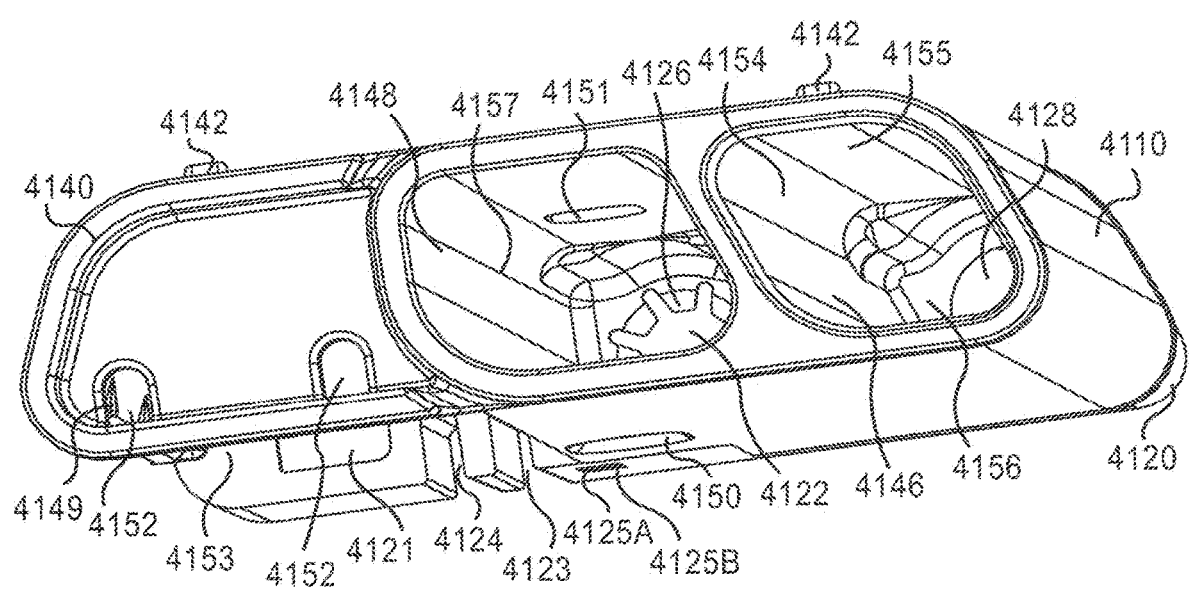
FIG. 10 is a top perspective view of a housing of the medical injector illustrated in FIG. 3.

As shown in FIGS. 9 and 10, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and the release member 4540 of the medicament delivery mechanism 4500 (see e.g., FIG. 12) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144, as described in further detail herein, and the gas cavity 4154 is in fluid communication with a region outside the housing 4110 via a safety lock aperture 4128.

The medicament cavity 4157 is configured to receive a portion of the delivery mechanism 4500. In particular, the carrier 4520, the moveable member 4530 and the needle 4512 of the medicament delivery mechanism 4500 are movably disposed in the medicament cavity 4157. The medicament cavity 4157 is in fluid communication with a region outside the housing 4110 via a needle aperture 4122.

The electronic circuit system cavity 4153 is configured to receive the electronic circuit system 4900. The housing 4110 has protrusions 4149 (see e.g., FIG. 8) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 6) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments, the gas cavity 4154 can be fluidically and/or physically isolated from the medicament cavity 4157.

Figure 6:
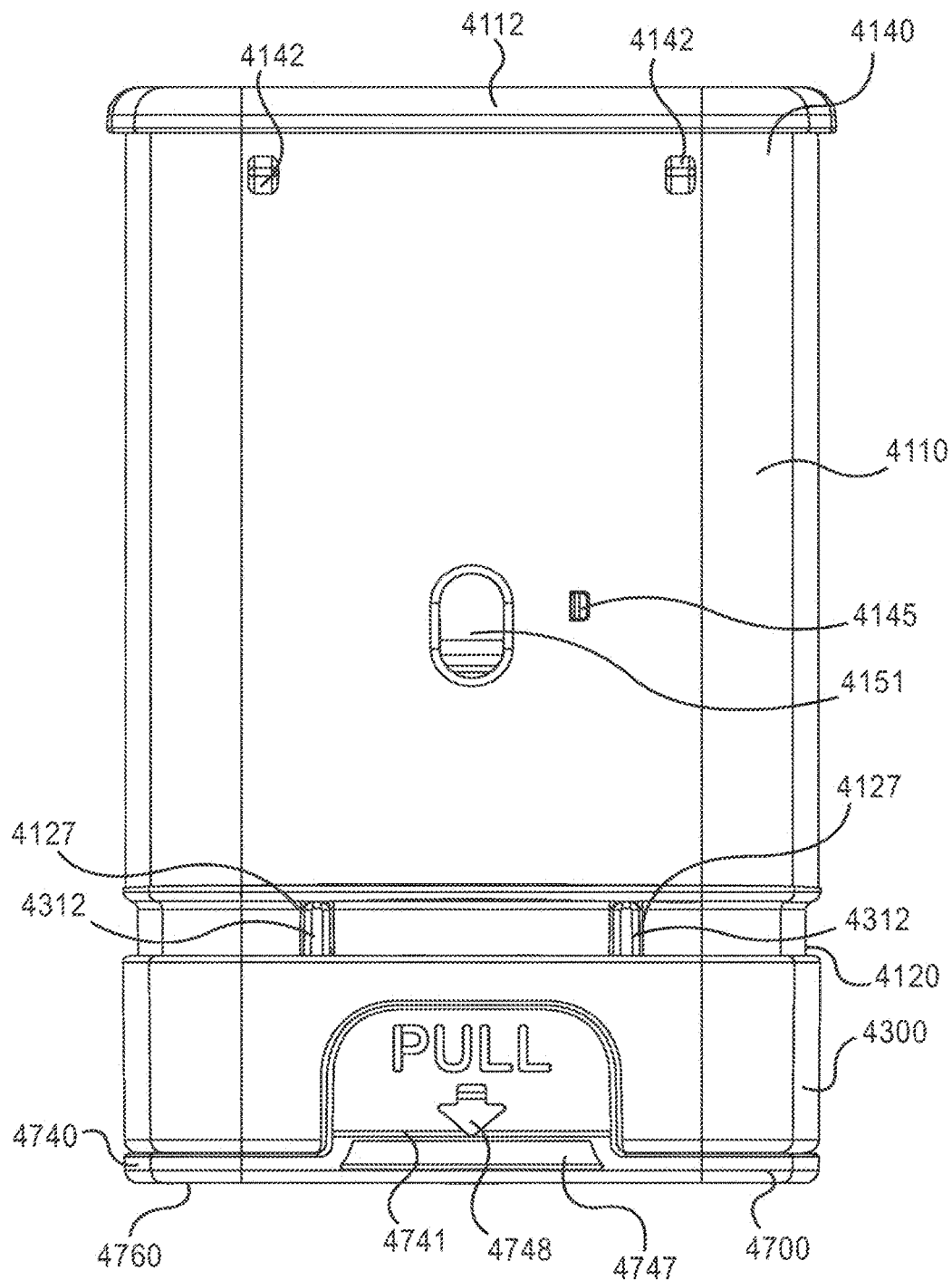
FIG. 6 is a back view of the medical injector illustrated in FIG. 3 with the cover removed.

The proximal end portion 4140 of the housing 4110 includes a proximal cap 4112, a speaker protrusion 4147 (see e.g., FIGS. 8 and 9), and cover retention protrusions 4142 (see e.g., FIGS. 4 and 6). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 11:
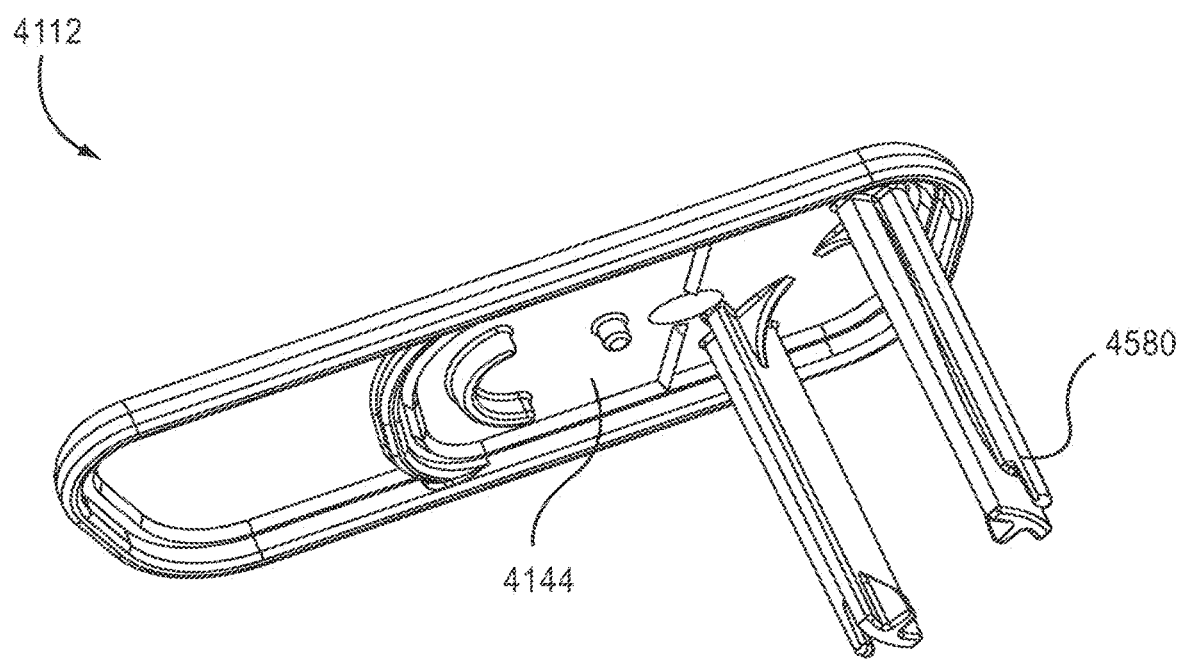
FIG. 11 is a perspective view of a proximal cap of the medical injector illustrated in FIG. 3.

As shown in FIG. 11, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 7:
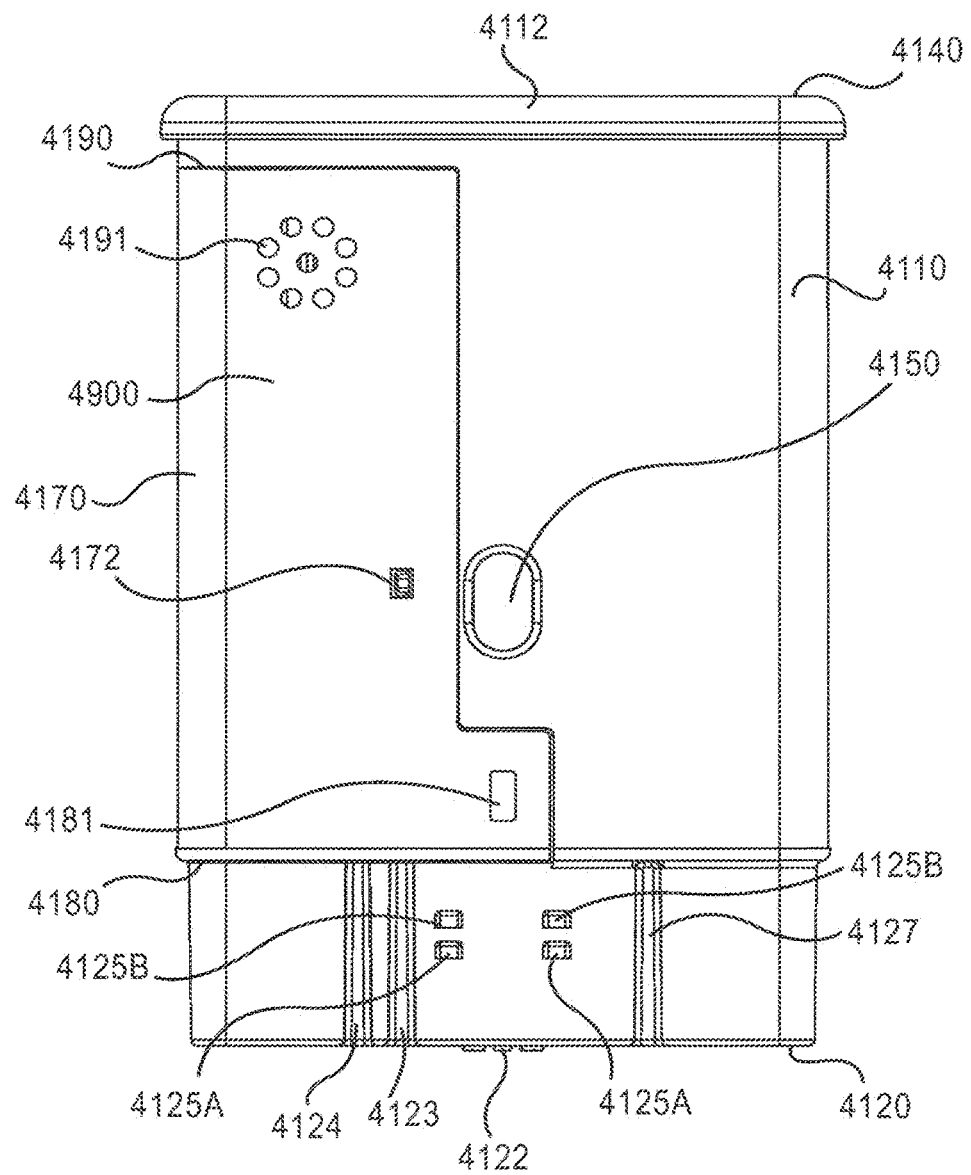
FIG. 7 is a front view of a portion of the medical injector illustrated in FIG. 3.
Figure 8:
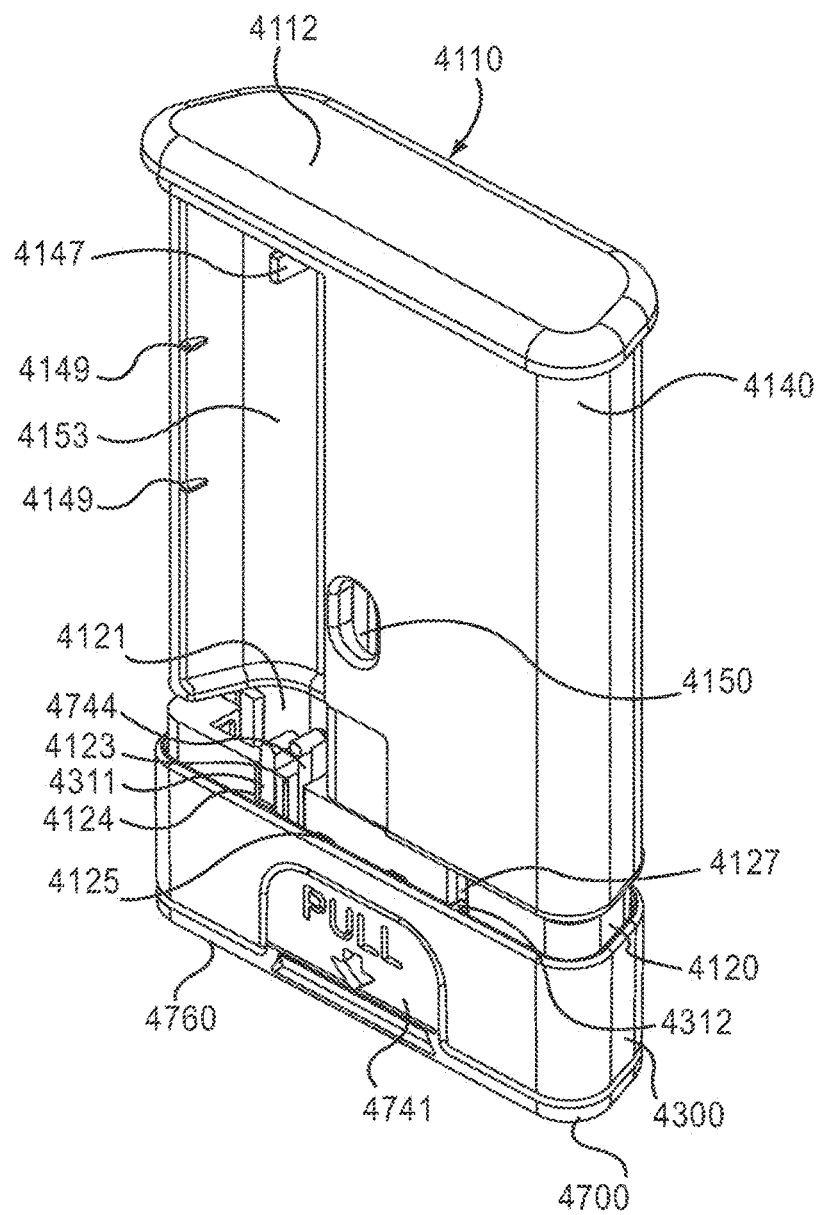
FIG. 8 is a perspective view of a portion of the medical injector illustrated in FIG. 3.

As shown in FIGS. 7 and 9, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 25), as described in further detail herein.

The needle aperture 4122 is configured to allow the needle 4512 (see e.g., FIG. 12) to exit the housing 4110 when the medical injector 4000 is actuated. The portion of the sidewall of the housing 4110 that defines the needle aperture 4122 includes multiple sheath retention protrusions 4126. In some embodiments, the sheath retention protrusions can interact with a plurality of ribs 4728 of the needle sheath 4720 (see e.g. FIG. 29) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 25 and 26). As described in more detail below, the safety lock protrusion 4742 is received within an opening 4554 between extensions 4552 of a release member 4540 such that activation of the medical injector 4000 is prevented when the safety lock 4700 is in place. The safety lock 4700, its components and functions are further described herein.

The distal base retention recesses 4125A are configured to receive the base connection knobs 4358 of the base 4300 (see e.g., FIG. 30) when the base 4300 is in a first position relative to the housing 4110. The proximal base retention recesses 4125B are configured to receive the base connection knobs 4358 of the base 4300 when the base 4300 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4300 can move proximally relative to the housing 4110, but cannot move distally relative to the housing 4110. Said another way, the distal base retention recesses 4125A are configured to prevent the base 4300 from moving distally when the base 4300 is in a first position and the proximal base retention recesses 4125B are configured to prevent the base 4300 from moving distally when the base 4300 is in a second position. Similarly stated, the proximal base retention recesses 4125B and the base connection knobs 4358 cooperatively prevent "kickback" after the medical injector 4000 is actuated.

The base actuator groove 4124 is configured to receive an actuator 4311 of the base 4300. As described in more detail herein, the actuator 4311 of the base 4300 is configured to engage the electronic circuit system 4900 when the base 4100 is moved with respect to the housing 4110. The base rail grooves 4127 are configured to receive the guide members 4312 of the base 4300. The guide members 4312 of the base 4300 and the base rail grooves 4127 of the housing 4110 engage each other in a way that allows the guide members 4312 of the base 4300 to slide in a proximal and/or distal direction within the base rail grooves 4127 while limiting lateral movement of the guide members 4312. This arrangement allows the base 4300 to move in a proximal and/or distal direction with respect to the housing 4110 but prevents the base 4300 from moving in a lateral direction with respect to the housing 4110.

Figure 12:
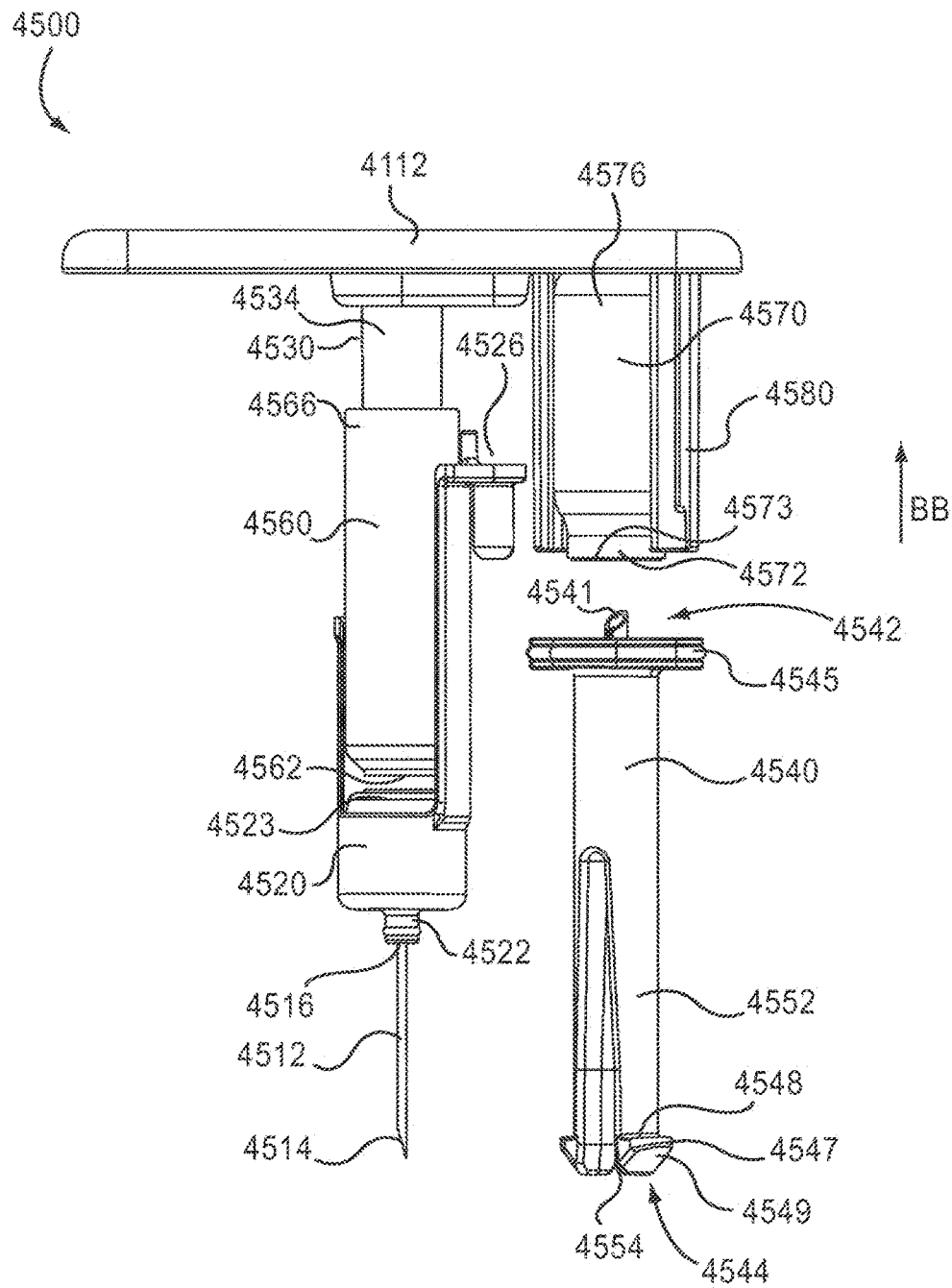
FIG. 12 is a front view of a medicament delivery mechanism of the medical injector illustrated in FIG. 3.
Figure 13:
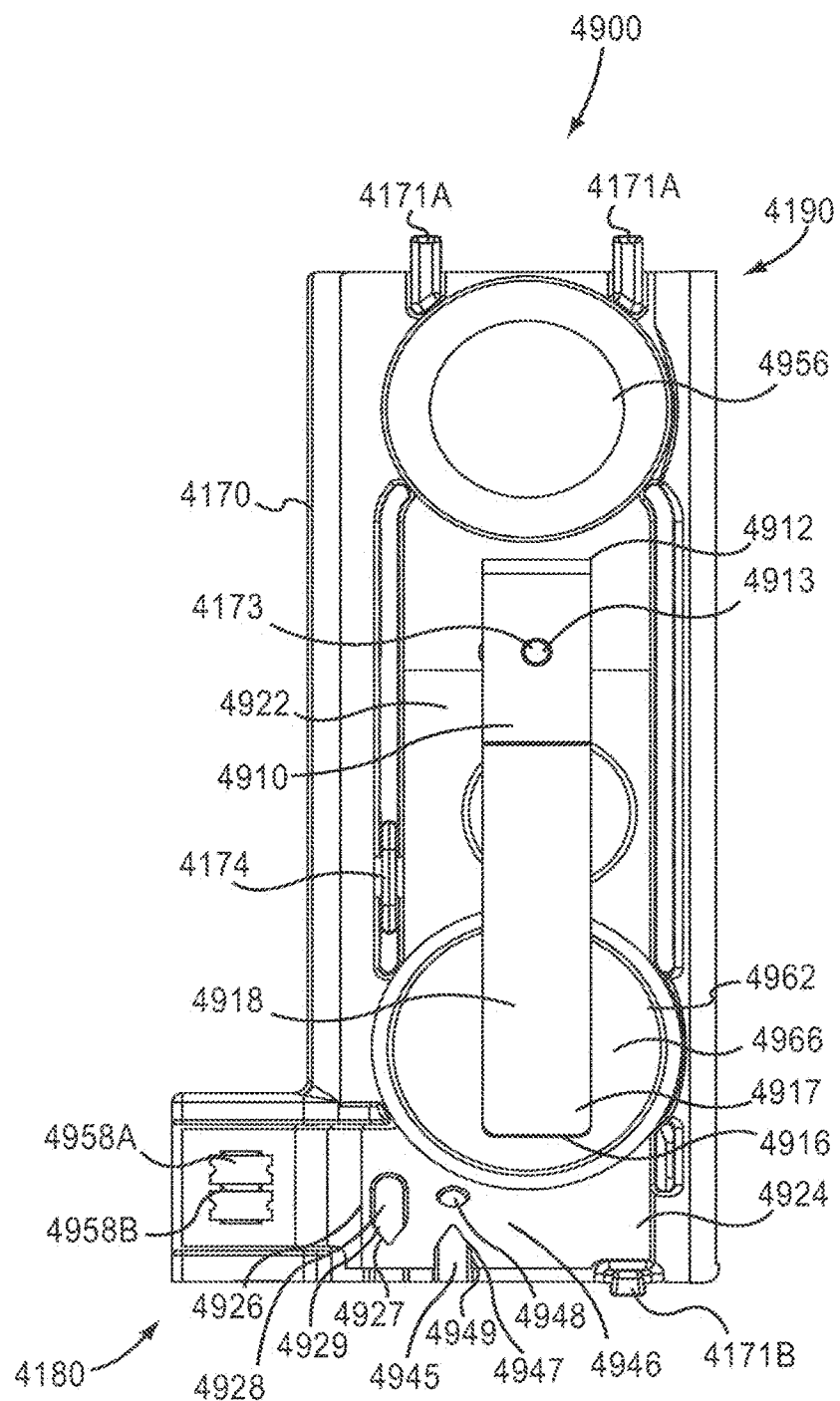
FIG. 13 is a back view of an electronic circuit system of the medical injector illustrated in FIG. 3.
Figure 14:
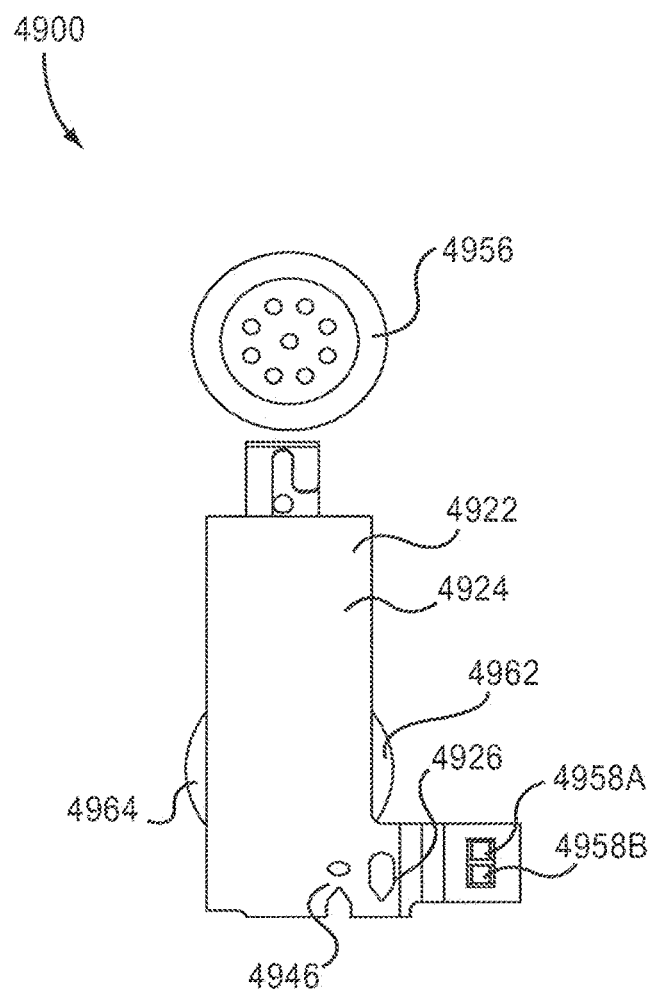
FIG. 14 is a front view of a portion of the electronic circuit system of the medical injector illustrated in FIG. 13.
Figure 15:
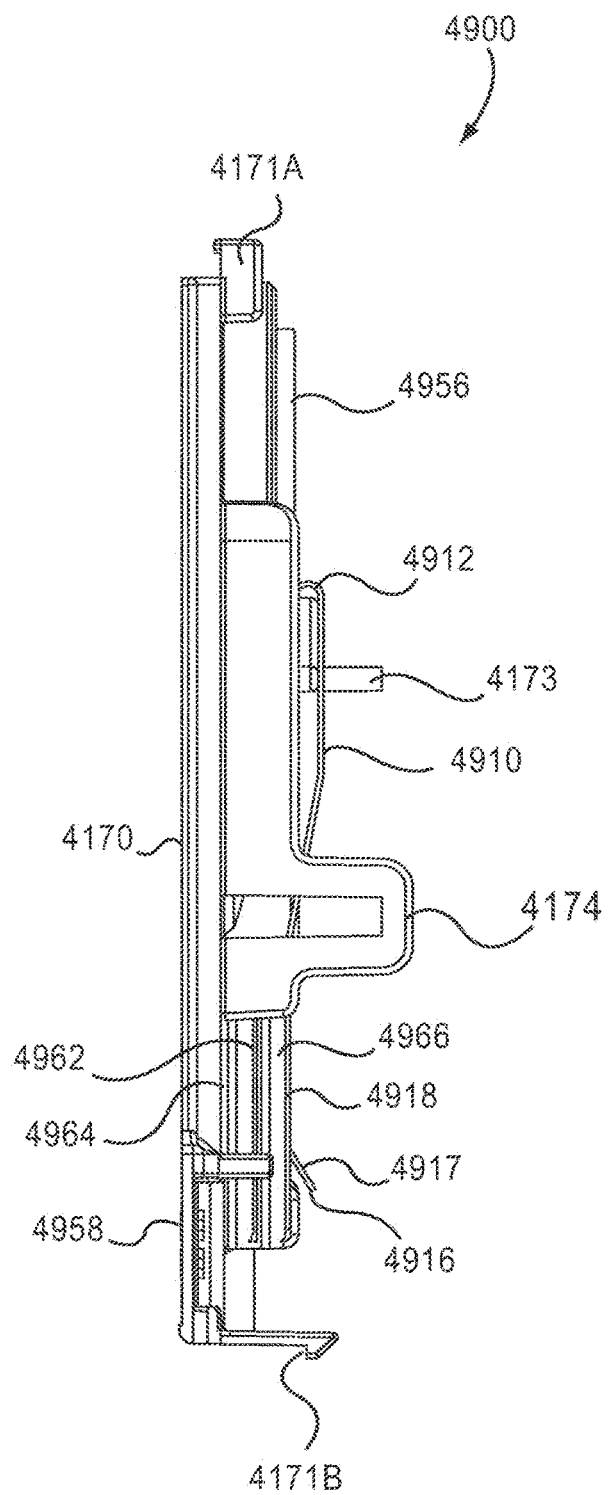
FIG. 15 is a side view of the electronic circuit system of the medical injector illustrated in FIG. 13.

FIG. 12 shows the medicament delivery mechanism 4500 of the medical injector 4000. The medical injector 4000 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the medicament delivery mechanism 4500 and related operation of the medical injector 4000 is included below.

The medicament delivery mechanism 4500 includes a needle 4512, a carrier 4520, a movable member 4530, a medicament container 4560, a gas container 4570, and a release member 4540. As described above, the needle 4512, carrier 4520, movable member 4530 and medicament container 4560 are disposed within the medicament cavity 4157 of the housing 4110. The gas container 4570 and the release member 4540 are disposed within the gas cavity 4154 of the housing 4110.

The release member 4540 has a proximal end portion 4542 and a distal end portion 4544, and is movably disposed within the distal end portion 4156 of the gas cavity 4154. The proximal end portion 4542 of the release member 4540 includes a sealing member 4545 and a puncturer 4541. The sealing member 4545 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4541 of the proximal end portion 4542 of the release member 4540 is configured to contact and puncture a frangible seal 4573 on the gas container 4570 when the release member 4540 moves proximally within the gas cavity 4154, as shown by the arrow BB in FIG. 12.

The distal end portion 4544 of the release member 4540 includes extensions 4552. The extensions 4552 include projections 4547 that include tapered surfaces 4549 and engagement surfaces 4548. Further, the extensions 4552 define an opening 4554 between the extensions 4552. The tapered surfaces 4549 of the projections 4547 are configured to contact protrusions 4313 on a proximal surface 4310 of the base 4300 (see e.g., FIG. 30). The engagement surfaces 4548 of the projections 4547 are configured to extend through the safety lock aperture 4128 of the housing 4110 and contact a distal surface of the housing 4110. In this manner, the engagement surfaces 4548 of the projections 4547 limit proximal movement of the release member 4540 when the engagement surfaces 4548 are in contact with the distal surface of the housing 4110.

Figure 27:
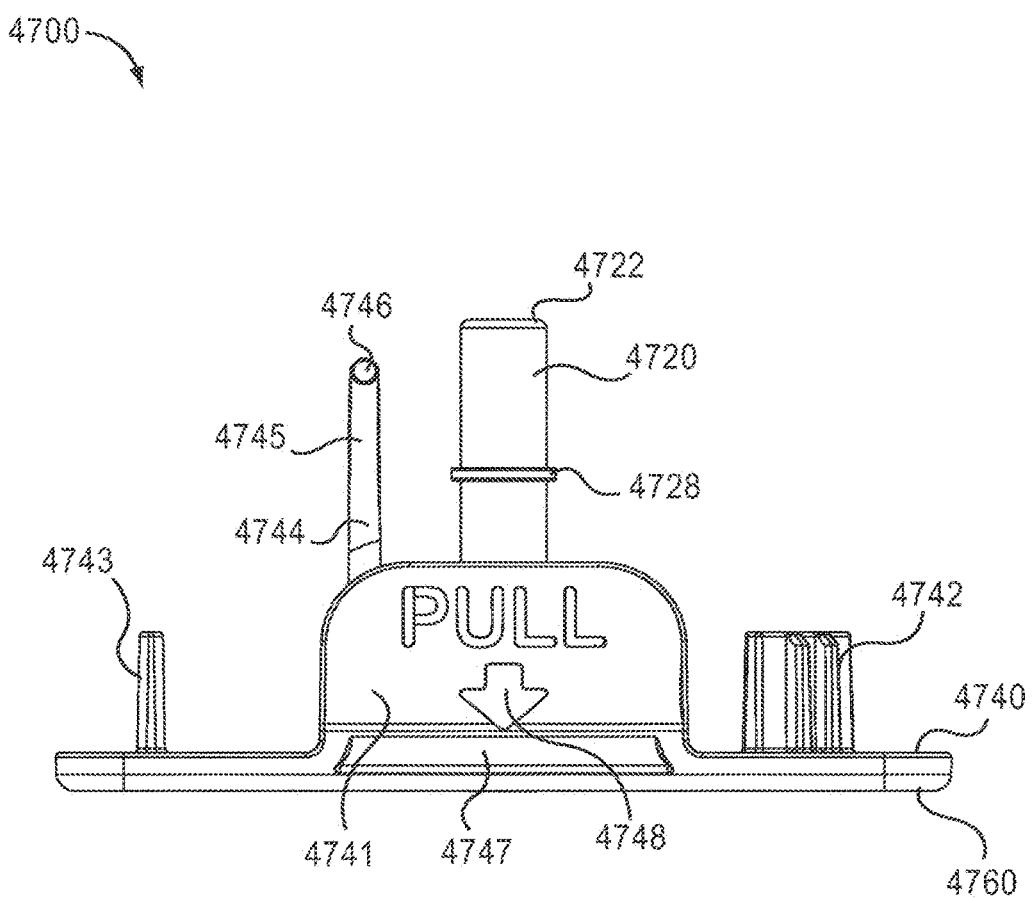
FIG. 27 is a front view of the safety lock of the medical injector illustrated in FIG. 26.

The opening 4554 defined by the extensions 4552 is configured to receive the safety lock protrusion 4742 of the safety lock 4700 (see e.g., FIG. 27). The safety lock protrusion 4742 is configured to prevent the extensions 4552 from moving closer to each other. Said another way, the safety lock protrusion 4742 is configured to ensure that the extensions 4552 remain apart and the engagement surfaces 4548 of the projections 4547 remain in contact with the distal end portion 4120 of the housing 4110. In some embodiments, for example, the release member 4540 and/or the extensions 4552 can be constructed from any suitable material configured to withstand deformation that may occur when exposed to a load over an extended period of time. In some embodiments, for example, the release member 4540 and/or the extensions 4552 can be constructed from brass.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4541 of the proximal end portion 4542 of the release member 4540 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The medicament container 4560 of the medicament delivery mechanism 4500 has a distal end portion 4562 and a proximal end portion 4566, and is configured to contain a medicament. The distal end portion 4562 of the medicament container 4560 contains a seal 4523. The seal 4523 is configured to burst when punctured by the proximal end 4516 of the needle 4512, as described below. The proximal end portion 4566 of the medicament container 4560 is configured to receive a piston portion 4534 of the movable member 4530.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4560. In this manner, the piston portion 4534 of the movable member 4530 can apply pressure to a medicament contained in the medicament container 4560. The piston portion 4534 can be constructed of a resilient, durable, and/or sealing material, such as a rubber.

The carrier 4520 of the medicament delivery mechanism 4500 includes a distal end portion 4522 and a proximal end portion 4526. The medicament container 4560 is coupled to the carrier 4520 via a "snap-fit" connection (not shown) such that the medicament container 4560 can move relative to the carrier 4520 between a first configuration and a second configuration during an injection event. In the first configuration, the carrier 4520 is configured to move within the medicament cavity 4157 such that movement of the carrier 4520 within the medicament cavity 4157 causes contemporaneous movement of the medicament container 4560 within the medicament cavity 4157. The proximal end portion 4516 of the needle 4512 is spaced apart from the seal 4523 of the medicament container 4560 when the carrier 4520 is in the first configuration. In the second configuration, the medicament container 4560 releases from the "snap-fit" causing the medicament container 4560 to move distally with respect to the carrier 4520, causing the proximal end portion 4516 of the needle 4512 to pierce the seal 4523. In this manner, the needle 4512 can be selectively placed in fluid communication with the medicament container 4560 to define a medicament delivery path (not shown).

Figure 20:
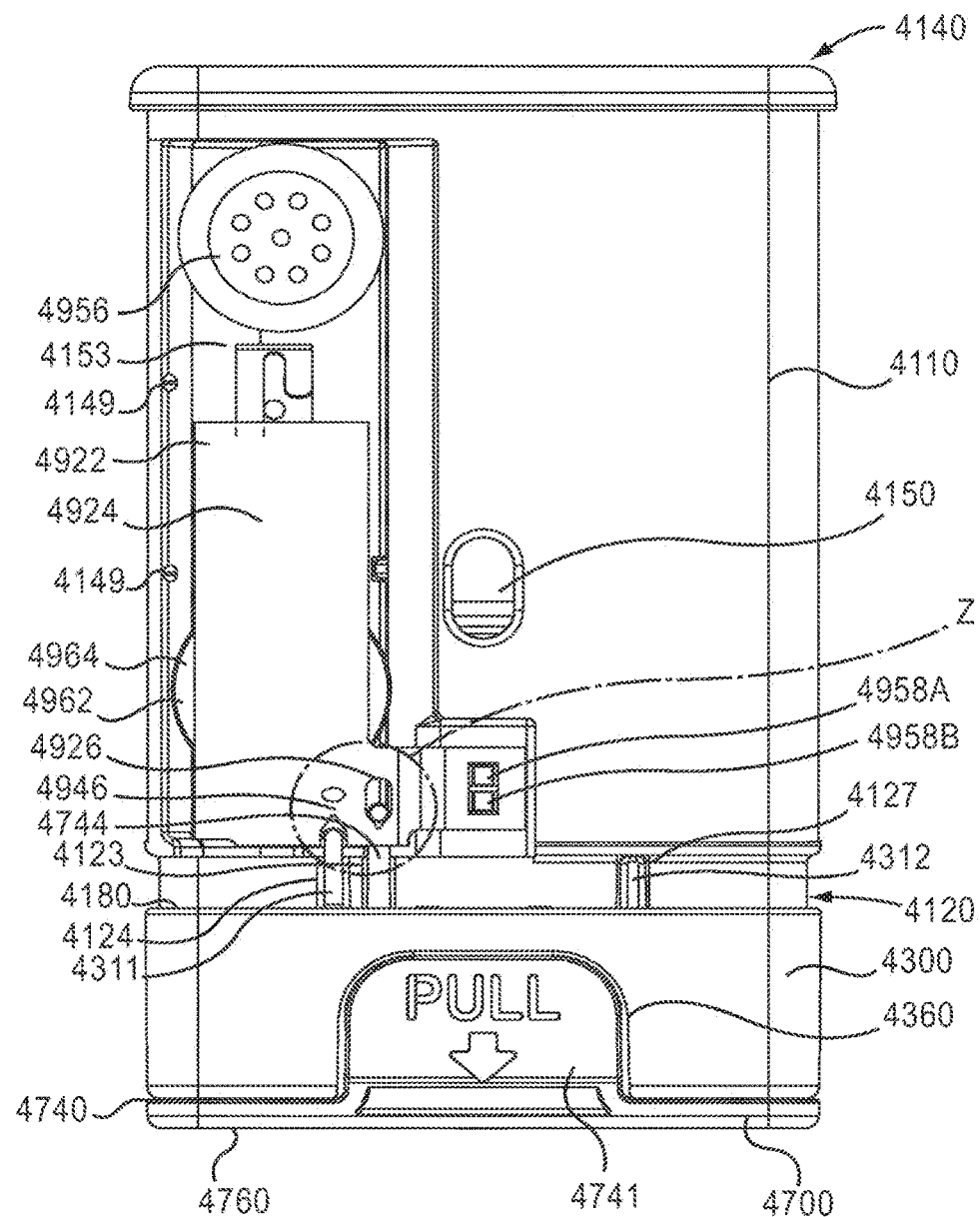
FIG. 20 is a front view of the medical injector illustrated in FIG. 3 in a first configuration showing the electronic circuit system.

FIGS. 13-22 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 20, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 16:
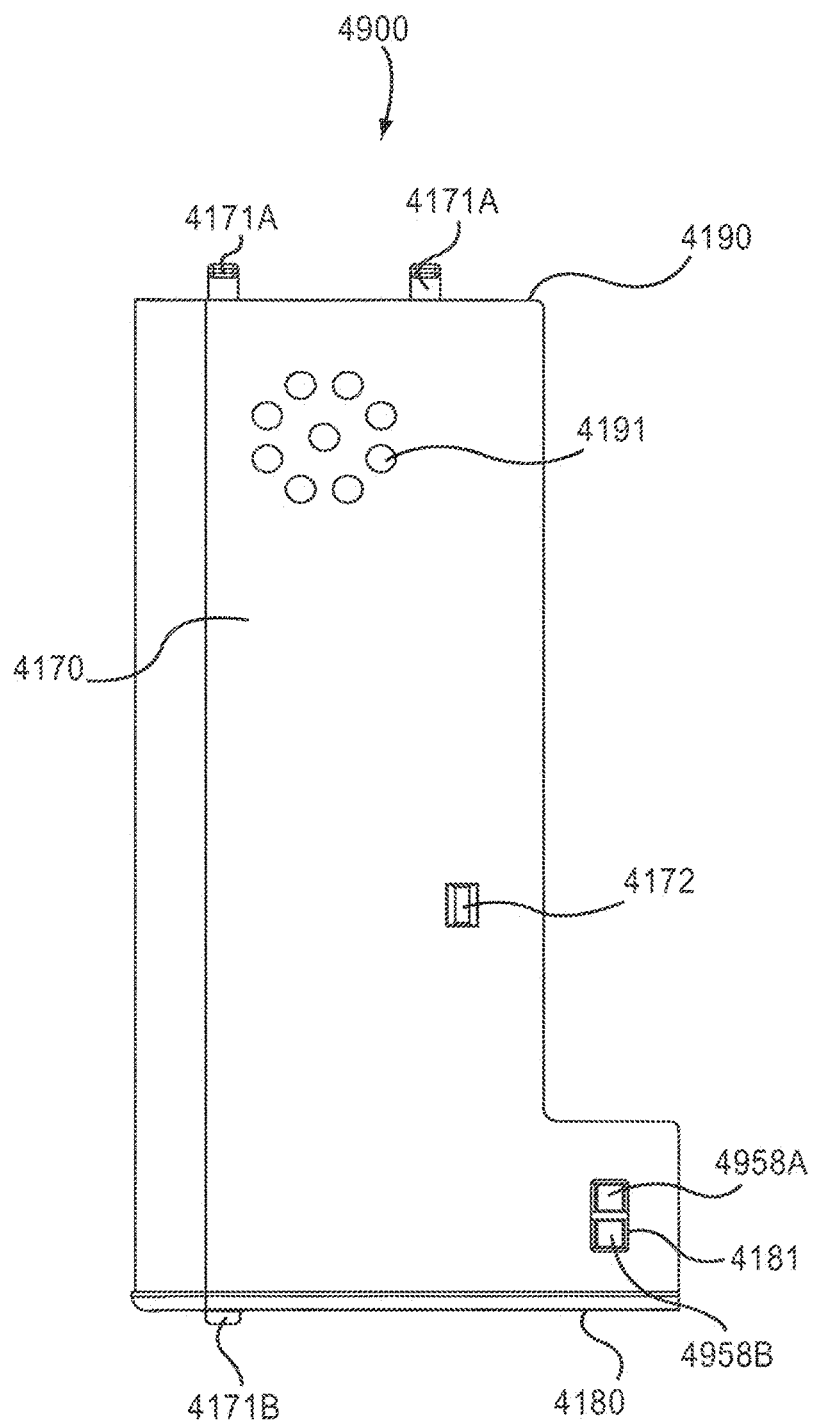
FIG. 16 is a front view of an electronic circuit system housing of the medical injector illustrated in FIG. 13.
Figure 17:
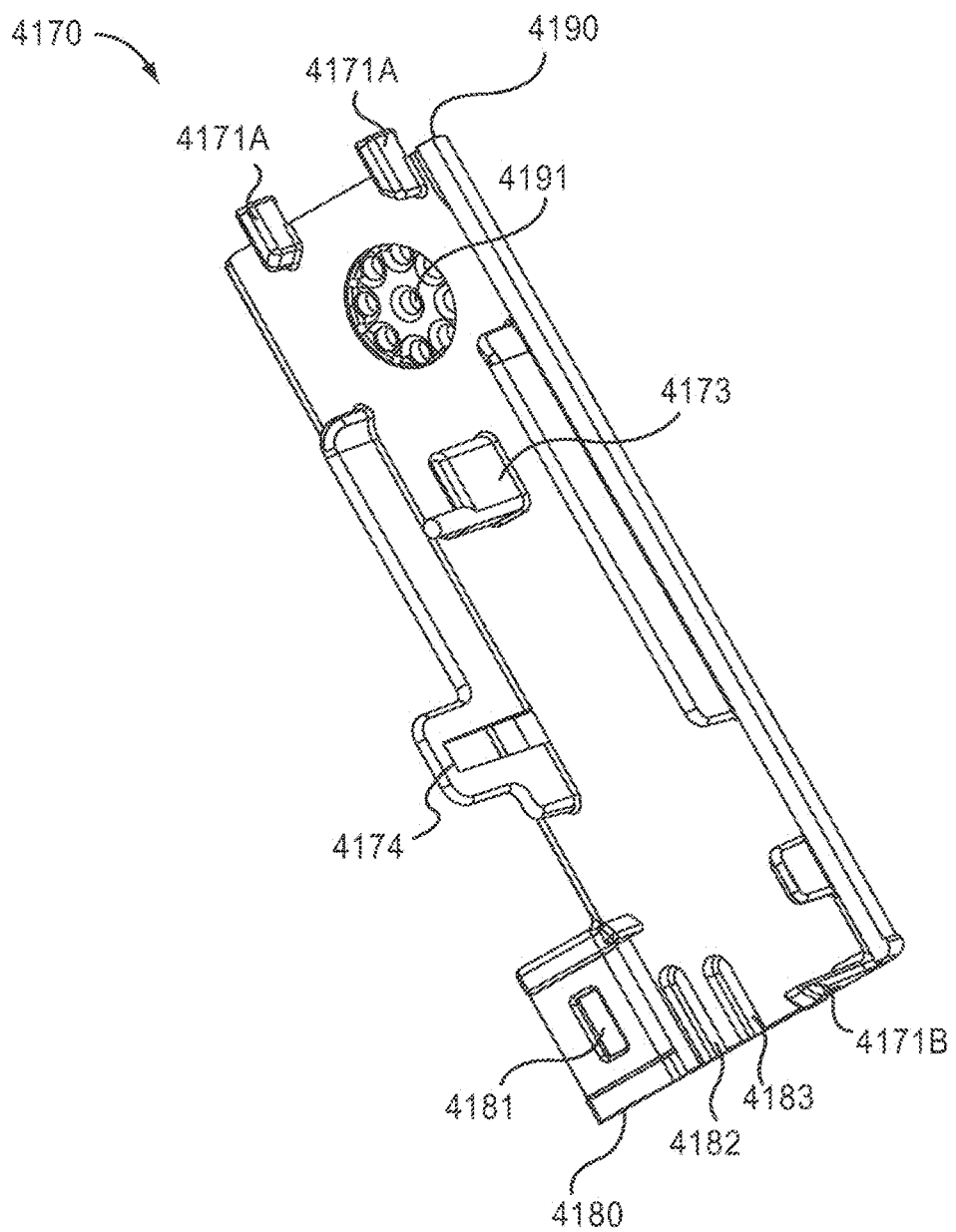
FIG. 17 is a perspective view of the electronic circuit system housing of the medical injector illustrated in FIG. 16.
Figure 18:
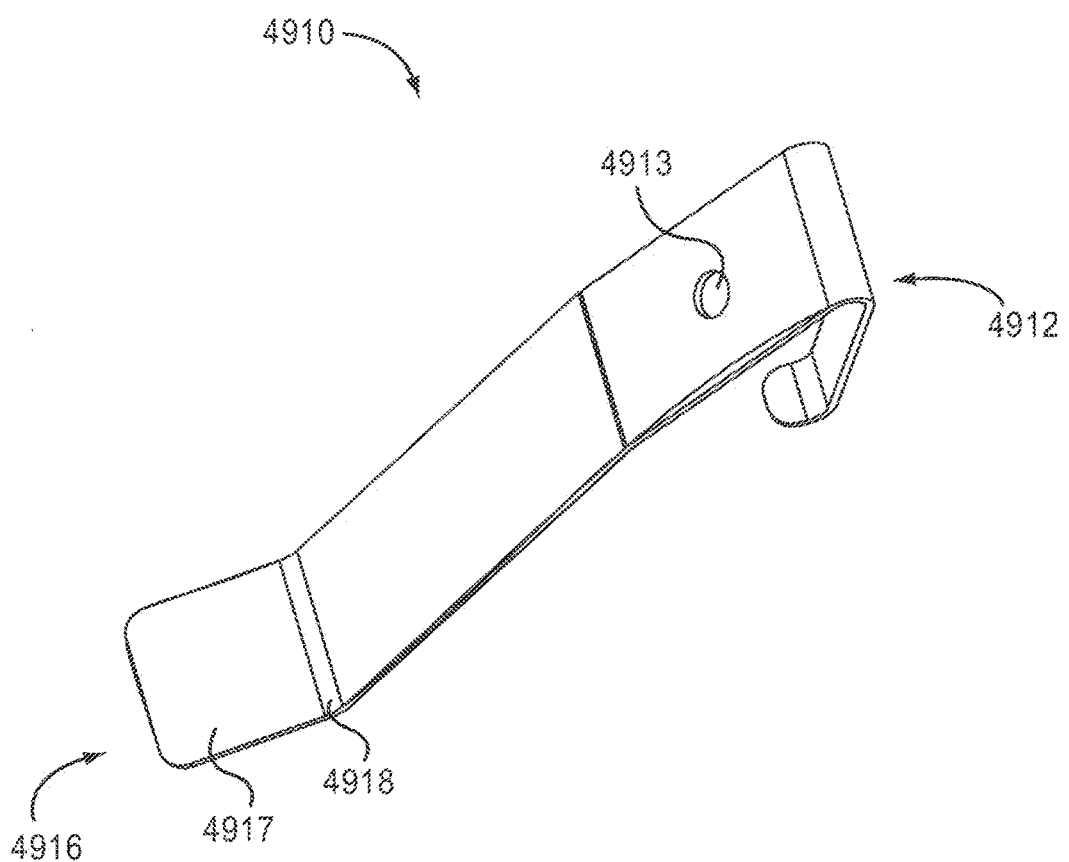
FIG. 18 is a perspective view of a battery clip of the medical injector illustrated in FIG. 13.
Figure 19:
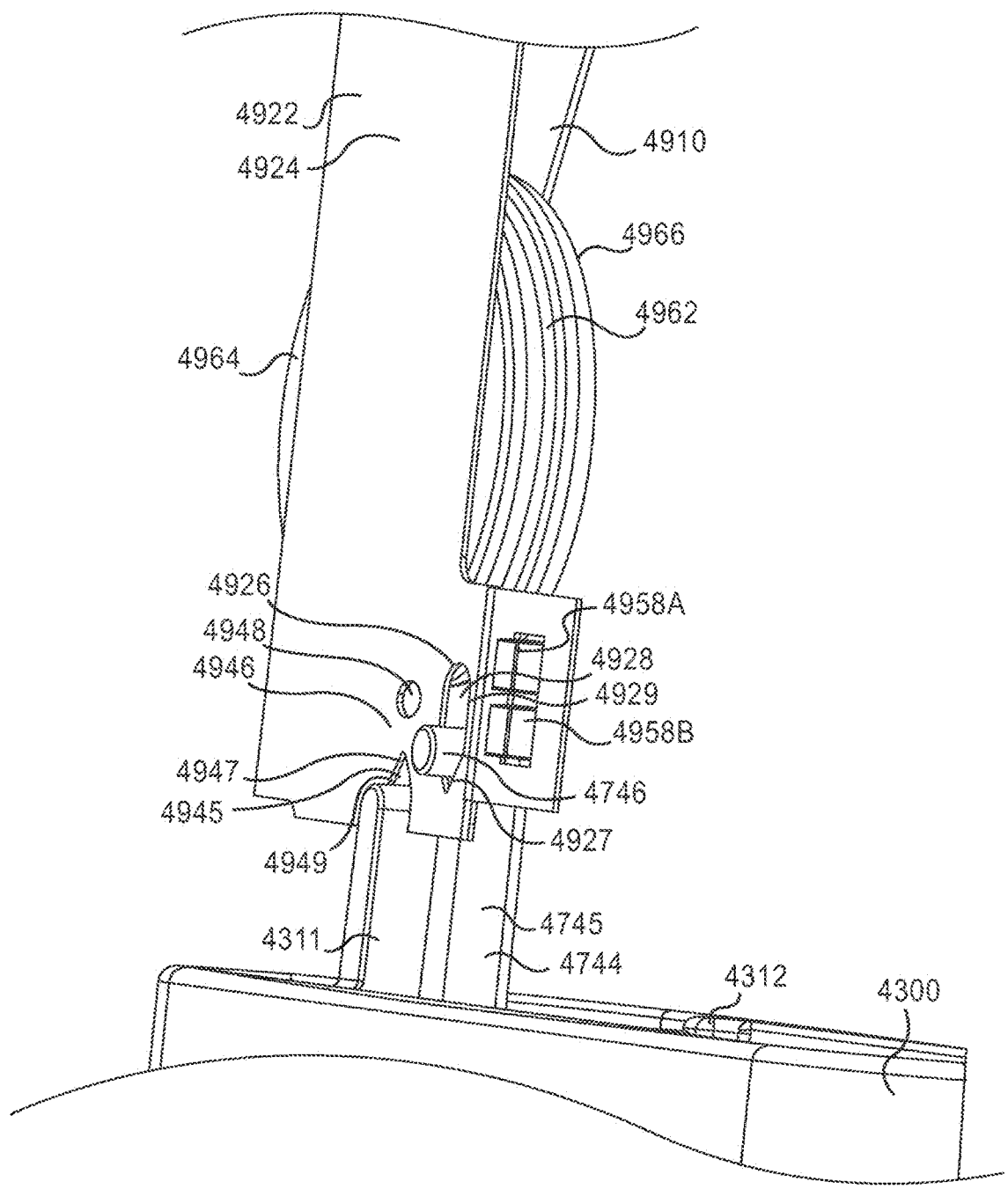
FIG. 19 is a perspective view of a portion of an electronic circuit system of the medical injector illustrated in FIG. 3, in a first configuration.

As shown in FIGS. 16 and 17, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 6). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4300, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or the like.

Figure 21:
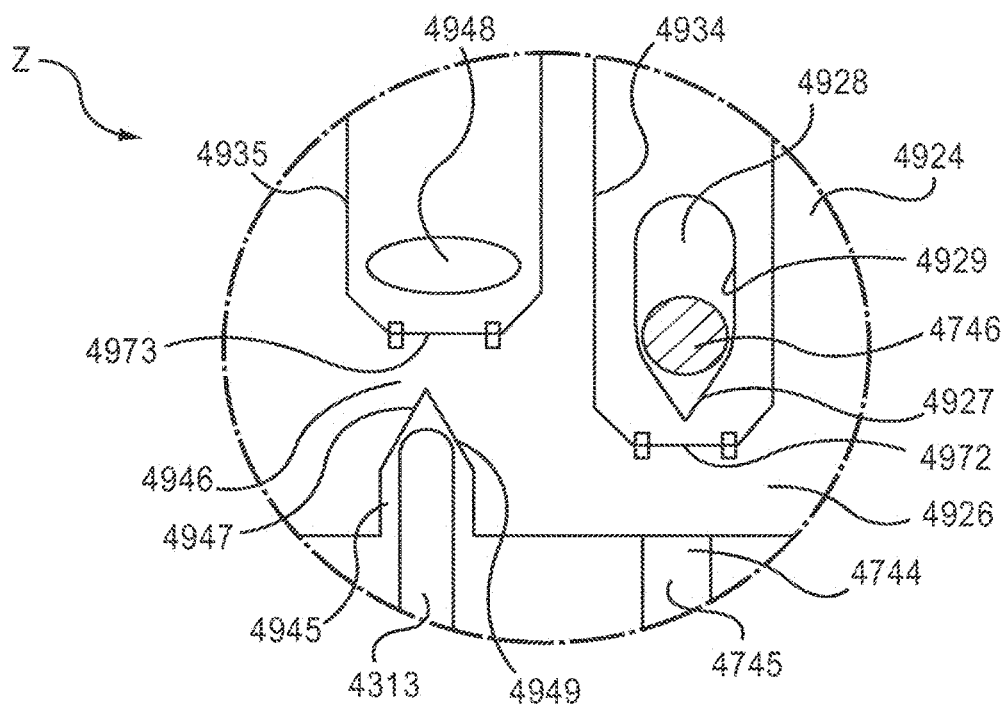
FIGS. 21, 22, and 23 are front views of a portion of the electronic circuit system of the medical injector labeled as Region Z in FIG. 20 in a first configuration, a second configuration, and a third configuration, respectively.
Figure 22:
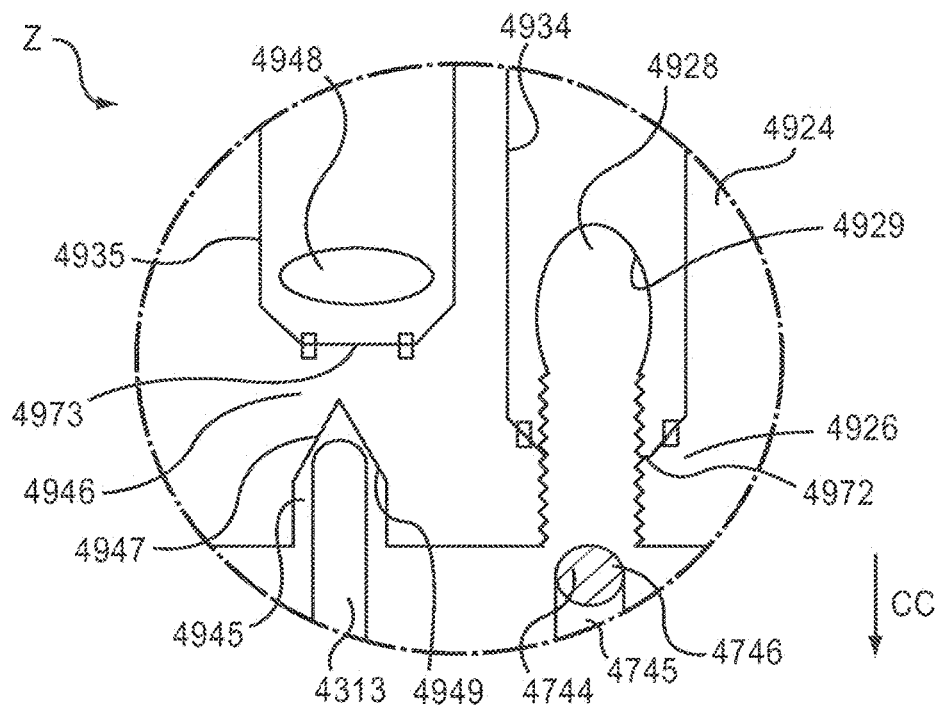
Figure 23:
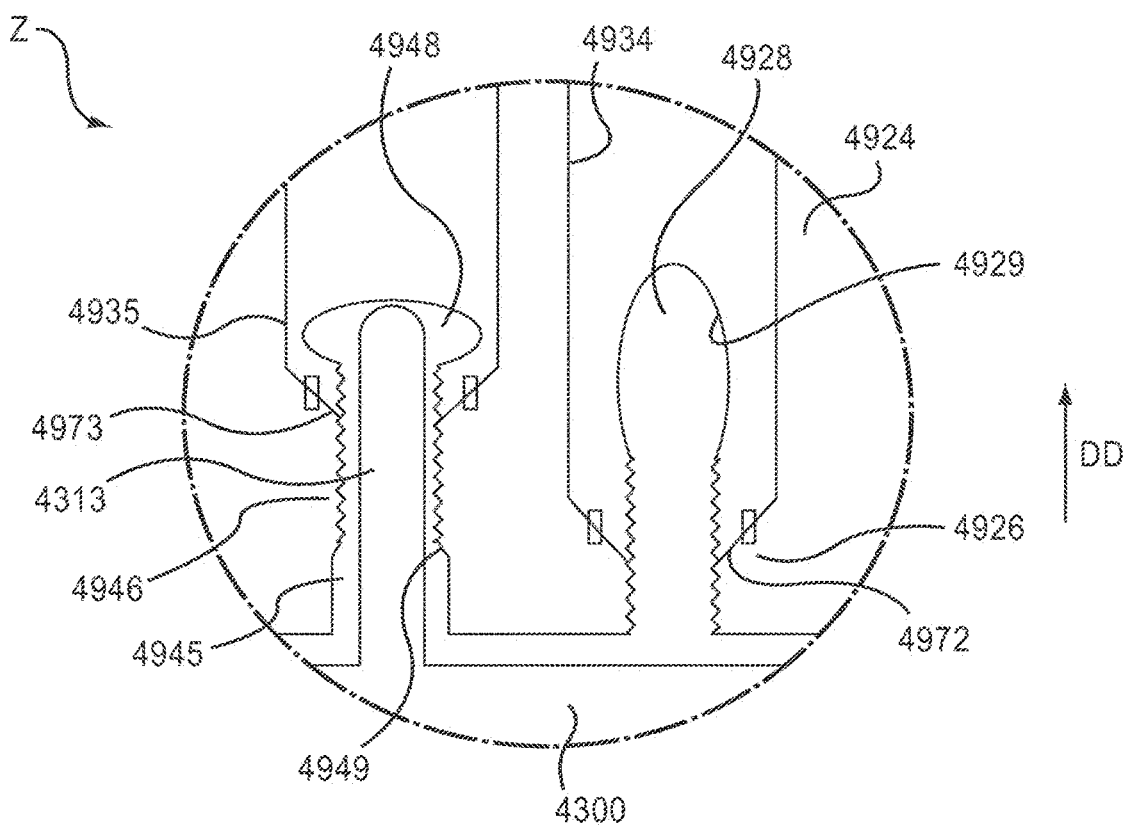

As shown in FIGS. 21-23, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 22.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 21) to a second position (see e.g., FIG. 22), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 22. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 33), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 20-23, the opening 4945 of the second actuation portion 4946 is configured to receive a portion of an actuator 4311 of the base 4300. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4300 is moved in a proximal direction relative to the opening 4945, as shown by the arrow DD in FIG. 23.

The second electrical conductor 4935 includes a second switch 4973 disposed between the opening 4945 and the tear propagation limit aperture 4948, which can be, for example, a frangible portion of the second electrical conductor 4935. In use, when the base 4300 is moved from its first position to its second position (see e.g., FIG. 34), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4300 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

The battery assembly 4962 of the electronic circuit system 4900 comprises two batteries stacked on top of one another. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 18) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4916 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 25) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4916 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown) and/or a communications network (not shown). In this manner, the electronic circuit system 4900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 4900. In some embodiments, for example, the electronic circuit system 4900 can download information associated with a medical injector 4000, such as an expiration date, a recall notice, updated use instructions or the like. Similarly, in some embodiments, the electronic circuit system 4900 can upload compliance information associated with the use of the medical injector 4000 via the network interface device.

Figure 24:
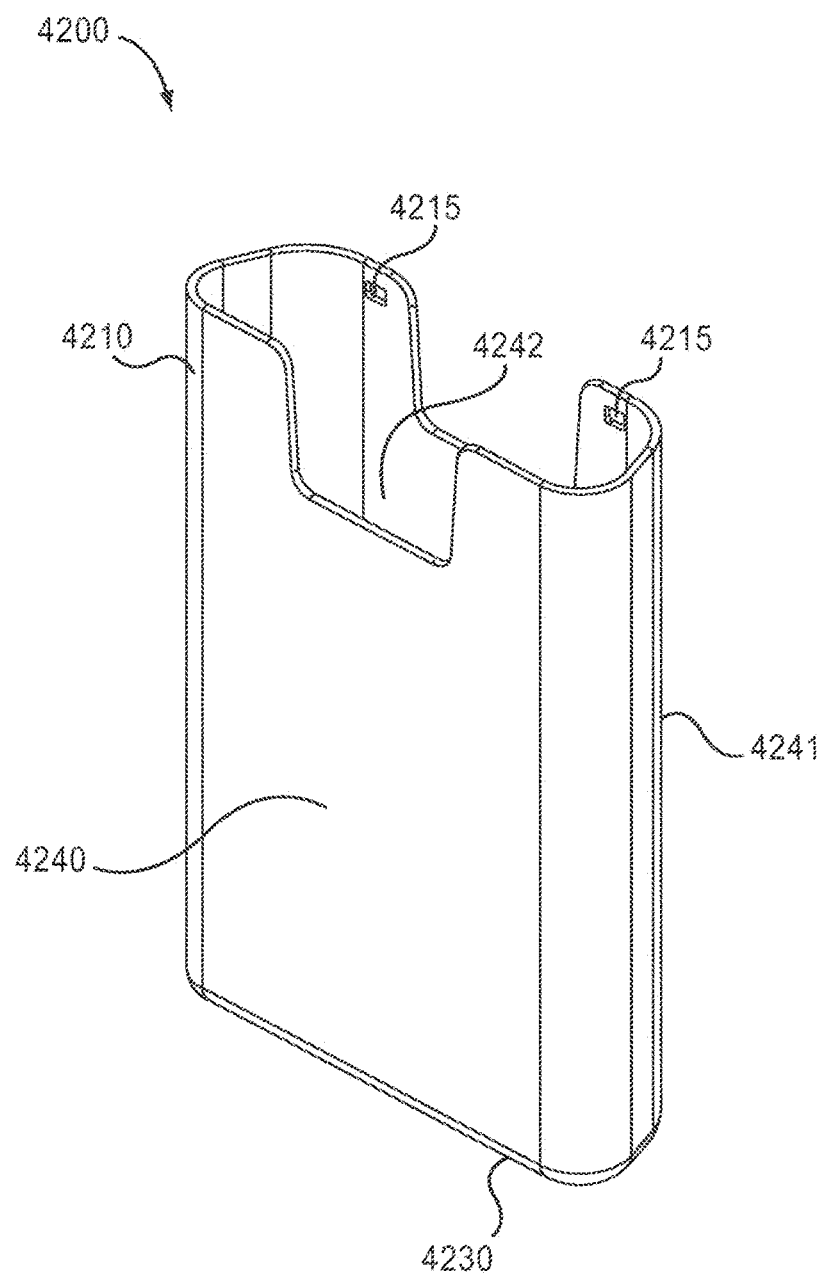
FIGS. 24 and 25 are perspective views of a cover of the medical injector illustrated in FIG. 3.
Figure 25:
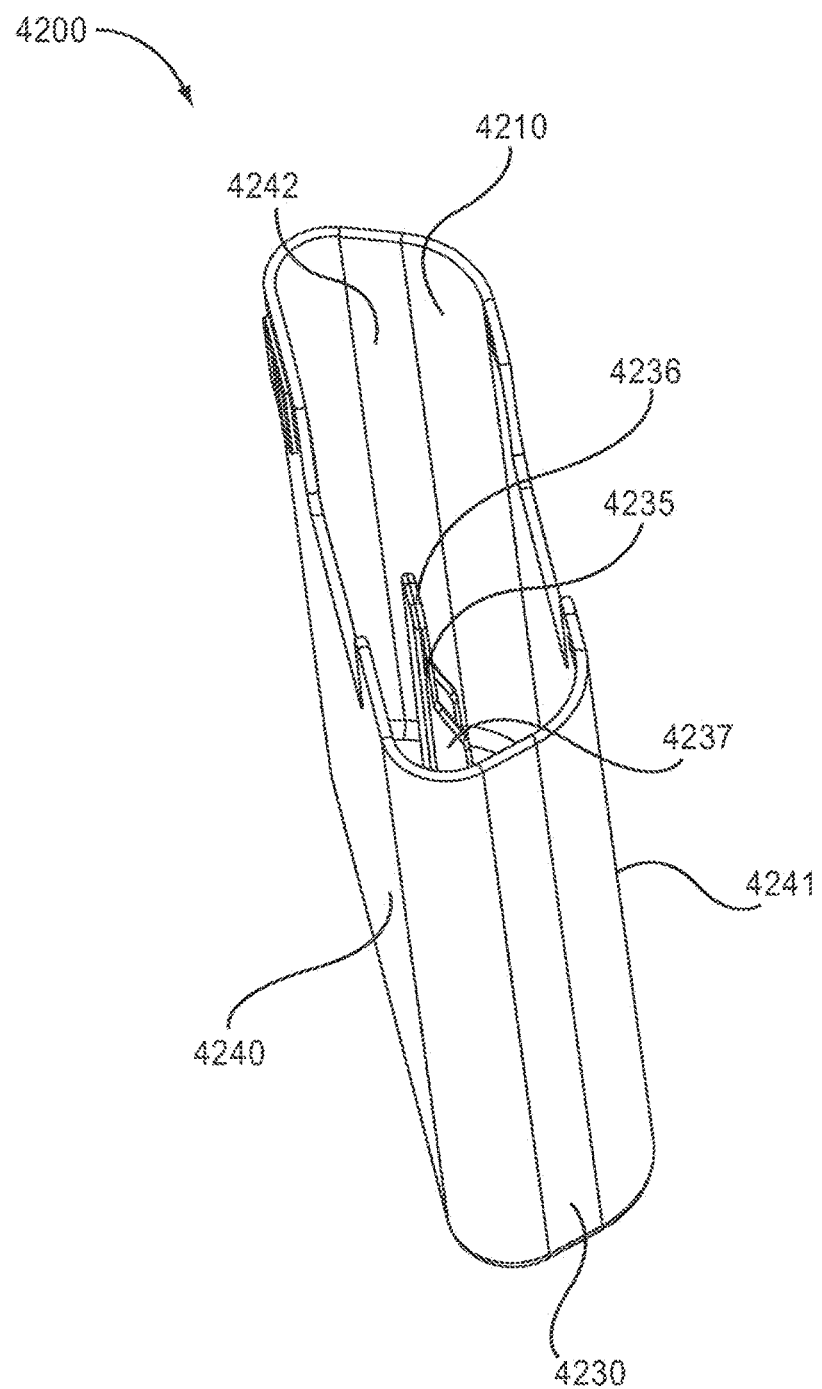
Figure 26:
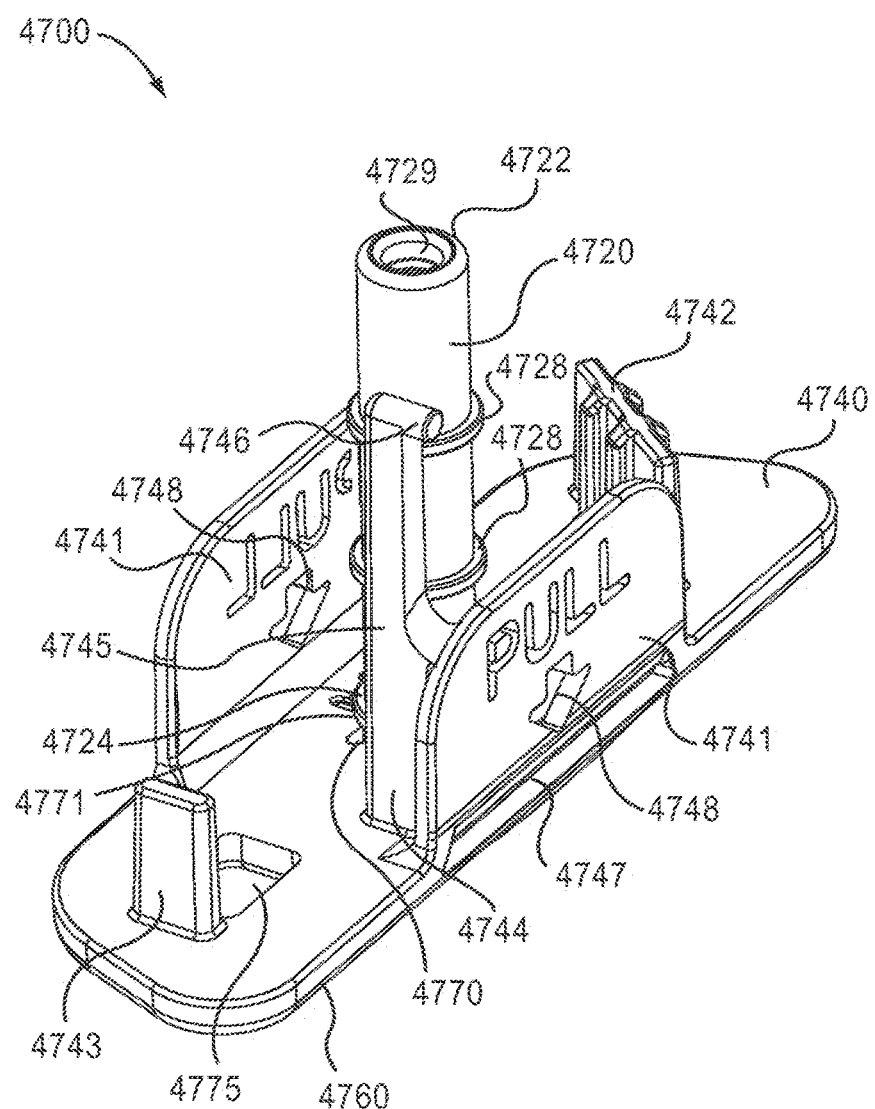
FIG. 26 is a perspective view of a safety lock of the medical injector illustrated in FIG. 3.

FIGS. 24 and 25 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. The proximal end portion 4210 defines apertures 4215 configured to receive the cover retention protrusions 4142 of the housing 4110 (shown in FIGS. 4 and 6). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

The distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 26-29 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4554 defined by the extensions 4552 of the distal end portion 4544 of the release member 4540. Accordingly, the safety lock protrusion 4742 is configured to prevent the extensions 4552 from moving closer to each other, thereby preventing proximal movement of the release member 4540 of the medicament delivery mechanism 4500 and/or delivery of a medicament. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4300 (see e.g., FIG. 30) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 28:
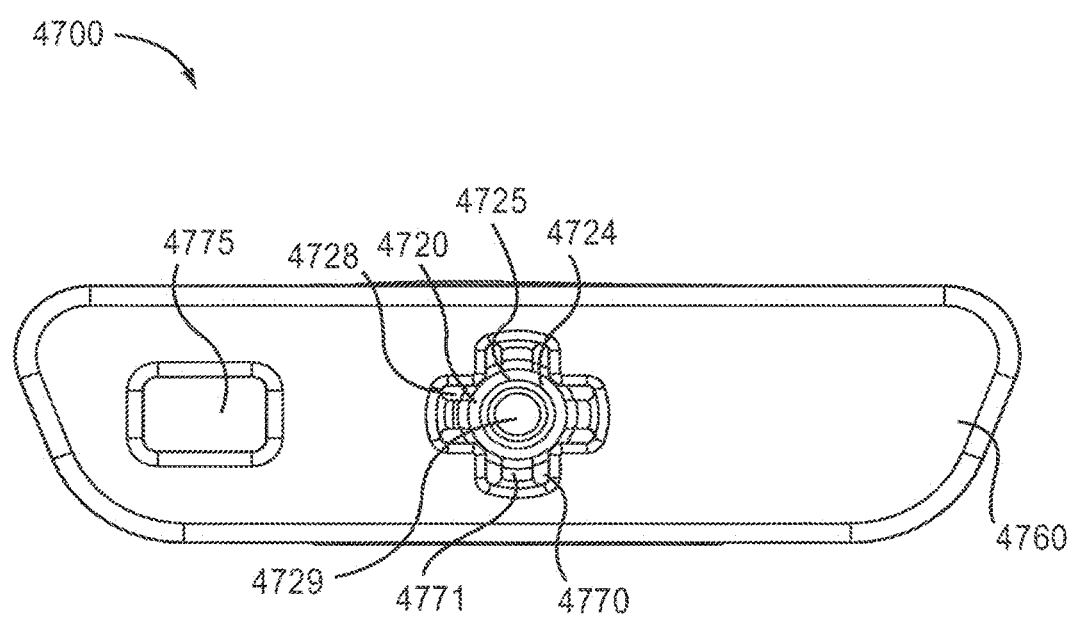
FIG. 28 is a bottom view of the safety lock of the medical injector illustrated in FIG. 26.
Figure 29:
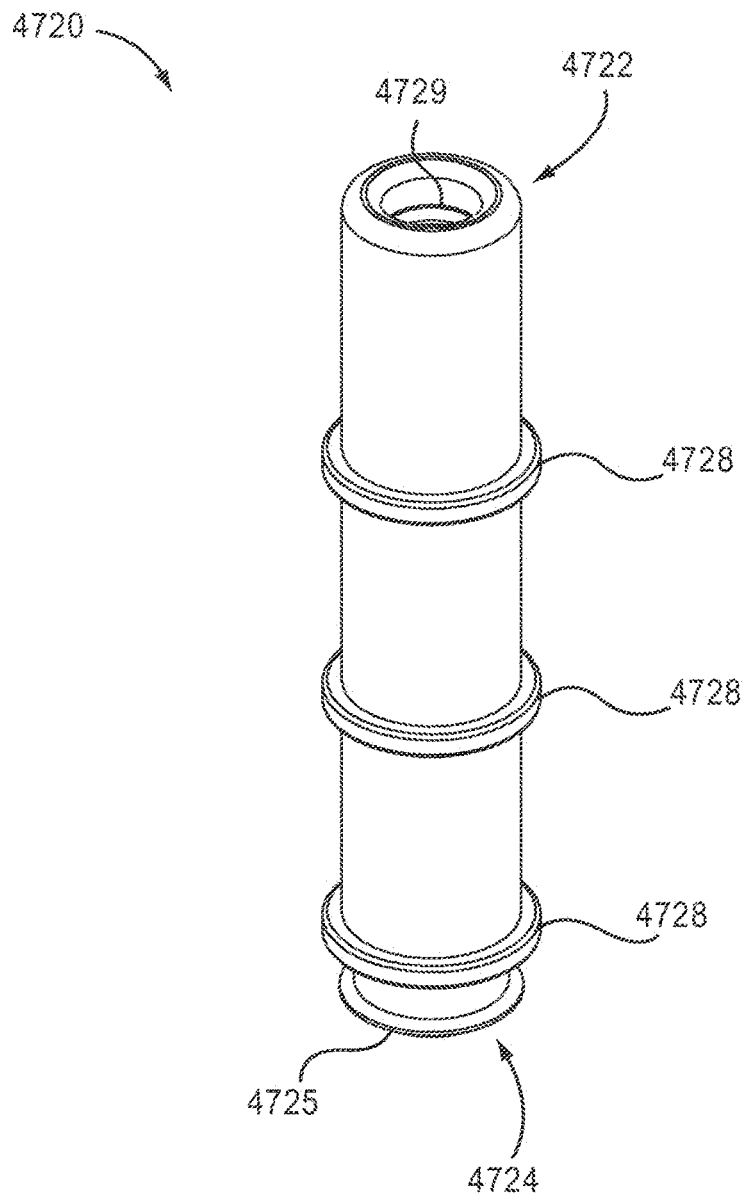
FIG. 29 is a perspective view of a needle sheath of the safety lock of the medical injector illustrated in FIG. 26.

As shown in FIG. 28, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4512. In this manner, the needle sheath 4720 can protect the user from the needle 4512 and/or can keep the needle 4512 sterile before the user uses the medical injector 4000. The proximal end portion 4722 of the needle sheath is configured to contact the distal end portion 4522 of the carrier 4520 of the medicament delivery mechanism 4500.

Figure 33:
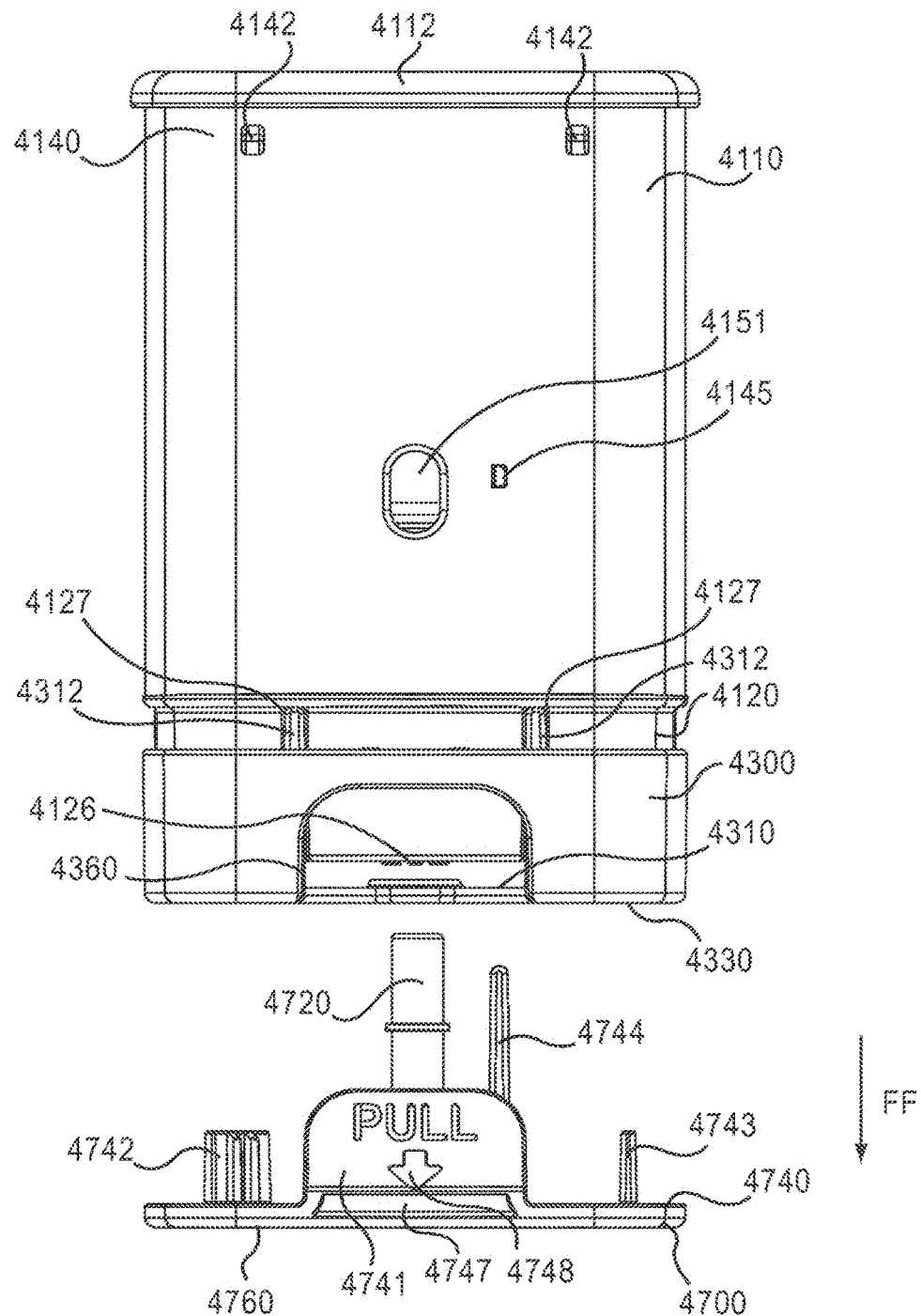
FIG. 33 is a back view of the medical injector illustrated in FIG. 3 in a third configuration.
Figure 34:
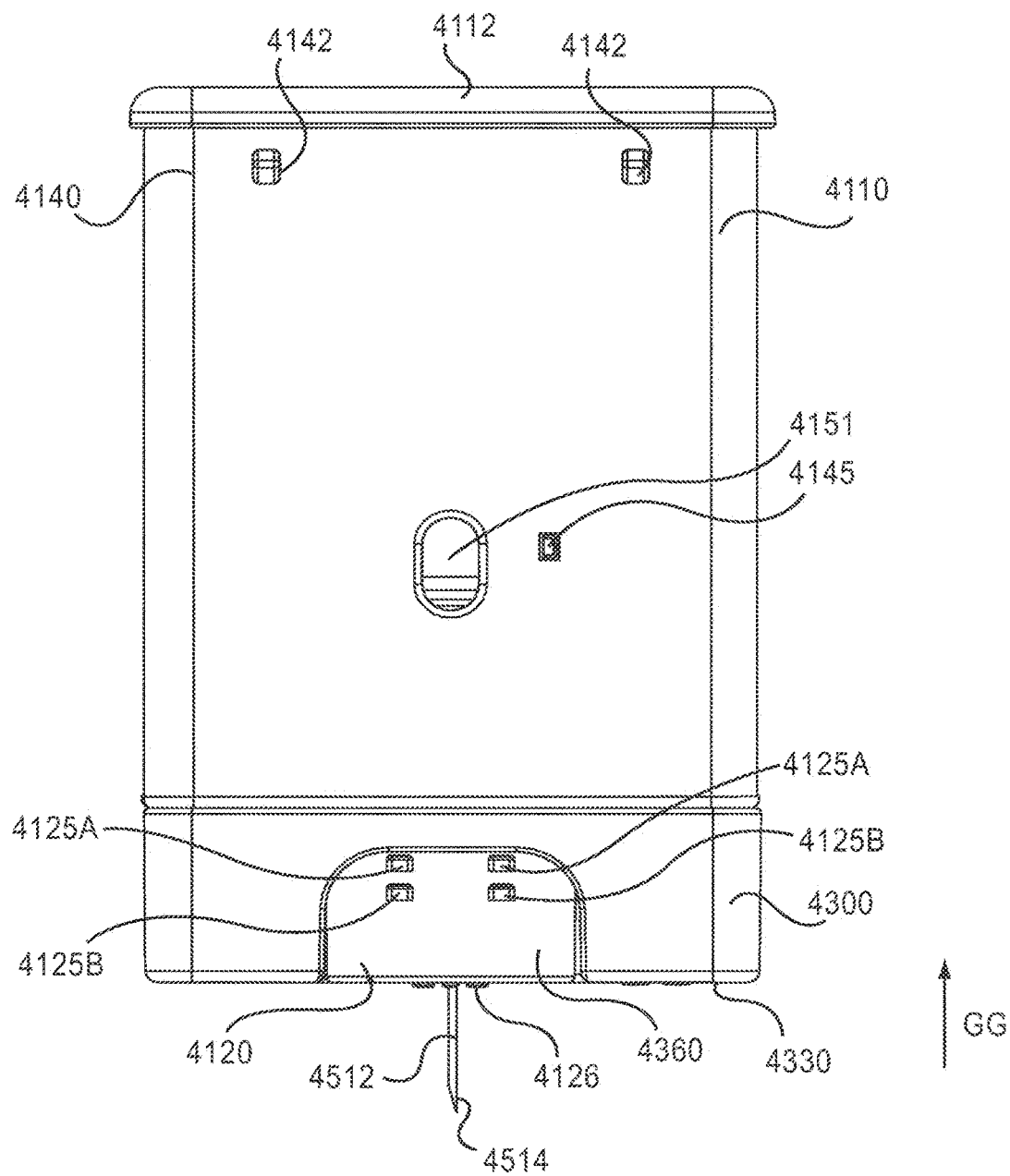
FIG. 34 is a back view of the medical injector illustrated in FIG. 3 in a fourth configuration.

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 33, the needle sheath 4720 is removed from the needle 4512 when the safety lock 4700 is moved in a distal direction with respect to the housing 4110.

Figure 30:
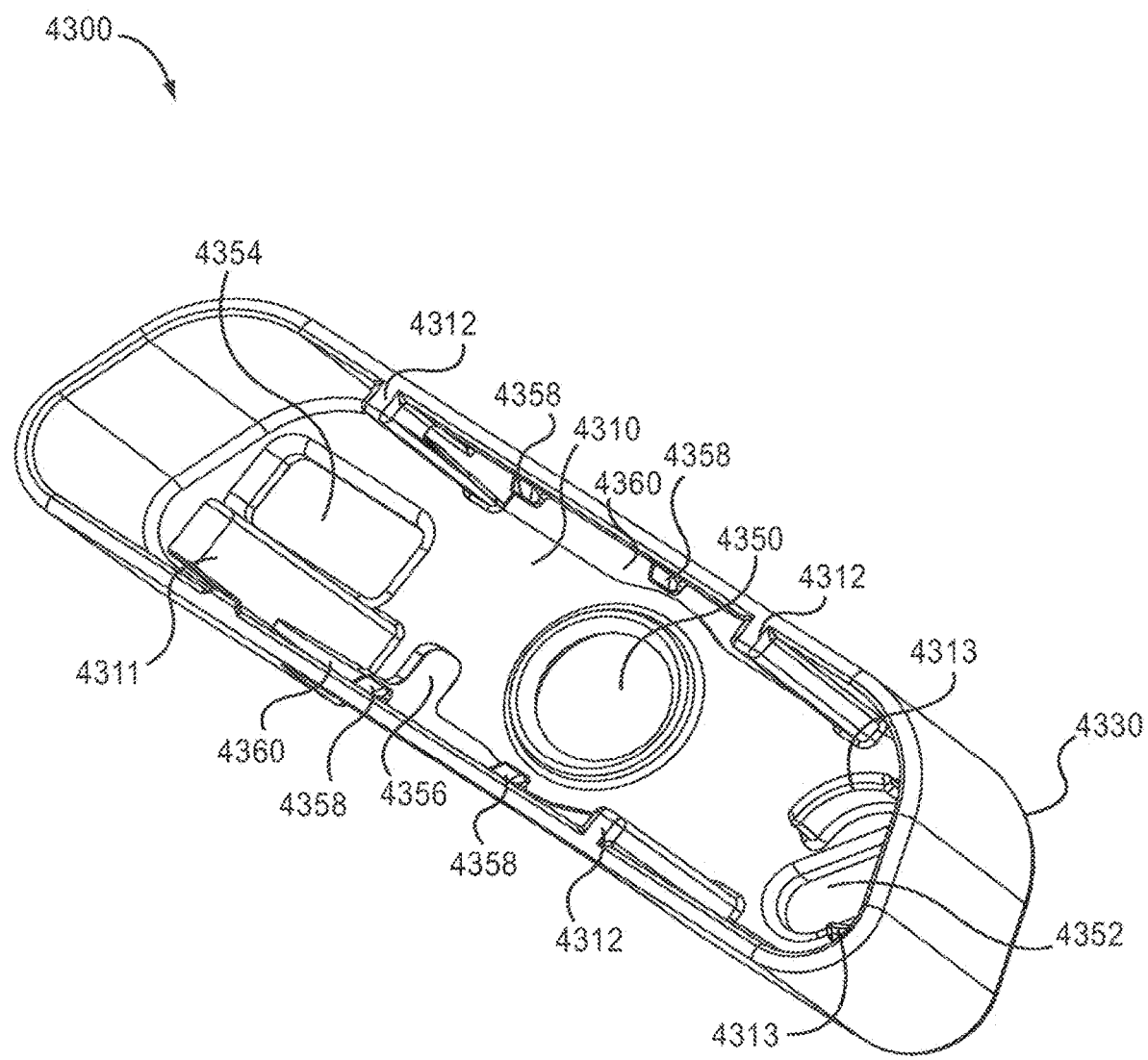
FIG. 30 is a perspective view of a base of the medical injector illustrated in FIG. 3.
Figure 31:
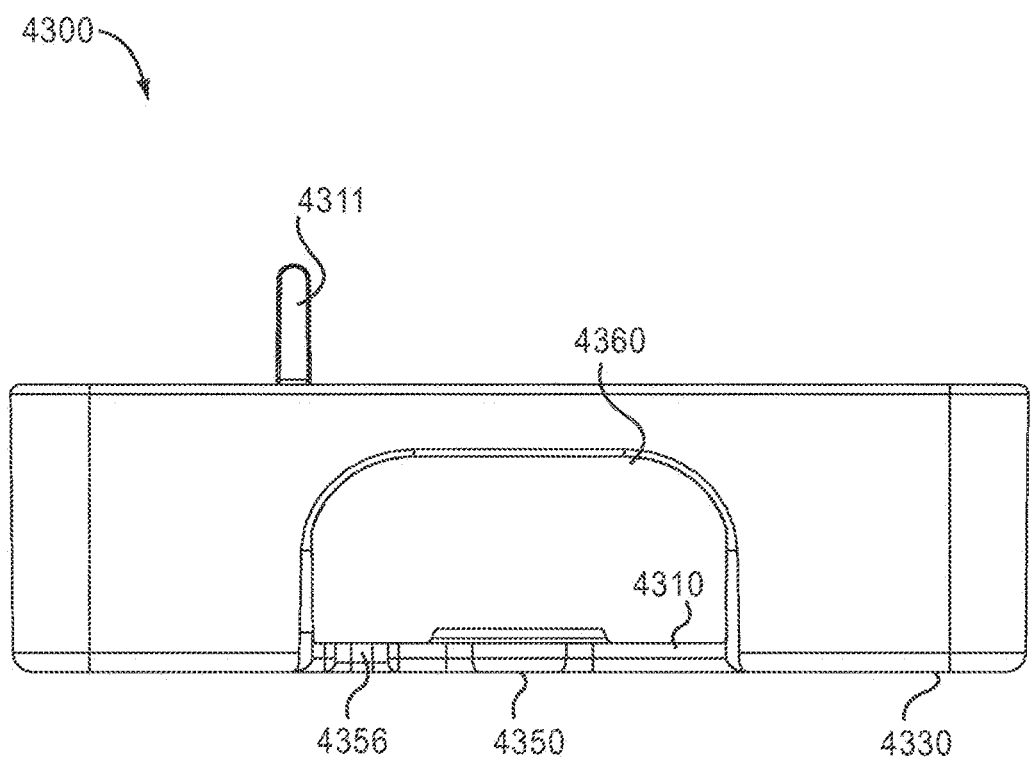
FIG. 31 is a front view of the base of the medical injector illustrated in FIG. 3.

FIGS. 30-31 show the base 4300 of the medical injector 4000. The base 4300 includes a proximal surface 4310, a distal surface 4330 and base connection knobs 4358. The base 4300 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4512 when the medical injector 4000 is actuated. The safety lock protrusion aperture 4352 of the base 4300 receives the safety lock protrusion 4742 of the safety lock 4700. The battery isolation protrusion aperture 4354 of the base 4300 receives the battery isolation protrusion 4235 of the cover 4200 and the stopper 4743 of the safety lock 4700. The safety lock actuator opening 4356 receives the safety lock actuator 4744 of the safety lock

4700. The pull tab openings 4360 are configured to receive the pull tabs 4741 of the safety lock 4700.

The proximal surface 4310 of the base 4300 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4300. The guide members 4312 of the base 4300 are configured to engage and/or slide within the base rail grooves 4127 of the housing 4110, as described above. The protrusions 4313 of the base 4300 are configured to engage the tapered surfaces 4549 of the extensions 4552 of the release member 4540. As described in further detail herein, when the safety lock 4700 is removed and the base 4300 is moved in a proximal direction with respect to the housing 4110, the protrusion 4313 of the base 4300 are configured to move the extensions 4552 of the release member 4540 closer to each other, actuating the medicament delivery mechanism 4500. As described above, the base connection knobs 4358 are configured to engage the base retention recesses 4125A, 4125B in a way that allows proximal movement of the base 4300 but limits distal movement of the base 4300.

Figure 32:
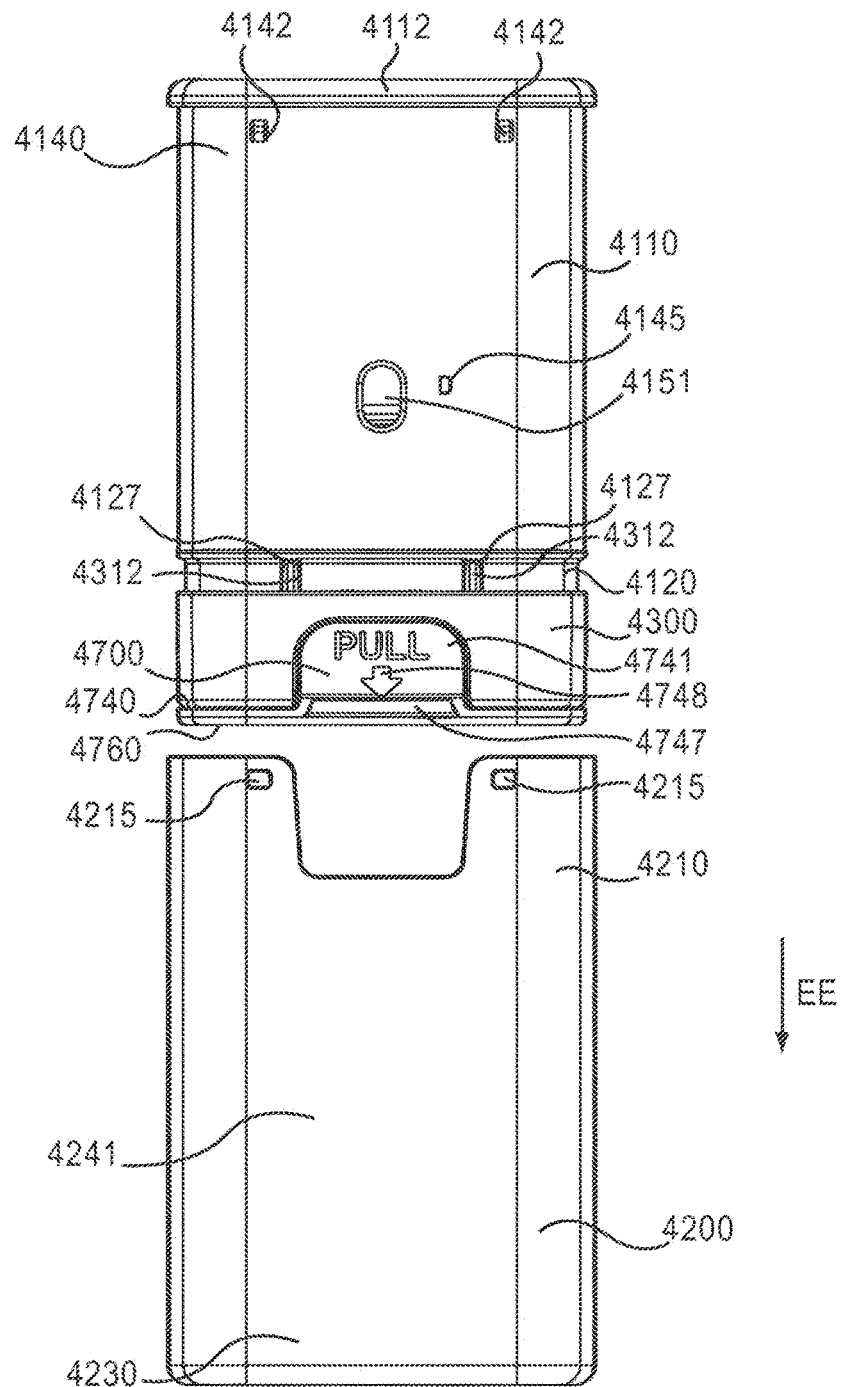
FIG. 32 is a back view of the medical injector illustrated in FIG. 3 in a second configuration.

As shown in FIG. 32, the medical injector 4000 is first enabled by moving the medicament delivery device from a first configuration to a second configuration by moving the cover 4200 from a first position to a second position. The cover 4200 is moved from the first position to the second position by moving it with respect to the housing 4110 in the direction shown by the arrow EE in FIG. 32. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the medicament contained therein. For example, in some embodiments, the electronic circuit system 4900 can output an audible message indicating the type of medicament contained in the medical injector 4000, the expiration date of the medicament, the dosage of the medicament or the like.

As described above, the medical injector 4000 can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4512.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 33. When the safety lock 4700 is moved from the first position to the second position, the safety lock protrusion 4742 is removed from between the extensions 4552 of the release member 4540, thereby enabling the medicament delivery member 4500. Moreover, as shown in FIGS. 21 and 22, when the safety lock 4700 is moved from the housing 4110, the actuator 4744 of the safety lock 4700 moves in the direction CC as shown in FIG. 22, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "The medical injector is now enabled." The electronic circuit system 4900 can also simultaneously output an electronic signal to one and/or both of the LEDs 4958A, 4958B, thereby causing one and/or both of the LEDs 4958A, 4958B to stop flashing, change color or the like.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described above, in other embodiments, the medical injector 4000 can have a network interface device (not shown) configured to operatively connect the electronic circuit system 4900 to a remote device (not shown) and/or a communications network (not shown). In this manner, the electronic circuit system 4900 can send a wireless signal notifying a remote device that the safety lock 4700 of the medical injector 4000 has been removed and that the medical injector 4000 has been armed.

After the safety lock 4700 is moved from the first position to the second position, the medical injector 4000 can be moved from the third configuration to a fourth configuration by moving the base 4300 from a first position to a second position. The base 4300 is moved from its first position to its second position by placing the medical injector 4000 against the body of the patient and moving the base 4300 with respect to the housing 4110 in the direction shown by the arrow GG in FIG. 34. Moving the base 4300 from the first position to the second position causes the protrusions 4313 on the proximal surface 4310 of the base 4300 to engage the tapered surfaces 4549 of the extensions 4552 of the release member 4540, causing the release member 4540 to actuate the medicament delivery mechanism 4500 and deliver a medicament to a body of a patient.

When the base 4300 is moved from the first position to the second position, the medicament delivery mechanism 4500 is actuated such that the puncturer 4541 of the release member 4540 is brought in contact with and/or punctures the frangible seal 4573 of the gas container 4570. In some embodiments, the movement of the release member 4540 can be caused by a spring (not shown in FIG. 12). After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157. When the carrier 4520 moves distally within the medicament cavity 4157, the carrier 4520 and the medicament container 4560 are in a first configuration. Accordingly, as described above, the medicament container 4560 is connected to the carrier 4520 by a "snap fit" connection. In this manner, the medicament container 4560 and the needle 4512 contemporaneously move with movable member 4530 and/or the carrier 4520 in a distal direction. As described above, the proximal end portion 4516 of the needle 4512 is connected to the distal end portion 4522 of the carrier 4520 and is spaced from the seal 4523 of the medicament container 4560 when the carrier 4520 is in its first configuration. Said another way, the medicament container 4560 and the needle 4512 do not define a medicament delivery path when the carrier 4520 is in the first configuration. The movement of the needle 4512 in a distal direction causes the proximal end portion 4516 of the needle 4512 to exit the housing 4110 and enter the body of a patient prior to administering a medicament.

After the carrier 4520 and/or the needle 4512 have moved within the medicament cavity 4157 a predetermined distance, the carrier 4520 and the medicament container 4560 are moved from the first configuration to a second configuration. In the second configuration of the carrier 4520, the medicament container 4560 is released from the "snap-fit" allowing the medicament container 4560 and the movable member 4530 to continue to move in a distal direction relative to the carrier 4520. Said another way, the medicament container 4560 is configured to slidably move within the carrier 4520 when the carrier is moved from the first configuration to the second configuration. As the medicament container 4560 continues to move within the carrier 4520, the proximal end portion 4516 of the needle 4512 contacts and punctures the seal 4523 of the medicament container 4560. This allows the medicament contained in the medicament container 4560 to flow into the lumen (not shown) defined by the needle 4512, thereby defining a medicament delivery path.

As the medicament container 4560 contacts the distal end of the carrier 4520, the medicament container 4560 stops moving within the carrier 4520 while the movable member 4530 continues to move in a distal direction. This causes the piston portion 4534 of the movable member 4530 to sealingly slide and/or move within the medicament container 4560 containing a liquid medicament. As the piston portion 4534 of the movable member 4530 sealingly slides and/or moves within the medicament container 4560, the piston portion 4534 generates a pressure upon the medicament contained within the medicament container 4560, thereby allowing at least a portion of the medicament to flow out of the medicament container 4560 and into the lumen defined by the needle 4512. The medicament is delivered to a body of a user via the medicament delivery path defined by the medicament container 4560 and the needle 4512.

As described above, the actuator 4538 of the base 4300 actuates the electronic circuit 4900 to trigger a predetermined output or sequence of outputs when the base 4520 is moved from its first position to its second position (see, e.g., FIGS. 19-23). When the actuator 4538 is moved in a proximal direction relative to the opening 4945, as shown by the arrow DD in FIG. 23, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4538 can be configured such that the base 4500 and/or the actuator 4538 must move a predetermined distance before the actuator 4538 engages the boundary 4949 of the opening 4945. For example, in some embodiments, the actuator 4538 must move approximately 0.200 inches before the actuator 4538 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

FIG. 35 depicts a medicament delivery device 100 (e.g., any suitable device, such as the medicament injectors and/or simulated devices described above with reference to FIGS. 1-35), an adapter 120 and a monitor device 150. The medicament delivery device 100 can be paired with and/or cooperatively function with the adapter 120 and/or the monitor device 150 to "page," locate and/or otherwise assist a patient and/or third party in determining the identity and/or location of the medicament delivery device 100. The monitor device 150 can be any suitable device that is operable to send a signal to the adapter 120 causing the adapter 120 to emit a sound or other signal. In this manner, the monitor device 150 and the adapter 120 can cooperatively function to alert the user to the location of the medicament delivery device 100. In other embodiments, according to the methods described herein, the monitor 150 can produce an alarm (e.g., an audible alarm, a visual alarm or a vibratory alarm) to indicate a loss of communications with the adapter 120, thus alerting the user to the possibility that the user may be forgetting to carry the adapter 120.

The adapter 120 can be coupled to the medicament delivery device 100. The adapter 120 can, for example, be a sleeve, case, insert, attachment, and/or docking station coupled to the medicament delivery device 100, a housing of the medicament delivery device 100 (such as the housing 4100 described above) and/or electronic circuitry of the medicament delivery device 100 (such as the electronic circuit system 4900 described above). In some embodiments, the adapter 120 can be removably coupled to and substantially surround a portion of the medicament delivery device 100, similar to the covers 14200 and/or 4200 shown and described herein. In other embodiments, an adapter 120 can be attached to an outer surface of a medicament delivery device 100 without surrounding or covering a significant portion of the medicament delivery device. In yet other embodiments, an adapter 120 can be inserted completely or partially into an inside chamber of a medicament delivery device. In yet other embodiments, an adapter 120 can be fixedly coupled to an outer surface of a medicament delivery device. Although shown as being a separate component, in some embodiments, an adapter 120 can be integral with the medicament delivery device 100. Said another, in some embodiments, the function of the adapter 120 described below can be included within a housing and/or electronic circuit system of the medicament delivery device 100.

The adapter 120 can include a radio 122 (also referred to as a receiver, transmitter and/or transceiver) and/or an audible output device 124. The radio 122 of the adapter 120 can be operable to send signals to, and/or receive signals from the monitor device 150 in accordance with any of the methods described herein. For example, although not shown in FIG. 35, in some embodiments, the adapter 120 can include a processor, a memory, a communication module, a leash module and/or a use module, as describe above with respect to FIG. 1.

The audible output device 124 of the adapter 120 can be operable to emit an audible output, such as a tone and/or recorded speech instructions. As discussed in further detail herein, in some embodiments, the adapter 120 can include a sensor (or switch) 126 operable to detect an event associated with the medicament delivery device 100. Such events can include, for example, when the medicament delivery device 100 is used and/or is prepared for use. In this manner, the sensor 126 can detect the status and/or usage history of the medicament delivery device 100. For example, in some embodiments, the adapter 120 can be a sleeve or cover (similar to the cover 4200 shown and described above) that is removed from the medicament delivery device 100 prior to use. In such embodiments, the sensor and/or switch 126 can be operable to detect the removal the adapter 120 from the medicament delivery device 100 and can cause the adapter 120 to send a signal (e.g., to the monitor device 150) via the radio 122 and/or to emit an audible output via the audible output device 124. In some embodiments, as described herein, the adapter 120 can adjust a communication mode, a communication interval, and/or a power level associated with a wireless communication between the adapter 120 and the monitor device 150. In this manner, the adapter 120 can be configured to conserve power resources when the medicament delivery device 100 is coupled to and/or disposed within the adapter (i.e., the medicament delivery device 100 is otherwise not armed for and/or likely to be used).

In some embodiments, the adapter 120 can include an electronic circuit system, similar to the electronic circuit system 4900 shown and described above, to contain, include and/or provide interconnection between the components discussed herein (e.g., the radio 122, the audible output device 124 and the sensor 126). For example, in some embodiments, the adapter 120 can include an electronic circuit system having one or more switches of the type disclosed above with reference to the electronic circuit system 4900.

Although described as producing an audible output, in other embodiments, any of the devices and/or systems described herein can produce a human perceivable signal, such as audible, visual, vibratory and/or haptic alerts. In other embodiments, the signal can be a radio signal, IR signal and/or signals otherwise not human perceivable. An embodiment can include both human perceivable and signals that are not human perceivable. For example, in some embodiments, the removal of the medicament delivery device 100 from the adapter 120 can place a power source (not shown) of the medicament delivery device 100 in electrical communication with an electrical circuit. When "powered on," the medicament delivery device can produce a signature pressure wave output (either audible or inaudible) that is detected by microphone on the adapter. As described in more detail herein, in response to the receipt of this signal, the adapter 120 can adjust a characteristic of the wireless communications therefrom. The medicament delivery device 100 can further be configured to produce a second pressure wave (e.g., an audible output) to provide instructions to the user, as described above.

The monitor device 150 can include a radio 152, an audible output device 154, and/or one or more sensors 156, and can be operable to monitor the user via the sensor 156, communicate with the adapter 120, and/or provide an audible output. The monitor device 150 need not include all of the components shown in FIG. 35 nor perform all of the functions described herein. For example, in some embodiments, a locator according to an embodiment can be devoid of a sensor 156. The monitor device 150 can be operable to be easily located, identified and/or readily accessible by the user and/or third parties. For example, the monitor device 150 can be a bracelet, a necklace, a keychain fob, a watch, a ring, an adhesive patch, a cellular phone or other personal electronic device, and/or any other suitable object. The monitor device 150 can be a piece of jewelry and/or integrated into a piece of jewelry. In some embodiments, however, the monitor device 150 can be inconspicuous, so as to not draw attention to the user. For example, in some embodiments, the monitor device 150 can be similar to and/or incorporated within an article that is inconspicuous. For example, in some embodiments, the monitor device 150 can be located on an inner layer of clothing, incorporated or manufactured as a part of the clothing, incorporated into a common accessory, fabricated to resemble a standard key fob, or the like. In other embodiments, the monitor device 150 can be conspicuous such that, in the event of a medical emergency, bystanders can readily identify and/or locate the monitor device 150, which can, in turn, allow the bystander to identify and/or locate the medicament delivery device 100. In yet other embodiments the monitor device 150 can be configured to transition between an inconspicuous configuration and a conspicuous configuration. Similarly, stated, in some embodiments the monitor device 150 can be inconspicuous in a standby state, e.g., when there is no medical emergency, and conspicuous in an active state, e.g., when there is a medical emergency, and/or when activated by the user. For example, the monitor device 150 can emit an alert, such as an alarm or recorded instruction via the speaker 154 and/or can have flashing lights, vibration (haptic output) and/or any other suitable mechanism to draw attention when the monitor device 150 is in the active (or conspicuous) state. Similarly stated, the monitor device 150 can include any suitable mechanism for changing between a first configuration and a second configuration in response to an event (e.g., a medical emergency, a notification received from a doctor, pharmacy or the like).

In some embodiments, the monitor device 150 can be a computing device similar to the computing device 1510 described above. In such embodiments the computing device (e.g., a smart phone) can be adapted to perform the functions of the monitor device 150 as described herein. For example, a cellular telephone can execute an application operable to monitor the user via the sensor 156, communicate with the adapter 120, and/or provide an audible output via the audible output device 154.

The monitor device 150 can communicate with the adapter 120 via the radio 152. The communication between the monitor device 150 and the adapter 120 can be initiated by any suitable method, including manual initiation and/or automatic initiation. In some embodiments, the communication between the monitor device 150 and the adapter 120 can be initiated by pushing a button. In other embodiments, the monitor device 150 can be activated by a signal from the sensor 156 and/or the sensor 126. In this manner, for example, the communication can be initiated when the sensor 156 detects a significant change in the user's vital signs. In some embodiments, the monitor device 150 and the adapter 120 can establish and maintain a substantially continuous and/or periodically verified communications link. If the link is severed, e.g., the monitor device 150 moves out of communications range from the adapter 120, the monitor device 150 and/or the adapter 120 can emit a signal, such as an audible or visual alarm, to alert the user to the broken connection. Such an embodiment could reduce the likelihood of the user forgetting to carry the adapter 120 and/or the monitor device 150 together.

In some embodiments, as described herein, characteristics of the communication between the monitor device 150 and the adapter 120 can be modified in response to a signal received from the sensor 156, the sensor 126, a manual entry or the like.

In use, the monitor device 150 and the adapter 120, can cooperatively function to aid the user in identifying and/or locating the adapter 120, which can, in turn, aid the user in locating the medicament delivery device 100. For example, when actuated the monitor device 150 can send a signal, e.g., via the radio 152, to the adapter 120 to cause the adapter 120 and/or the medicament delivery device 100 to emit a human-perceivable signal, such as an audible or visual alert. The human perceivable signal can be operable to draw the user's attention to the adapter 120.

In some embodiments, the monitor device 150 and/or the adapter 120 can be operable to calculate and/or report a distance between and/or a direction of the locator relative to the adapter 120. For example, the adapter 120 and/or the monitor device 150 can be operable to calculate their respective positions (e.g., absolute positions or position relative to each other), for example based on the strength and/or direction of a radio signal, triangulation, trilateration, GPS, or any other suitable means. In such embodiments, the monitor device 150 can direct the user to the location of the adapter 120 based on the calculation of the relative positions. This arrangement can allow, for example, the monitor device 150 and/or the adapter 120 to produce a dynamic alert based on the change in position of the monitor device 150 and the adapter 120. For example, in some embodiments, the adapter 120 can emit a pulsed audible output when communication with the monitor device 150 is established. Based on the calculated relative position and/or distance between the adapter 120 and the monitor device 150, an intensity, frequency and/or magnitude of the audible output can change. In particular, the frequency and/or magnitude of the audible output (e.g., a beep) can get higher and/or louder as the monitor device 150 is moved closer to the adapter 120 (and/or the medicament delivery device 100). In this manner the adapter 120 and/or the monitor device 150 can include and/or operate as a proximity detector.

In some instances, a person requiring administration of a medicament, "a patient," may not be the person administering the delivery of the medicament (referred to herein as "a user"). For example, the medicament contained in the medicament delivery device 100 may be intended for administration in a medical emergency, during which the patient may be incapacitated. For example, in some embodiments, the medicament delivery device (e.g., the medicament delivery device described above with reference to FIGS. 3-34) may be intended to deliver epinephrine in the event of an anaphylactic crisis, or to deliver naloxone in the event of an opioid overdose, or any other potentially life-saving medication. In such an emergency, the patient may not be able to operate the medicament delivery device 100. Accordingly, as described herein, in such circumstances, the monitor 150 can detect the presence of a medical condition (e.g., via sensor 156), can produce an instruction, alert or other notification (e.g., via the audible output device 154), and can either prompt the third party care giver to initiate communication with the adapter 120 or automatically establish such communications. For example, in some embodiments the sensor 156 can be operable to detect physiological parameters associated with the patient, such as heart rate/pulse, respiratory rate, blood sugar, blood oxygen, blood or tissue lactate level, blood or tissue ketone level, an immune response, acceleration (e.g., associated with a fall), brain activity, and/or the like. In the event the monitor device 150 detects an abnormal condition that may require medical attention, the monitor device 150 can emit a signal to be received by the adapter 120, such that the adapter can provide an indication, instruction or the like as discussed herein.

In some embodiments, the monitor device 150 and any of the monitoring devices, adapters and/or locators described herein can be configured to send a wireless signal in response to the detection of an abnormal condition or potential emergency. In particular, in some embodiments, the monitor device 150 and/or any device operably coupled thereto can automatically dial an emergency number such as, for example, 911 (emergency dispatcher), and/or send information associated with the location of the device and/or the end user location through GPS satellite positioning or network based positioning (using cell phone towers). In this manner, the adapter 120, the monitor device 150 and a remote device (not shown in FIG. 35) can form a network, as described above with reference to FIG. 1.

In other embodiments, the monitor device 150 can be triggered by a non-emergency event. For example, in some embodiments, the sensor 156 can be configured to measure environmental conditions or the like (e.g., temperature, humidity, presence of certain allergens, etc.) and establish communications with the adapter 120 based on such measurements. For example, in some embodiments, the medicament delivery device 100 can be an inhaler, and the monitor device 150 can measure and analyze environmental data such that the monitor device 150 can alert the patient and/or user to use the inhaler.

Although the monitor device 150 is shown as including a sensor 156, in other embodiments, the monitor device 150 need not include any sensors. For example, in some embodiments, the monitor device 150 be conspicuous and/or include a conspicuous label such that a third party will recognize the monitor device 150, and can then manually initiate communication with the adapter 120 (e.g., by pressing a switch, similar to actuating a "page" feature). For example, in some embodiments, the monitor device 150 can include a conspicuous start button that, when pushed, results in a message being produced by the monitor device 150. The message can state, for example, "THE PERSON WEARING THIS IDENTIFIER IS CARRYING AN AUTO-INJECTOR TO TREAT SYMPTOMS RELATED TO . . . IF THIS PERSON IS EXHIBITING SUCH SYMPTOMS, PLEASE LOCATE THE AUTO-INJECTOR, WHICH IS NOW BEEPING, AND FOLLOW THE NEXT SET OF INSTRUCTIONS."

Although the adapter 120 is shown as being a separate component that is coupled to a medicament delivery device 100 (e.g., such a sleeve, and adapter, or the like), in other embodiments, the functionality of the adapter 120 can be incorporated into the medicament delivery device 100, such that the monitor device 150 communicates and/or interacts directly with the medicament delivery device 100 to perform the functions described herein.

Figure 36:
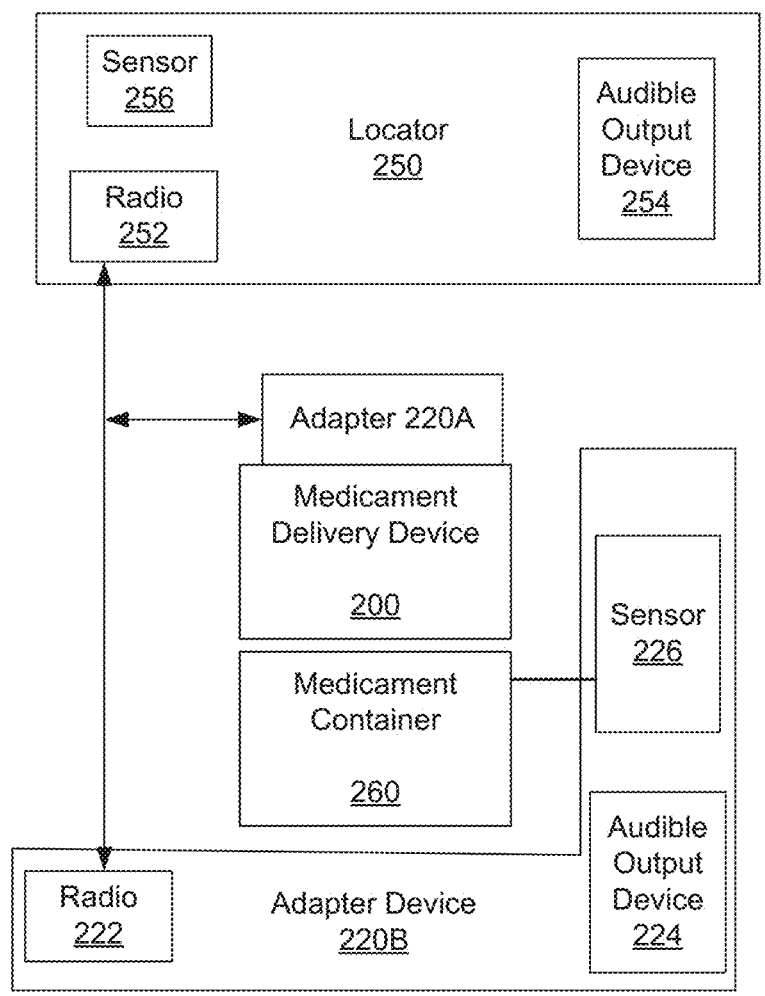
FIG. 36 is a schematic diagram of a locator device, a medicament delivery device and a medicament container according to an embodiment.

Although shown as interacting with a single medicament delivery device 100, in other embodiments, an adapter 120 can interact with more than one medicament delivery device 100. In other embodiments, a monitor device 150 can interact with more than one adapter 120 and/or medicament delivery device 100. For example, FIG. 36 shows a medicament delivery system including a locator 250, a first adapter 220A that can be operable to interact with a medicament delivery device 200 and a second adapter 220B that can be operable to interact with a medicament container 260. The locator 250 can include a radio 252, an audible output device 254, and/or one or more sensors 256, and can be operable communicate with the adapter 220A and the adapter 220B, and/or provide an audible output, in a similar manner as described above with reference to the monitor device 150, and as described below.

In particular, the locator 250 can communicate with the adapter 220A to confirm the existence of, identify and/or locate the medicament delivery device 200, as described above with reference to the monitor device 150 and adapter 120. Thus, the adapter 220A can include any of the structure and components, and can function similar to any of the adapters described herein. In this manner, in the event of a medical condition involving the medicament in the medicament container 260 (e.g., an overdose), the adapter 220A can assist the user (or patient) in locating the medicament delivery device 200. In addition, because the locator 250 is in communication with the adapter 220B, the locator 250 and/or the adapter 220B can, as described below, provide compliance and/or historical information related to the use of the medicament in the medicament container 260 (e.g., how many pills were recently removed from the container), as well as instructions and/or assistance in identifying and/or locating the medicament delivery device 200.

The adapter 220B includes a sensor 226 to monitor location, use history, fill level and/or any other suitable parameter associated with the medicament container 260 and/or the medicament delivery device 200. In this manner, when the locator 250 is activated (e.g., by a user), the locator and the adapter 220B can provide information to the user regarding the status of the medicament. In addition to assisting in the location of the medicament delivery device 200, providing such information can be important in determining the appropriate course of action. For example, in some embodiments, the adapter 220B can be operably coupled to the medicament container 260, and the sensor 226 can be operable to determine, measure, record, and/or otherwise monitor the contents and/or the use of the medicament container 260. In some embodiments, the sensor 226 can measure the weight, volume, quantity, and/or any other appropriate parameter of the medicament within the medicament container 260. The sensor 226 can be an optical sensor configured to align with a window of the medicament container 260 to measure color, fill level, turbidity, and/or any other suitable parameter. In some embodiments, the sensor 226 can detect when the cap of the medicament container 260 is removed, when the medicament is administered, the amount of medicament in the medicament container 260, withdrawal of medicament from the medicament container 260, and/or changes in the volume and/or mass of the contents of the medicament container 260. In this manner, the adapter 220A can provide the user, an emergency first responder, and/or any other person information regarding the contents and/or usage history of the medicament container 260.

In one example, the medicament container 260 includes a pain medication, such as opioids. In the event of a serious opioid toxicity or overdose emergency, information regarding the identity and usage history of the opioids may be relevant to the treatment of the patient. If the patient has recently received a large dose of opioids, it may be necessary to treat the patient for an overdose, for example by administering an opioid antagonist. By monitoring the medicament container 260, the adapter 220B (either alone or in conjunction with the locator 250) can alert a user (e.g., a third party) if treatment is needed. The adapter 220B can cooperatively function with the locator 250, the medicament delivery device 200 (and/or the adapter 220A or sleeve of the device) to produce a signal and/or indication identifying and/or locating the medicament delivery device. In particular, the adapter 220A, the adapter 220B and/or the locator 250 can produce and signals and/or provide any indications in a similar manner as the adapter 120 and/or the monitor device 150 described above. For example, the adapter 220A and/or the locator 250 can also instruct the user to use the medicament delivery device 200, which can include the opioid antagonist.

In another example, the medicament delivery device 200 and/or the medicament container 260 can include a dose of vaccine, such as a hepatitis B or HPV vaccine to be administered within a certain time period. The sensor 226 of the adapter 220B can be operable to monitor the storage time and/or temperature of the medicament delivery device 200 and/or the medicament container 260 to improve the likelihood that an efficacious dose of medicament is delivered. If the medicament delivery device 200 and/or the medicament container 260 is not used within a predetermined time period, the adapter 220B can alert the user and/or a caregiver, such as a prescribing doctor, healthcare provider, or insurance company that the medicament has not yet been delivered. For example, the adapter 220B can emit an audible and/or visual alert, e.g., via the audible output device 224. In addition or alternatively, the adapter 220B can send an electronic signal via the radio 222 operable to alert the user and/or healthcare provider (either directly to a remote device, such as a smart phone, or via the locator 250).

In some embodiments, the adapter 220B and/or the adapter 220A can be operable to receive a signal via the radio 222 (although the radio 222 is not shown as being included within the adapter 220A, it is understood that the functionality of the adapter 220A can be the same as or similar to the functionality of the adapter 220B). In some embodiments, for example, the healthcare provider can remotely query the adapter 220 regarding the status and/or use history of the medicament delivery device 200 and/or medicament container 260. In this way, the healthcare provider can determine whether the medicament delivery device 200 and/or the medicament container 260 has been used within the predetermined time period and/or can schedule follow-up contact and/or care based on the use of the medicament delivery device 200 and/or the medicament container 260.

In some embodiments, the locator 250 and/or the adapter 220B can be included within and/or can be a portion of a container within which the medicament container 260 is disposed (e.g., for storage, shipping or the like). For example, in some embodiments the medicament container 260 can be disposed within the adapter 220B, such that the sensor 226 and/or the other components of the adapter 220B are operably coupled to the medicament container 260. In other embodiments, the adapter 220B can be coupled to and/or can be a portion of the medicament container 260. For example, the adapter 220B can be a cap of the medicament container 260, an insert for the medicament container 260, a dispenser for the medicament container 260, a sleeve, a case, and/or label of the medicament container 260.

In some embodiments, the system can include the adapter 220B that is coupled to the medicament container 260 external to the housing or medicament contained therein. For example in some embodiments the adapter 220B can be a sleeve and/or label of the medicament container 260. In other embodiments, the system can include an adapter 220B that is coupled within the medicament container 260. For example, in some embodiments, the adapter 220B can be included within a desiccant package contained within the medicament container 260, on an interior surface of the medicament container 260. Similarly, the adapter 220A can be coupled to, included within and/or can be a portion of the medicament delivery device 200. For example, in some embodiments, the adapter 220A can be a mouth piece that is removably coupled to an inhaler. In other embodiments, the adapter 220A can be a cover that is removably coupled to a nasal delivery system.

Although not shown in FIG. 36, the adapter 220A can include any of the functionality of the adapter 220B described above. For example, the adapter 220A can include a sensor and/or a switch to determine a parameter associated with of operation of the medicament delivery device 200. For example, in some embodiments, the adapter 220A can be coupled to an inhaler (or other multi-dose device), and can track the patient's compliance in using the device. In this manner, the adapter 220A and/or the adapter 220B can function, either independently, in conjunction with each other and/or in conjunction with the locator 250 as "smart sleeves" to improve the efficacy of the dosages contained in either the medicament container 260 or the medicament delivery device 200.

Although described, at least in part, as relating to an emergency situation, the systems and methods described herein can be easily extended to non-emergency situations. For example, in a chronic-care setting a patient can purchase an initial kit that includes the adapters 220A and 220B, and one or more locators 250 configured to communicate with the adapters, as described herein. The user can removably couple the adapter 220B to the medicament container 260 and/or the adapter 220A to the medicament delivery device 200, such that upon refilling the medication, the appropriate adapter can be coupled to the replacement medicament container 260 and/or medicament delivery device 200.

Although the medicament container 260 and the medicament delivery device 200 are described above as being separate (although related in application), in some embodiments, the medicament container 260 can be disposed within the medicament delivery device 200. For example, the medicament container 260 can be a vial of medicament disposed within and delivered by an auto injector, inhaler, and/or other suitable medicament delivery device 260. In another embodiment, the medicament container 260 can be operable to refill and/or replenish the medicament delivery device 200. For example, the medicament container 260 can transfer medicament to the medicament delivery device 200 or, although only one medicament container 260 is shown, in some embodiments, a kit can multiple medicament containers 260 (refills). In other embodiments, the medicament container 260 can be used in conjunction with and/or independently from the medicament delivery device 200. For example, the medicament container 260 can include medicament related to, but not administered via the medicament delivery device 200. For example, the medicament container 260 can include opioids and the medicament delivery 200 device can be operable to deliver an opioid antagonist, such as naloxone, naltrexone or the like, in the event of a severe opioid toxicity or overdose event.

Although the adapter 220A and the adapter 220B are shown as communicating through the locator 250, the devices shown and described herein can communicate in a peer-to-peer fashion.

Figure 37:
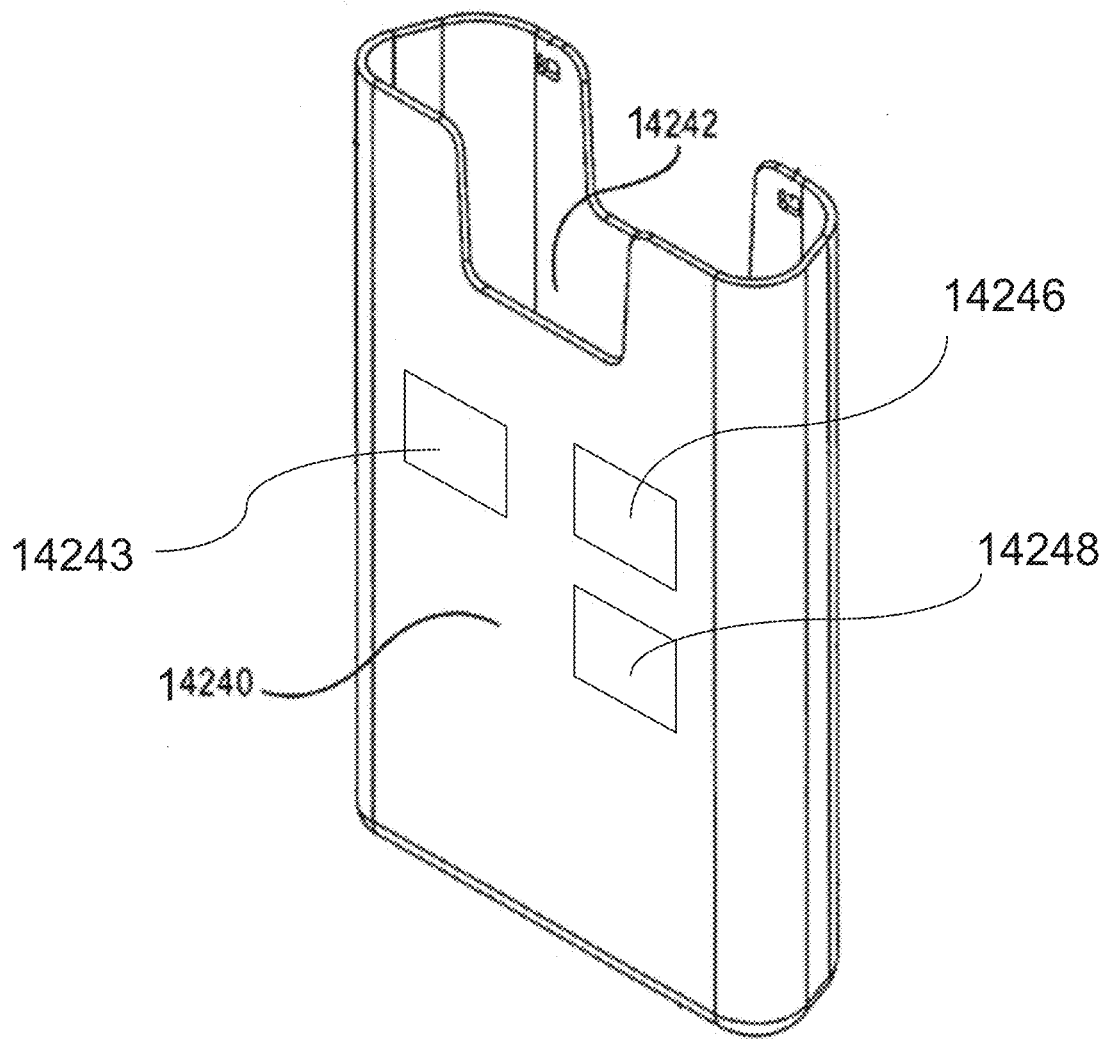
FIG. 37 is a front view of a cover having an electronic circuit system, according to an embodiment.

FIG. 37 is a front view of a cover 14240 (also referred to as an adapter, sheath or sleeve) for a medicament delivery device (not shown). The cover 14240 includes an electronic circuit system having a processor 14246, a radio 14243, and a speaker 14248. In some embodiments, the processor 14246, the radio 14243, and the speaker 14248 can all be disposed on a single printed circuit board. In some embodiments, the cover 14240 can include a battery, such as a coin-cell battery operable to power the processor 14246, the radio 14243, and the speaker 14248. The batteries can be, for example, lithium coin cells model CR1613, CR 2032 or the like. The cover 14240 can be an adapter configured to be coupled to a medicament delivery device, and can perform the functions of the adapter 1210 and/or the sleeve 4200 described above (or any combination of the functions thereof). For example, the cover 14240 can define a cavity 14242 operable to receive the medicament delivery device. In some embodiments, the medicament delivery device (not shown) can include its own electronic circuit system, similar to the circuit system 4900 shown and described above. In some such embodiments, the cover 14240 and the medicament delivery device can each have separate power sources.

The processor 14246 can be any suitable processor. For example, the processor 14246 can be structurally and/or functionally similar to the processor 1216 as shown and described above with reference to FIG. 1. For example, the processor 14242 can be a Bluetooth® Low Energy processor (e.g., of the type shown in FIG. 2) configured to operate the radio 14243 to communicatively couple the cover 14240 to a computing device. In addition or alternatively the processor 14246 can be operable to perform speech processing and/or operate the speaker 14248, for example to generate an audible output, such as a speech output (of the types and in response to the inputs as described herein). Similarly stated, a processor having a single die can be suitable to operate the radio 14243 and the speaker 14248.

Although not shown in FIG. 37, in some embodiments, the adapter 12240 can include any of the modules described herein. For example, in some embodiments, the adapter 12240 can include any of a communication module, a use module and/or a leash module as described above with respect to FIG. 1. Thus, the processor 14246 can execute code to modify one or more characteristics of the wireless communication between the radio 14243 and a computing device (e.g., a cell phone, not shown) to manage the power usage of the cover 14240. For example, in some embodiments, the processor 14246 can execute code to change the communication mode between the cover 14240 (i.e., the "slave" device) and a computing device (i.e., the "master" device) as a function of the status of the medicament delivery device.

Moreover, in some embodiments power management techniques, such as time multiplexing can be executed by the processor 14246. Such power management methods can be performed, for example, by a power module (not shown in FIG. 37). For example, the processor 14246 can be operable to manage power draw such that high-draw and/or processor intensive operations, such as voice processing and operating the radio 14243 are not executed simultaneously. For example, in some embodiments, a method can include delaying and/or extending a communication interval during a time period when operations involving a recorded speech output via the speaker 14248 and/or a light output device (not shown) are performed. In other embodiments, a method can include changing a communication mode during a time period when operations involving a recorded speech output via the speaker 14248 and/or a light output device (not shown) are performed. For example, in some embodiments, a method can include transitioning the device to a sniff or park mode upon activation of the device to conserve power draw from the instruction features of the device.

Figure 35:
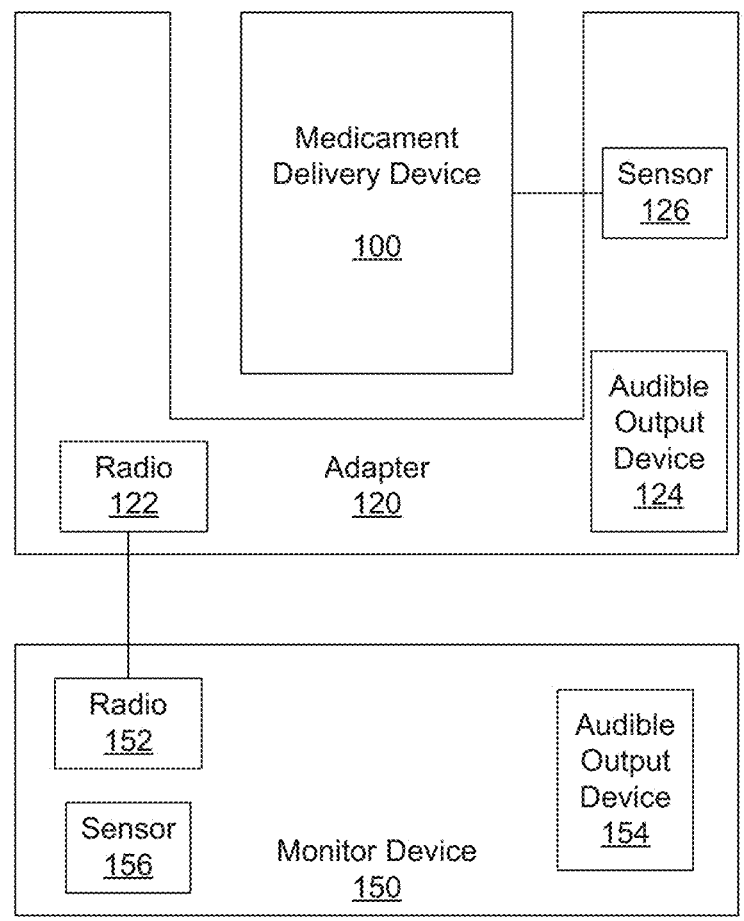
FIG. 35 is a schematic diagram of a monitor device, an adapter, and a medicament delivery device according to an embodiment.

As shown and described with reference to FIGS. 1, 35 and 36, in some embodiments, the cover 14240 can include a switch and/or a sensor operable to detect, for example, when the medicament delivery device is removed from the cover 14240 and/or when medicament delivery device is actuated. In some embodiments, the processor 14246 can be operable to cause the speaker 14248 to generate an audible output, such as a tone or natural speech output in response to the cover 14242 being removed from the medicament delivery device, in response to a signal received via the radio 14243, and/or in response to a sensor detecting the actuation of the medicament delivery device. In addition or alternatively, the processor 14246 can be operable transmit a signal via the radio 14243 (e.g., to a computing device, not shown) in response to the cover 14240 being removed from the medicament delivery device and/or in response to a sensor detecting the actuation of the medicament delivery device. In some embodiment, the processor 14246 can be operable to alter a communication interval and/or communication mode (e.g., from connectable to connected, from sniff to active, and/or from a relatively longer communication interval to a relatively shorter communication interval) in response to the cover 14240 being removed from the medicament delivery device and/or a sensor detecting the actuation of the medicament delivery device. In this manner, the cover 14240 can conserve the power for situations in which wireless communications with the remote computing device is most likely.

In some embodiments, the cover 14240 can also interact with and/or influence the operation of an electronic circuit system of the medicament delivery device contained therein (e.g., medicament injector 4000). For example, as shown and described herein, for example with reference to FIGS. 7, 9, and 25, the cover 14240 can include a battery isolation tab. The battery isolation tab can be configured to isolate a power source (such as a battery) from an electronic circuit of the medicament delivery device when the medicament delivery device is disposed within the cover 14240. Although shown and described with respect to FIG. 25 as isolating the battery from the entire electronic circuit system, in some embodiments, the battery isolation tab can be operable to isolate a only a portion of a circuit while another portion of the circuit remains electrically coupled to the power source. For example, a "leaky" or "hi draw" portion of the circuit (i.e., a portion of the circuit having a relatively high power draw during idle) can be isolated from the battery, while a less leaky or essential portion of the circuit can remain powered. As one example, a portion of a circuit including a communication module, such as a Bluetooth® module, can be continuously powered, while a portion of a circuit including an audio processor and/or speaker can be isolated. In some embodiments, such a battery isolation tab can be a multi-stage battery isolation tab, such that, for example, if the battery isolation tab is in a first position the battery is completely isolated from the circuit, if the battery isolation tab is in a second position, a portion of the circuit is isolated while another portion of the circuit is electrically coupled to the power source, and if the battery isolation tab is in a third position, the full circuit is electrically coupled to the power source.

Figure 38:
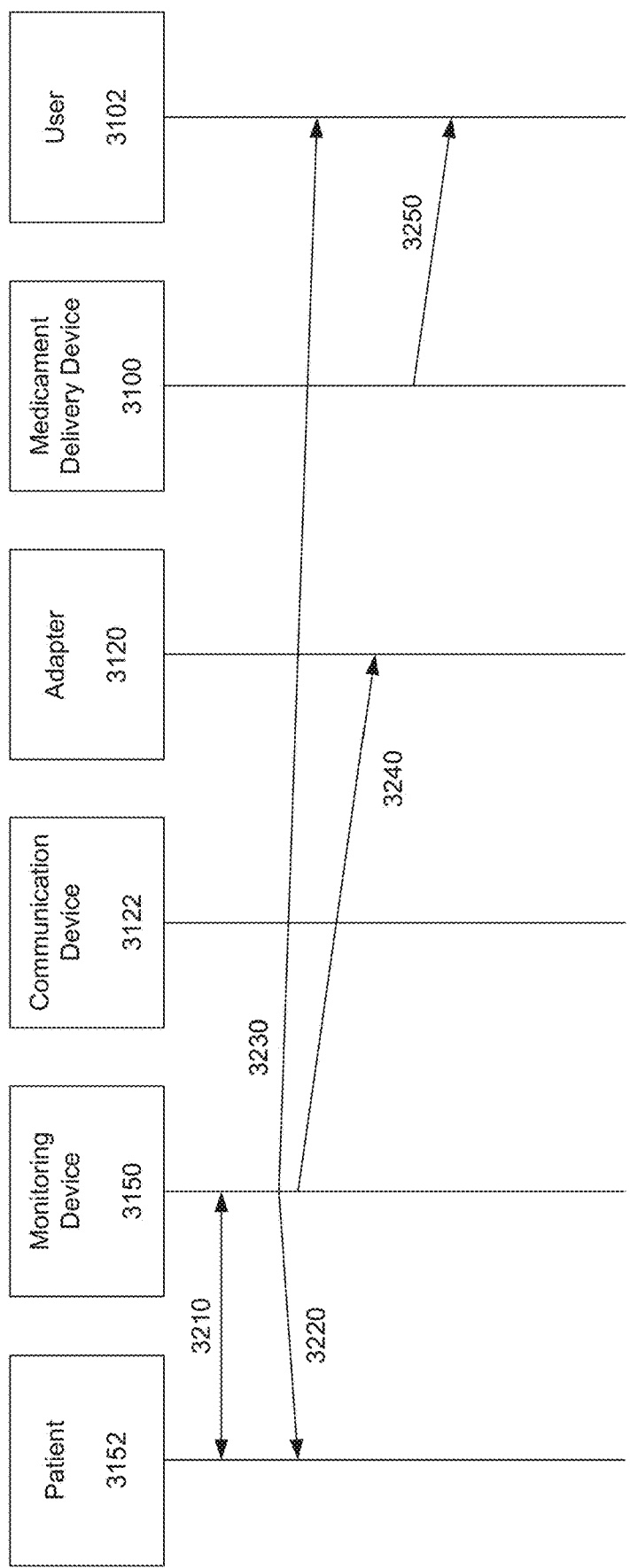
FIGS. 38 and 39 are a signal diagrams representing communications between a patient, a monitoring device, a communication device, a locator device, a medicament delivery device, and a user according to an embodiment.

FIG. 38 is a signal diagram illustrating a series of communications that can be initiated and/or received by any of the devices and system described herein. The signal communications are operable to increase the likelihood that a patient 3152 receives appropriate medical care in the event of a medical emergency and/or during a dosing regimen. In the event that the patient 3152 requires treatment and needs assistance and/or is not able to operate a medicament delivery device 3100 configured to provide the needed treatment, it may be necessary to alert a third-party bystander or emergency first responder (a user 3102). As described herein, the alert can include a notification of the presence of the medicament delivery device 3100 and/or provide the user 3102 instructions for the use of the medicament delivery device 3100. As shown in FIG. 38, a system includes a monitoring device 3150, an adapter 3120 and/or a communication device 3122 that cooperatively aid the patient 3152 and/or the user 3102 in identifying the medical emergency, locating the medicament delivery device 3100, administering the needed treatment, and/or reporting the medical emergency. Although FIG. 38 shows each of the monitoring device 3150, the adapter 3120, the medicament delivery device 3100 and/or the communication device 3122, in some embodiments certain functions attributed to one of these devices can be performed by any other of these devices. Moreover, a system and method according to an embodiment need not include each of these devices.

Each of the monitoring device 3150, the adapter 3120, the medicament delivery device 3100 and/or the communication device 3122 can be operable to send and/or receive signals. The signals can be human perceivable, such as audible, visual, vibratory and/or haptic alerts. In other embodiments, the signals can be electromagnetic signals, radio signals, IR signals and/or signals otherwise not human perceivable. An embodiment can include both human perceivable and signals that are not human perceivable.

As shown by the signal 3210, the monitoring device 3150 is operably coupled to the patient 3152 and can send and/or receive the signal 3210. More particularly, the monitoring device 3150 is operable to sense when the patient 3152 requires the administration of a medicament, e.g., from the medicament delivery device 3100, and can produce the signal 3210 in response thereto. The monitoring device 3150 can be, for example, a sensor operable to detect physiological parameters associated with the patient 3152, such as heart rate/pulse, respiratory rate, blood sugar, blood oxygen, an immune response, acceleration (e.g., associated with a fall), brain activity, and/or the like. In some embodiments, the monitoring device 3150 can be similar to the monitor device 150 and/or the locator 250 described above, or any of the other locators described below. For example, in some embodiments, the monitoring device can be integrated with and/or coupled to a piece of jewelry (e.g., a ring, watch, belt buckle, or necklace) worn by the user, or the like.

In the event the monitoring device 3150 detects a condition that may require medical attention, the monitoring device 3150 can emit the signal 3220 operable to alert the patient 3150 and/or the signal 3220 to alert the user 3102 to the abnormal condition. Signals 3220 and/or 3230 can be an audible and/or visual alert, such as an alarm, a strobing light, and/or a recorded instruction. If the patient 3152 is capable of responding the condition (e.g., the patient 3152 is not incapacitated) the patient 3152 can silence the alarm and/or administer the necessary treatment (e.g., using the medicament delivery device 3100). If, however, the patient 3152 is incapable of responding to the condition (e.g., the patient 3152 is incapacitated), the signal 3230 can notify the user 3102 that the patient 3152 requires medical attention, that the medicament delivery device 3100 is present, provide instructions for using the medicament delivery device 3100, and/or instructions for obtaining further information related to the medicament delivery device 3100.

In addition to producing the signals 3220 and 3230, the monitoring device 3150 can produce the signal 3240 to communicate with an adapter 3120, which can be coupled to or integral with the medicament delivery device 3100. The adapter 3120 can be similar to the locator devices 120 and/or 220 shown and described above. In some embodiments, the adapter 3120 can be incorporated into a sleeve within which at least a portion of the medicament delivery device 3100 is disposed (e.g. similar to the sleeve 4200 shown and described above with reference to FIGS. 3-34). The adapter 3120 can facilitate communication with and/or identification of the medicament delivery device 3100 in accordance with any of the methods described herein.

As described herein, the monitoring device 3150 and the adapter 3120 can cooperate to aid the user 3102 in locating the medicament delivery device 3100. For example, signal 3240 can cause the adapter 3120 to emit an audible or visual alert operable to draw the user's 3102 attention, and/or the monitoring device can be operable to ascertain the location of the adapter 3120, e.g., via radio location techniques, and emit an output operable to guide the user to the adapter 3120. For example, the monitoring device 3150 can emit a tone and/or chirp that varies in pitch, frequency, and/or volume as the distance between the monitoring device 3150 and the adapter 3120 changes. In this way, the adapter 3120 can be operable to guide the user 3102 to the medicament delivery device 3100.

As shown as signal 3250, the medicament delivery device 3100 can provide instructions to the user 3102 and/or can direct the user 3102 to obtain instructions for the use of the medicament delivery device 3100. For example, the instruction can any of the electronic instructions described herein, such as electronic output OP1 and/or OP2 shown and described above with reference to the medicament delivery device 4000. In some embodiments, signal 3250 can include recorded instructions regarding the use of the medicament delivery device 3100. In some embodiments, after the medicament delivery device is located, a visual output in the form of LCD Display output can direct the user regarding instructions for using the device.

In some embodiments, either the patient 3152 and/or the user 3102 can possess the communication device 3122, and the system and/or the communication device 3122 can be adapted and/or enabled to perform all or portions of the functions of the monitoring device 3150, the adapter 3120 and/or the medicament delivery device 3100. In this manner, the system and methods can utilize the communication resources that are commonly available. In particular, in some embodiments, the communication device 3122 can be a smart phone or other portable electronic device (pager, game system, music system or the like). In such embodiments, the systems described herein can be configured to employ the communication resources (e.g., the speakers, display capabilities, signal processing, transmission/reception capabilities, or the like) of the communication device 3122 to enhance the performance of the overall system.

For example, in some embodiments, the medicament delivery device 3100, the monitoring device 3150 and/or the adapter 3120 can include a label having a machine-readable code. The machine-readable code can be, for example, a bar code, a QR Code™ and/or an address of a website. During an event, the user can scan or otherwise read the machine-readable code using the communication device 3122 (e.g., a cellular phone) to access instructions. For example, in some embodiments, upon scanning the machine-readable code, the user's cellular phone will be directed to a website or other location in which instructions for using the medicament delivery device 3100 and/or otherwise treating the patient are provided. In other embodiments, the label can include a text message prompting the user to scan the machine-readable code with the patient's communication device 3122. In a similar manner, the patient's communication device can be directed to a web site or other location in which instructions for using the medicament delivery device 3100 and/or otherwise treating the patient are provided 3122. Moreover, the patient's communication device 3122 can include information unique to the patient, such as, for example, a listing of contacts to reach in the event of an emergency (in some embodiments, by scanning the machine-readable code, a text message will automatically be sent to this list), an application stored locally that provides detailed instructions unique to the patient or the like.

In other embodiments, the communication device 3122 can enable the user 3102 to access the patient's 3152 medical history, provide patient specific instructions, and/or prompt the user 3102 to notify emergency personnel and/or the patient's 3152 emergency contact. For example, in some embodiments, upon detection of an event, the patient's communication device 3122 can emit a ring tone prompting the user 3102 to access the communication device 3122. Upon accessing the patient's communication device 3122, the user 3102 can receive signals and/or information related to the patient's medical history or the like.

In other embodiments, the communication device 3122 (e.g., either the user's mobile computing device or the patient's mobile computing device) can be configured to receive a signal (not shown) from the medicament delivery device 3100 and/or the adapter 3120. The signal can be received, for example, after the communication device 3122 is used to scan a label, tag or other machine-readable code on the medicament delivery device 3100 and/or the adapter 3120. In other embodiments, the signal can be received automatically (e.g., without the need to scan a code), for example, in response to the manipulation of the medicament delivery device 3100. Upon receiving the signal, the communication device 3122 can then transmit visual and audible instructions for using the medicament delivery device 3100. In some embodiments, for example, the medicament delivery device 3100 and/or the adapter 3120 can include an electronic circuit system similar to the electronic circuit system 4900 shown and described above, except that instead of producing an output via LED's (e.g., LED 4958A and 4958B) and/or an audible output device (e.g., device 4956), the electronic circuit system produces a wireless signal in response to actuation of the switches therein (e.g., switches 4926 and 4946). In some embodiments, the wireless signal can be received by the communication device 3122 (e.g., either the user's mobile computing device or the patient's mobile computing device). The communication device 3122 can then, in turn, produce the audible and visual instructions in response to manipulation of the medicament delivery device 3100. This arrangement allows the computing and/or communication resources of the communication device 3120 to be used to enhance the instructions, locating capabilities and/or the like of the systems described herein.

Figure 39:

Although FIG. 38 is shown and described as having a separate monitoring device 3150 and adapter 3120, in some embodiments, some or all of the functions of the monitoring device 3150 and the adapter 3120 can be combined in a single device. For example, as shown in FIG. 39, a system can include and/or employ a cellular phone 6122 operable to communicate with the medical delivery device 6100 (e.g., via Bluetooth®). The cellular phone 6122 can also be configured to communicate with the patient 6152 and/or the user 6102 (e.g., via audio or visual outputs), and the medicament delivery device 6100 (e.g., via Bluetooth®) to aid the patient 6152 and/or the user 6102 in identifying, locating and/or using the medicament delivery device 6100. The medicament delivery device 6100 can be similar to the medicament delivery devices shown and described above. The locator device 6120 can be similar to the locator devices shown and described above, and/or can be integrated into the medicament delivery device or cover (e.g., the sleeve 4200).

For example, the functions of the monitoring devices described above can incorporated into the patient's cell phone 6122 (as indicated by the inclusion of the monitoring device 6150). For example, the monitoring device 6150 can be operable to sense when the patient 6152 requires the administration of a medicament. As described above with reference to FIG. 38, the monitoring device 6150 can be operably coupled to monitor the patient 6152, as shown by the arrow 6210. The monitoring device 6150 can comprise sensors incorporated into and/or operatively coupled to the cell phone 6122, such as accelerometers, gyroscopes, and/or peripheral devices, such as heart rate monitors. Upon detecting a condition, the patient's 6152 cell phone can alert the patient 6152 (via signal 6220) and/or the user 6102 (via signal 6230). For example, in some embodiments, the cell phone 6122, can emit an audible, visual, and/or haptic signal to draw the attention of the patient (e.g., signal 6220) and/or the user (signal 6230). Signals 6220 and/or 6230 can instruct the patient 6152 and/or the user 6102, respectively, that the patient 6152 requires medical attention.

In some embodiments, the system can include one or more sensors external to the cell phone 6122, but which are coupled to the cell phone, either wireless or via a wired connection. For example, in some embodiments the patient 6152 may wear a monitoring device, such a glucose meter, a heart rate monitor or the like. Although such external devices may produce an audible alarm, the systems and methods described herein allow the patient's cell phone 6122 to act as a central "hub" to receive such signals, produce an enhanced output, communicate with the medicament delivery device 6100 or the like.

The cell phone 6122 can also be operable to display e.g., via a visual output device, or emit, e.g., via an audible output device, information and/or instructions regarding the patient's medical history and/or the administration of medicament using the medicament delivery device 6100. The cell phone 6122 can also automatically contact emergency personnel and/or prompt the patient 6152 and/or the user 6102 to contact emergency personnel.

For example, in some embodiments, the cell phone 6122 (either the patient's cell phone or the user's cell phone) can execute an application (e.g., in hardware) that can unlock and/or otherwise configure the cell phone 6122 to be used by the patient 6152 and/or the user 6102. In some embodiments, the cell phone 6122 can automatically display a prompt and/or instruction upon detecting a specified condition. Thus, the cell phone 6122 can be configured to be useable and/or provide information to the user 6102 in the event of a medical emergency without requiring a password or unlock sequence. For example, in some embodiments, the touch screen of the cell phone 6122 can display a button in response to the detection of a specified condition that prompts a user (e.g., a third party) to enter the application. In other embodiments, the cell phone 6122 can display a message prompting the user to "swipe," scan or read a particular code thereby unlocking the cell phone for subsequent use as described herein. For example, in some embodiments, the user can be prompted to swipe, scan or read an identification card, another device, a medicament container or the like.

The cell phone 6122 can aid the user 6102 in administering medicament to the patient 6152 using the medicament delivery device 6100. For example, the cell phone 6122 can send a signal 6240 to the medicament delivery device 6100 to aid the user 6102 in locating the medicament delivery device 6100. The cell phone 6122 can provide instructions to assist the user 6102 in administering a medicament to the patient 6152 via the medicament delivery device 6100. In addition, the cell phone 6122 can also send a signal to administer the medicament without the user interfacing with the medicament delivery device 6100.

Figure 40:
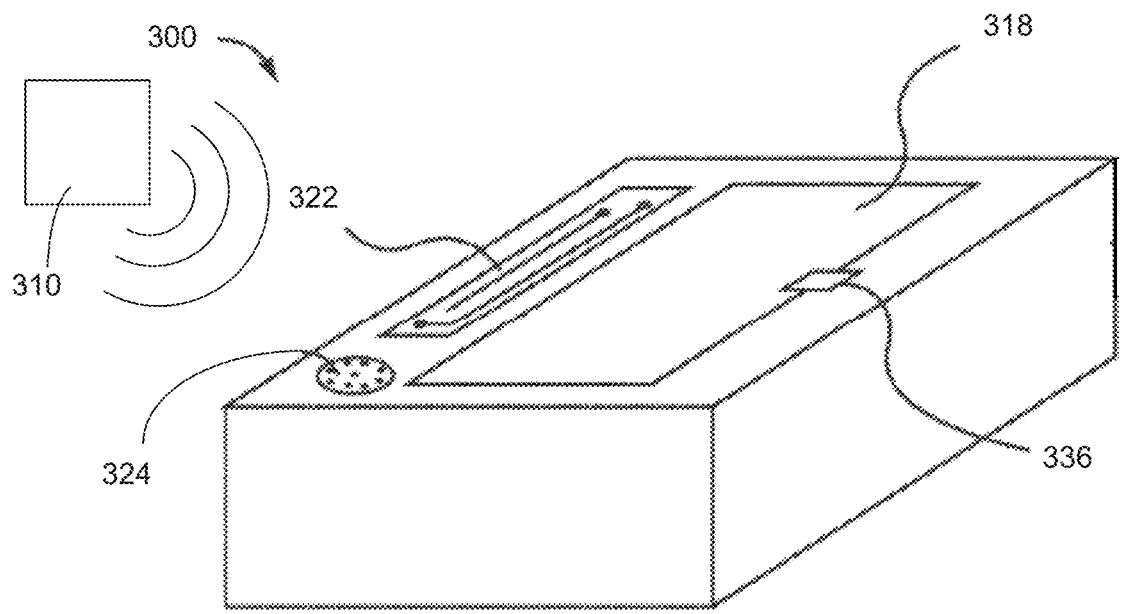
FIGS. 40 through 42 are isometric views of a kit containing a medicament container in a first configuration, a second configuration and a third configuration, respectively, according to an embodiment.
Figure 41:
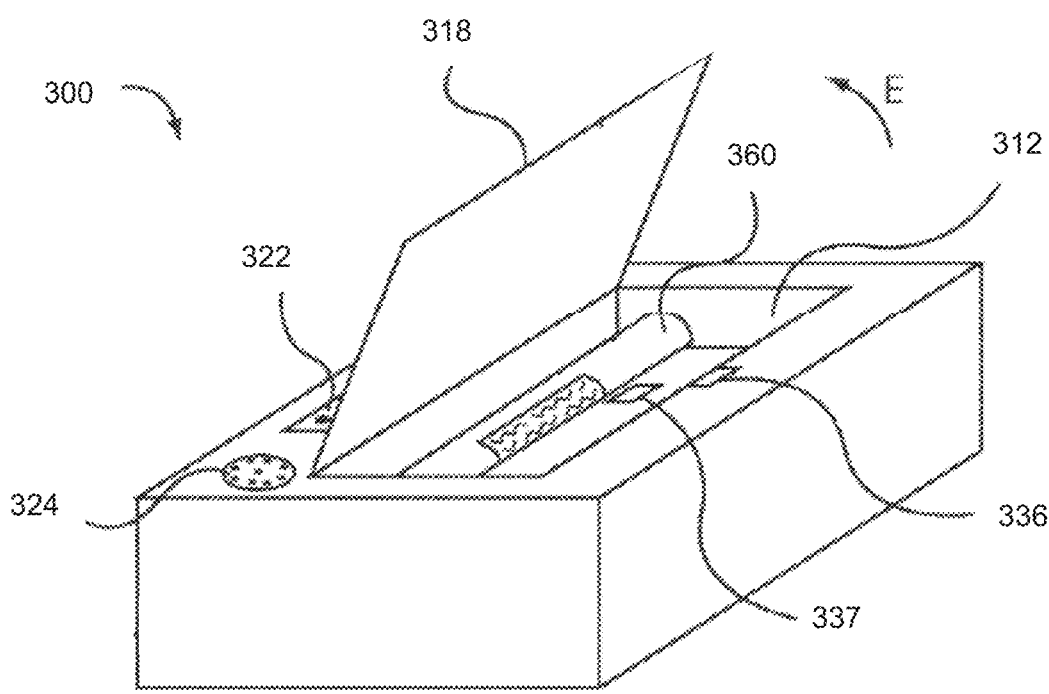
Figure 42:
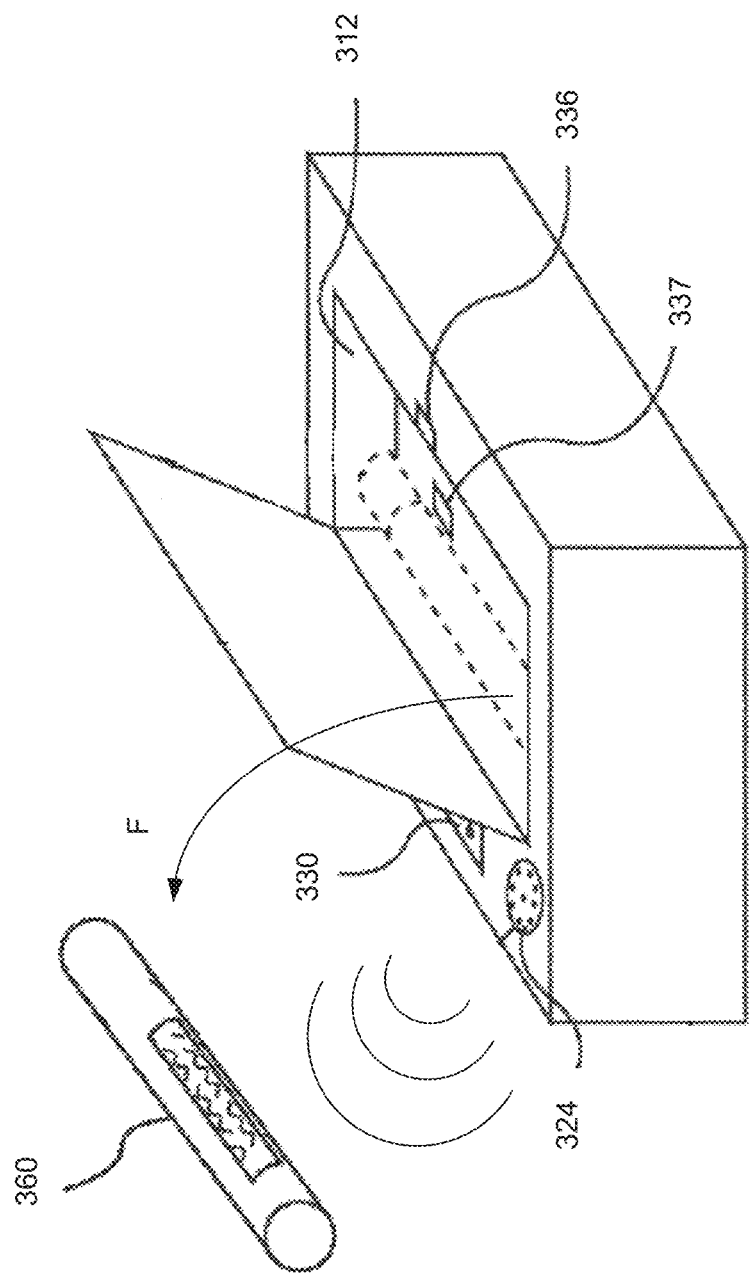

Although the locators (e.g., monitor device 150) are shown and described above as being "wearable" items, such as a key fob, jewelry or the like, in other embodiments a locator can be a substantially stationary item. Moreover, although the locators (e.g., monitor device 150) are shown and described above as being unique to a particular patient, in other embodiments, a locator can be used to track multiple different patients, users or care-givers and/or to communicate with multiple different devices (either different devices of the same type or different devices of different types). Such a locator can be used, for example, in an institutional setting (schools, nursing homes, hospitals or the like) or in a public access setting (restaurants, airports, health clubs or the like) to improve the ability of patients and user to identify, locate and/or actuate a variety of different medicament delivery devices. Moreover, in some embodiments, a locator can, in addition to performing the identification and/or location features described herein, serve to prevent unauthorized and/or undesired access to medicaments. For example, FIGS. 40-42 depict a kit (or container) 300 according to an embodiment. The kit 300 includes a medicament container 360 containing any suitable medicament. The kit 300 can be intended for home and/or institutional use and can be wall-mounted and/or otherwise substantially fixed in a particular location. The kit 300 can store and/or dispense a medicament (e.g., from within the medicament container). In some embodiments, the kit 300 can dispense an opioid and/or provide access control for an opioid or other controlled substance.

The kit 300 also includes a movable portion 318, such as, for example, a hinged lid, that has a first position (see FIG. 40) and a second position (see FIGS. 41-42). When the movable portion 318 is in the first position, the movable portion 318 covers an internal region 312 defined the kit 300. Conversely, when the movable portion 318 is in the second position, at least a portion of the internal region 312 of the kit 300 is exposed. Said another way, when the movable portion 318 is in the second position, the medicament container 360 can be removed from the internal region 312 of the kit 300.

The container or kit 300 includes an electronic circuit system 322 that is operatively coupled to and/or includes a radio 324, a first switch 336, and a second switch 337. The switches can be operably coupled to any suitable mechanism. In particular, the first switch 336 is coupled to a lock mechanism (not shown) that, when in the locked configuration, will prevent the movable portion 318 from being moved into the opened position. The electronic circuit system 322 is includes an actuator or other mechanism configured to cause the first switch 336 to move between a first state (e.g., closed) and a second state (e.g., opened) when the radio 342 receives a signal from an access control device 310 and/or the electronic circuit system 322 validates the signal. When the first switch 336 is in its second state (e.g., opened) the locking mechanism is "unlocked" such that the movable portion 318 can be moved between its first position and its second position, as indicated by arrow E in FIG. 41. In this manner, the patient or user can only access the medicament container when the access control device 310 is present and is manipulated to send the access signal.

The access control device 310 can be, for example an RFID device. The electronic circuit system 322 can log information associated with the access control device 310, such as a unique identifier (e.g., when the kit 300 is configured to be accessed by more than one user each having a unique access control device 310), time of access, number of access attempts, time between access attempts, etc. In some embodiments, the electronic circuit system 322 can be configured to only allow access to the contents of the kit 300 (e.g., only move the first switch 336 from the first state to the second state) at certain times, after certain intervals, and/or to certain individuals. The radio 324 can transmit a signal associated with usage history to, e.g., a remote monitoring device (such as a computer), and/or receive and respond to a query regarding usage history.

As an example, the medicament container 360 can include a controlled substance and/or a medicament with potentially dangerous side effects, such as an opioid. This arrangement limits access to the medicament container 360 the identity of the user (e.g., via the access control device 310), based on time, past usage, and/or quantity. In some embodiments, access to the medicament container 360 can also be limited to patients having a medicament delivery device (e.g., an auto-injector) containing an opioid antagonist. In this manner, the system ensures access to the opioid only when there exists the likelihood that rapid treatment will be available in the event of an overdose (i.e., via the presence of the medicament delivery device in close proximity to a user, patient or care-giver). In such an embodiment, the medicament delivery device containing the opioid antagonist can be or include the access control device 310. The medicament delivery device can include, for example, an RFID chip detectable by the radio 324. When the patient presents the medicament delivery device (the access control device 310), the electronic circuit system can identify the user and determine whether to grant access to the medicament.

The second switch 337 is configured to move between a first state (e.g., closed) and a second state (e.g., opened) when the medicament container 360 is removed from the internal region 312 of the kit 300, as indicated by the arrow F in FIG. 42. The electronic circuit system 330 can be configured to log the removal of the medicament container 360 in response to the changing state of the switch. The electronic circuit system can associate the removal of the medicament container 360 with a user identifier provided by the access control device 310. In some embodiments, second switch 337 can be operable to determine the quantity of medicament removed from the interior region 312 of the kit.

In some embodiments, the electronic circuit system 330 can be configured to cause the radio 324 to transmit a signal associated with the removal of the medicament container 360 from the interior region 312 of the kit 300. For example, in some embodiments, the kit 300 can communicate with a computer (not shown) to log medicament usage and/or send notifications (e.g., notify medical providers, notify emergency personnel, notify pre-programmed contact personnel, etc.).

In some embodiments, the electronic circuit system 330 can be configured to output an audible and/or visual output, for example via a speaker and/or an LCD screen when the second switch 337 is moved from its first state to its second state, for example, a recorded speech output and/or a video output associated with an identification of the medicament container 360, an identification of patient symptoms (e.g., instructions for assessing the physical condition of the patient) and/or an instruction for using the medicament. For example, in some embodiments the output can be an audio-visual output via both a speaker and an LCD screen step-by-step instructions for using the medicament.

Although the movable member 318 is shown and described as being a hinged lid, in some embodiments, the movable member can be coupled to the container in any suitable fashion. For example, in some embodiments, the movable member 318 can be a removable cover that is slidingly coupled to the container. In other embodiments, the movable member 318 can be a removable cover that is threadedly coupled to the container (i.e., a removable cap). In yet other embodiments, the movable member 318 can be a removable cover that is coupled to the container via an interference fit. In yet other embodiments, the movable member 318 can be a frangible cover that is irreversibly removed from the container during use of the medical device. For example, in some embodiments the movable member 318 can be a frangible cover that provides a tamperproof seal, a sanitary seal, or the like.

Although the containers, kits and/or adapters are shown and described in some instances above as being rigid, box-like containers, in other embodiments, a container, kit and/or adapter can have any suitable shape and/or flexibility. For example, in some embodiments, a container, kit and/or adapter can be a flexible, pouch-like container. Such a container, kit and/or adapter can be more easily carried in certain circumstances, such as, for example at outdoor events (e.g., children's camps, concerts, picnics or the like). In other embodiments, a container, kit and/or adapter can be a tube or sheath (e.g., similar to the cover 4200 described above) configured to contain all or a portion of a medicament delivery device 360.

Although FIGS. 40-42 depict and describe a medicament container 360 removable from the interior region 312 of the container or kit 300, in other embodiments, the kit 300 can be operable to dispense medicament without a container 360. For example, the kit 300 can be operable to dispense medicament tablets, pills, capsules, liquid, aerosols, and/or any other suitable medicament form. In such embodiments, the movable member 318 can be a dispensing mechanism configured to meter a quantity of medicament. For example, the moveable member 318 and/or the second switch 337 can be operable to count and dispense an appropriate number of pills. The moveable member 318 and/or the second switch 337 can also include a loss-in-weight meter, a volumetric pump, and/or any other suitable mechanism for dispensing, metering, and/or measuring the removal of medicament and/or medicament container(s) 360 from the interior region 312.

In some embodiments, the medicament container 360 can be a medicament delivery device and/or the medicament container 360 can be disposed within a medicament delivery device. In such an embodiment, the medicament delivery device can be similar to the medicament delivery device 4000 shown and described above.

Figure 43:
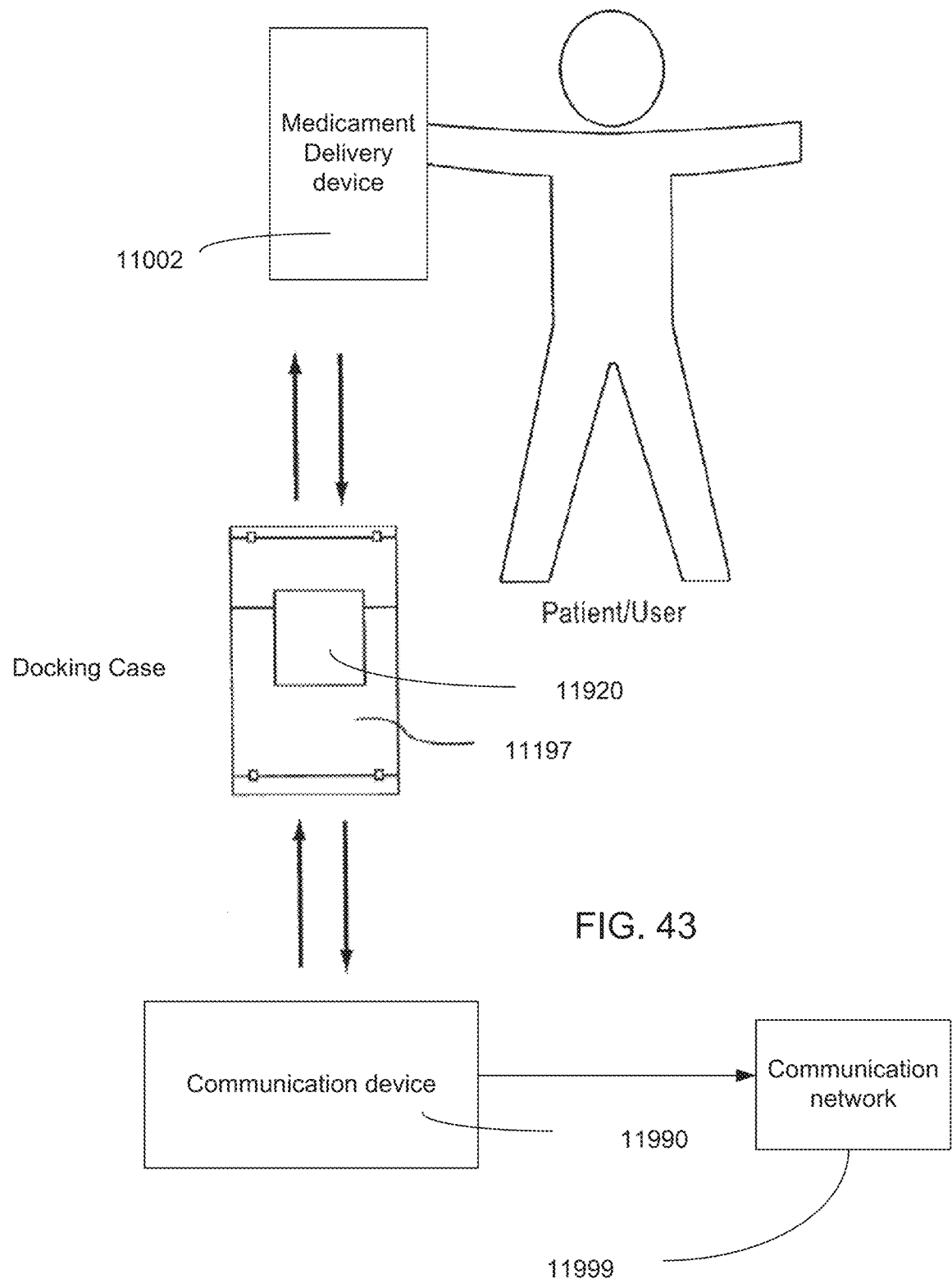
FIG. 43 is a schematic diagram showing the interactions between a patient/user, a medicament delivery device, a docking case, a communication device, and a communication network according to an embodiment.

FIG. 43 depicts a schematic illustration of a medicament delivery device 11002 operable to be coupled to a case or cover 11197. The medicament delivery device 11002 can be similar to the medicament delivery devices shown and described above, such as medicament delivery device 4000. The case 11197 can be a case operable to be physically and/or electrically coupled to the medicament delivery device 11002 and a communication device 11990 (e.g., a cell phone). The case 11197 can be a sleeve (such as the cover 4200 described above), a flexible pouch or the like. The case 11197 includes an electronic circuit system 11920. The electronic circuit system 11920 can be any electronic circuit system of the type shown and described herein. For example, the cover 11197 can be structurally and/or functionally similar to the cover 14240 shown and described above with reference to FIG. 37. For example, the electronic circuit system 11920 can be configured to monitor the status of the medicament delivery device 11002, interact with (or be actuated by) to produce a signal, actuate the medicament delivery device 11002, provide instructions for using the medicament delivery device 11002 or the like.

In some embodiments, the medicament delivery device 11002 can include a safety guard that is moved prior to administering the medicament and an actuator that is moved to initiate delivery of the medicament. The safety guard can be similar to safety lock 4700 shown and described above. The actuator can be similar to the base 4300 shown and described above. In some embodiments, the medicament delivery device 11002 and/or the case 11197 can detect that the medicament delivery device 11002 is ready for use and send a signal to the communication device 11990. In response, the communication device 11990 (e.g., the cell phone) can provide instructions to the patient and/or user regarding the use of the medicament delivery device 11002. For example, in some embodiments, movement of the safety guard (to place the medicament delivery device 11002 in a "ready" configuration) can trigger the electronic circuit system 11920, causing the case 11197 to "detect" the status of the medicament delivery device 11002. The case 11197 can then send a signal that is received by the communication device 11990 such that an application running on the communication device 11990 provides instructions. In some embodiments, the communication device 11990 can be operable to send a signal, such as an alert to a pre-programmed emergency contact via the communication network 11999.

In some embodiments, the case 11197 can include sensors and/or can receive signals from the medicament delivery device 11002. In this manner, the case 11197 can transmit information associated with the use of the medicament delivery device 11002 to the communication device 11990. The communication device 11990 can provide instructions to the patient and/or user based on the status and/or a change in configuration of the medicament delivery device 11002. For example, the communication device 11990 can provide different instructions associated with the removal of a safety guard, positioning the medicament delivery device 11002 and/or case 11197 against a body part, and/or triggering the medicament delivery device 11002 (e.g., movement of an actuator or base).

In some such embodiments, the communication device 11990, the case 11197, and the medicament delivery device 11002 can be communicatively coupled such that the status and/or use of the medicament delivery device 11002 can be remotely monitored. For example, the case 11197 can be operable to report the status of the medicament delivery device 11002 to a remote server via the communication device 11990 and the communication network 11999.

Figure 44:
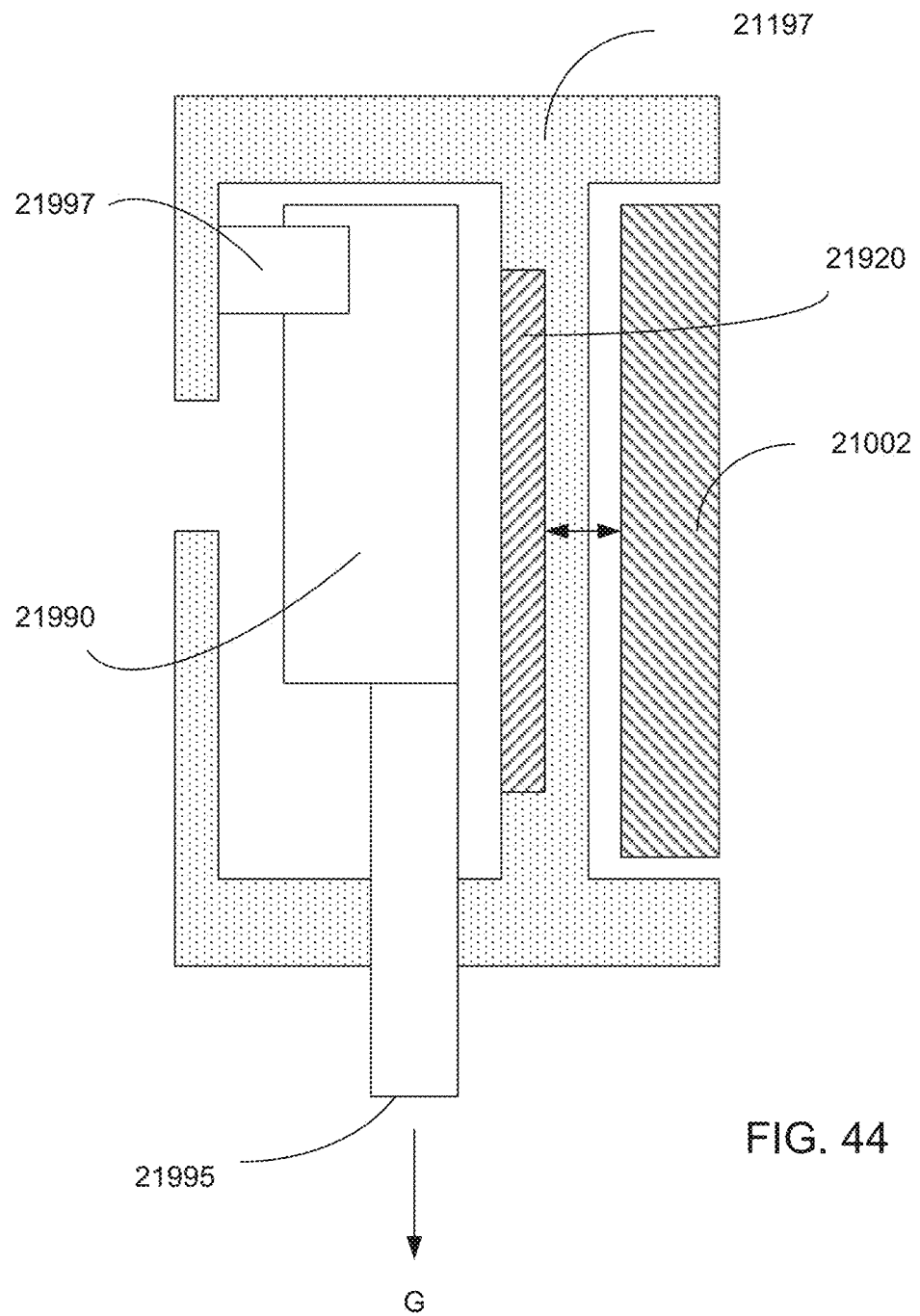
FIGS. 44 and 45 are schematic diagrams of a docking case coupled to a medicament delivery device and a communication device in a first configuration and a second configuration, respectively, according to an embodiment.
Figure 45:
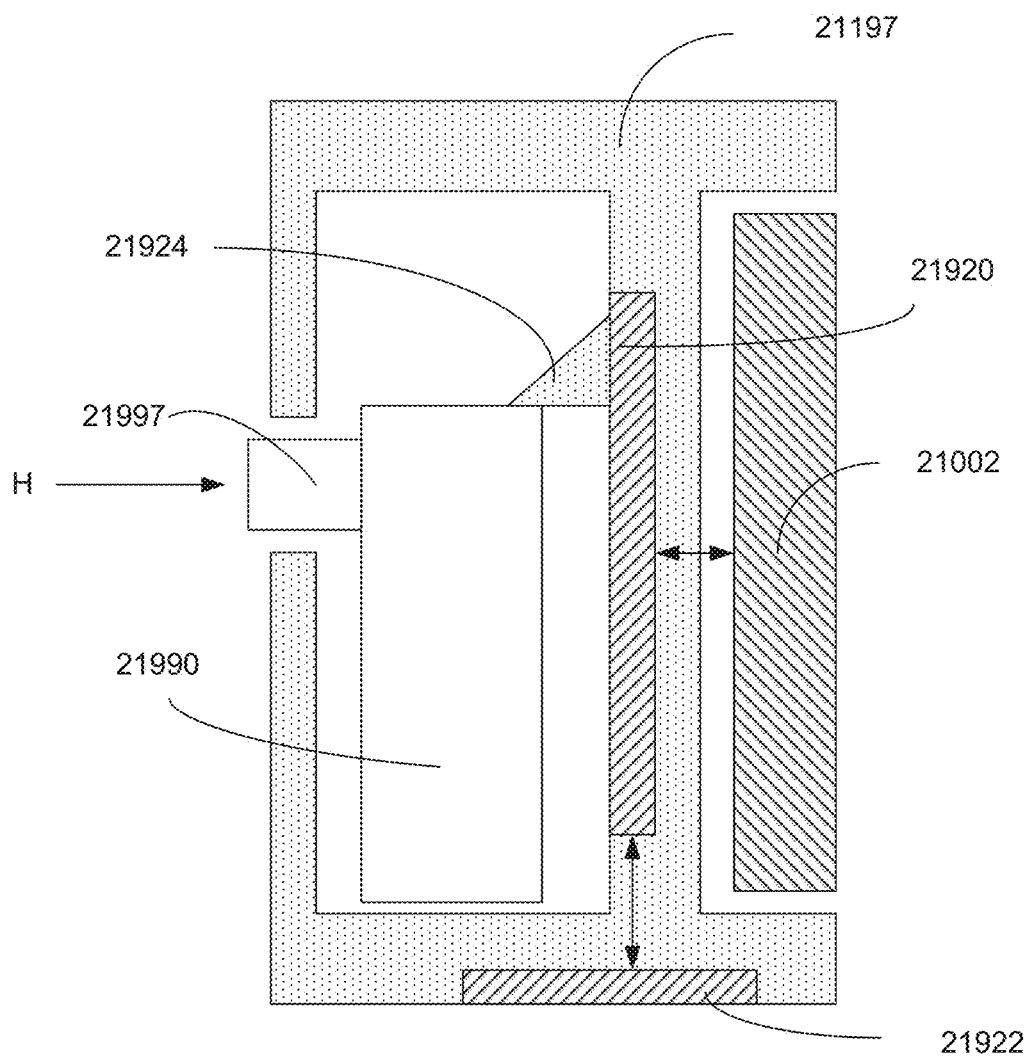

In some embodiments, a case or cover can be configured to removably contain at last a portion a medicament delivery device and a communication device (e.g., a cell phone). In this manner, the case can operably couple a medicament delivery device to an off-the-shelf communication device to produce a "smart" medicament delivery device. For example, FIGS. 44 and 45 are schematic diagrams of a case 21197 coupled to a medicament delivery device 21990 and a cell phone 21002. The medicament delivery device can be similar to the medicament delivery device 4000 as shown and described above or any other suitable device. The case 21197 can define a first volume operable to contain the medicament delivery device 21990 and a second volume operable to contain a cell phone 21002. Thus, the case 21197 can couple the medicament delivery device 21990 to the cell phone 21992, thereby increasing the likelihood that the medicament delivery device 21990 is available in the event that a medicament is needed.

The case 21197 contains an electronic circuit 21920. The electronic circuit system 21920 can be operable to store, process and/or produce electronic signals associated with the use of the medicament delivery device 21990. The electronic system 21920 can be similar to any of the electronic circuit systems shown and described herein. Moreover, the electronic system 21920 is communicatively coupled to the cell phone 21002. The electronic system 21920 can be communicatively coupled to the cell phone 21002 via any suitable mechanism, such as, for example via a wired configuration (via the docking port, USB port, or other port on the cell phone 21002), via a physical connection (e.g., via a member, switch actuator or the like that transmits input to the cell phone 21002 via the touch screen or other buttons on the cell phone 21002) or wirelessly via an RF or optical signal. In some embodiments, the electronic circuit system 21920 can provide an input to the cell phone 21002 via a microphone of the cell phone 21002. For example, in some embodiments, manipulation of the case 21197 and/or the medicament delivery device 21990 disposed therein (as described below) can result in the electronic circuit system 21920 producing a pressure wave (either audible or inaudible) having a particular frequency or pattern of frequencies that is detectable by the microphone. In this manner, the electronic circuit system 21920 can trigger the cell phone to send a signal, run an application, or the like, based on the status and/or change in configuration of the medicament delivery device 21990.

In some embodiments, the electronic circuit system 21920 can be operably coupled to the medicament delivery device 21990. In some embodiments, the case 21197 and/or the electronic circuit system 21920 can be physically, but not electronically coupled to the medicament delivery device 21990. In such an embodiment, the case 21197 can be operable to monitor the status of (e.g., to receive input from) the medicament delivery device via physical changes and/or forces applied by or to the medicament delivery device 21990, as described in more detail herein.

The medicament delivery device 21990 includes a safety tab 21995 and an actuator 21997. The safety tab 21195 and the actuator 21997 can be, for example, similar to the safety lock 4700 and the base 4300, respectively, shown and described above. As shown, in FIG. 44, a portion of the safety tab 21995 is disposed outside of the case 21997 prior to use of the medicament delivery device 21990. In this manner, although the medicament deliver device 21990 is disposed within and/or is covered by the case 21977, the user can prepare the medicament delivery device 21990 for actuation by accessing the exposed portion of the safety tab 21995. The safety tab 21995 can be removed before using the medicament delivery device 21990 as indicated by arrow G in FIG. 44. Moreover, removing the safety tab 21995 can cause the medicament delivery device 21990 to change position (i.e., to a "ready position") within the case 21197. In this manner, a delivery member (e.g., a needle) of the medicament delivery device 21990 can be moved in proximity to the opening through which the safety tab 21995 was disposed, thereby preparing the device to deliver the medicament therein.

When the safety tab 21995 is removed, the medicament delivery device 21990 can be secured in the ready position by a movable retaining portion 21924 of the case 21197. The retaining portion 21924 can be a spring-actuated tab, a deformable portion of the case 21197 or the like that, upon movement of the proximal edge of the medicament delivery device 21990, is released to limit movement of the medicament delivery device 21990. Additionally, the electronic circuit 21920 can sense that the retaining portion 21924 has secured the medicament delivery device 21990 in the ready position and can send a signal to the communication device 21002. In response, the cell phone 21002 can provide an instruction to the user and/or send a signal to a remote monitoring device, e.g., via a network, an emergency dispatch system (911 call) or the like. For example, the cell phone 21002 can instruct the user to place the case 21197 against the thigh and/or send a notification, such as an SMS message to a pre-programmed emergency contact.

The electronic circuit 21920 can sense that the retaining portion 21924 has secured the medicament delivery device 21990 via any suitable mechanism, such as, for example, a switch that is actuated upon movement and/or removal of the safety tab 21995, movement of the housing of the medicament delivery device 21990 or release and/or movement of the retaining portion 21924.

In some embodiments, the case 21197 can include a sensor 21992 (see FIG. 45) operable to detect if the case 21197 and the medicament delivery device 21990 are positioned against the body of the user. Accordingly, the electronic circuit system 21920 can send a signal to the communication device 21002 when the sensor 21922 detects that the case is properly positioned. In response, the communication device 21002 can provide an instruction to the user and/or send a signal to a remote monitoring device. For example, the communication device 21002 can instruct the user to actuate the medicament delivery device and/or send a notification, such as an SMS message to a pre-programmed emergency contact.

With the medicament delivery device 21990 in the ready position, as indicated in FIG. 45, the actuator 21997 is exposed and/or is disposed at least partially outside of the case 21997. In this manner, the medicament delivery device 21990 can be actuated by moving an actuator 21997, as indicated by arrow H. Actuating the medicament delivery device 21990 can cause it to deliver a medicament (e.g., as described above with reference to the device 4000). The electronic circuit system 21924 can detect that the medicament delivery device 21990 has been actuated, for example, by detecting a force associated with actuation against the retaining portion 21924, and can provide an instruction to the user and/or send a signal to a remote monitoring device. For example, the communication device 21002 can instruct the user to seek medical attention, and/or send a notification, such as an SMS message to a pre-programmed emergency contact. In other embodiments, a portion of the actuator 21997 can actuate and/or contact a switch of the electronic circuit system 21920 such that a signal is sent to the cell phone 21002.

In this manner, the electronic circuit system 21920 can send electronic signals associated with the status, use, and/or other function of the medicament delivery device to and/or receive electronic signals from a communications network via the cell phone 21002.

Figure 46:
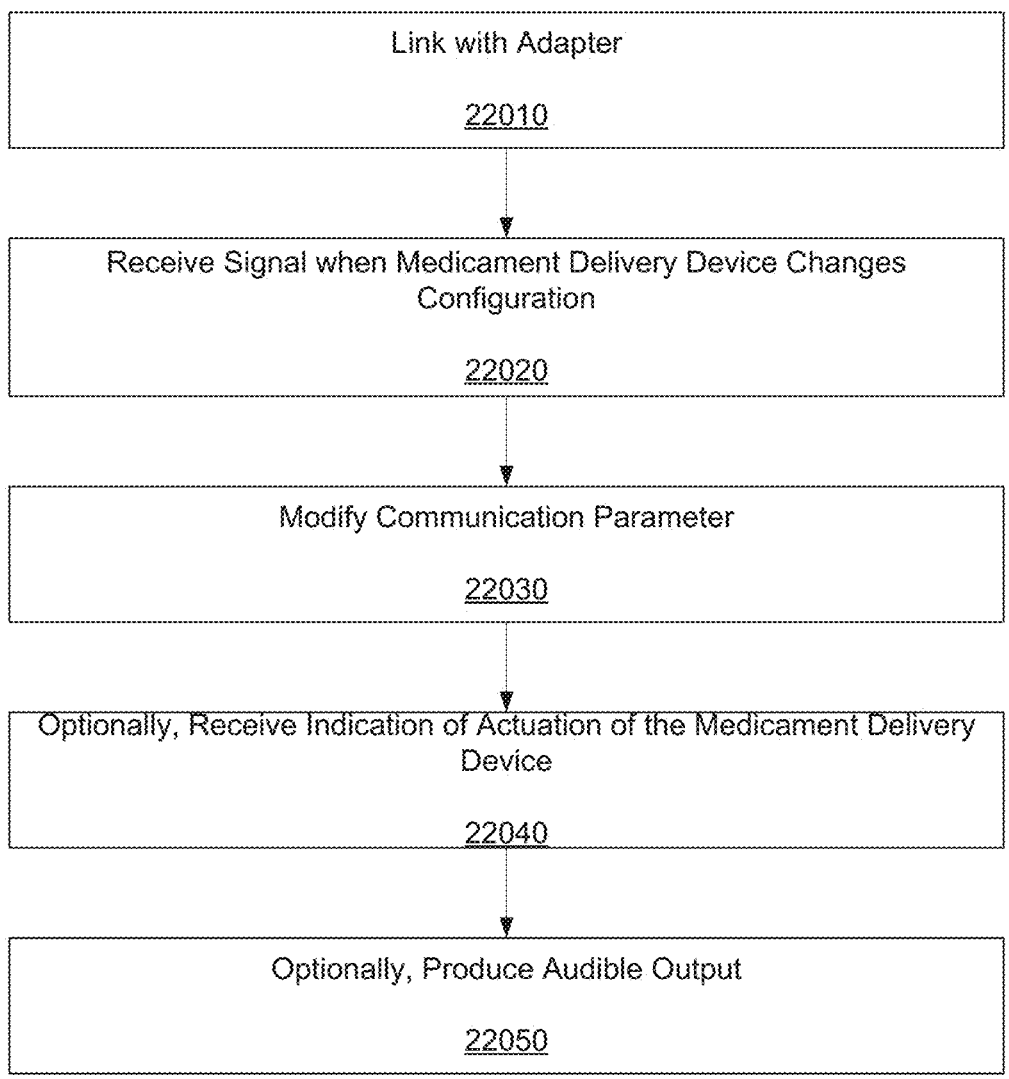
FIGS. 46 and 47 are flow charts of methods associated with monitoring an adapter, according to two embodiments.

FIG. 46 is a flow chart of a method pairing an adapter with a computing device. The adapter (which can be coupled to and/or configured to be coupled to a medicament delivery device and/or a simulated device) and the computing device can be structurally and/or functionally similar to the adapter 1210 and/or the computing device 1510, as shown and described above with reference to FIG. 1, or any other adapters and devices shown and described herein. At 22010, the computing device can establish a communication link according a wireless protocol, such as a Bluetooth® link, with the adapter. In some embodiments, the communication link (or pairing of devices) can be maintained indefinitely (e.g., as long as the adapter and the computing device are within range and both devices are powered). In other embodiments, the communication link (or pairing of devices) can time out after a pre-determined time period, for example, if there is no data associated with the status and/or use of a medicament delivery device within the time-period, which may be 1 hour, 1 day, 2 days, and/or any other suitable time period.

In some instances, maintaining an active link can be more energy efficient than repeatedly linking with the adapter. In such an instance it may be desirable to maintain the link. In some embodiments, the link can be maintained, but the computing device can instruct the adapter to enter a sniff or park mode or other suitable mode to conserve power.

At 22020, a signal associated with a use of and/or change in configuration of the medicament delivery device can be received from a sensor. For example, the adapter can include a switch operable to detect when the medicament delivery device is removed from the adapter and/or when the medicament delivery device is armed (e.g., when a safety tab is removed). In other embodiments, the adapter can include an optical sensor to detect a change in status of the medicament delivery device (e.g., to detect a change in the opacity and/or color of the medicament, to detect removal from the adapter or the like). In yet other embodiments, the adapter can include a microphone to detect a sound pressure wave associated with a change in the configuration and/or status of the medicament delivery device. Such a change in sound pressure wave can be produced by a mechanical feature (e.g., a signature "snap" sound when the medicament delivery device is removed) or electronically (e.g., via a series of tones produced by the medicament delivery device when it is powered up).

In response, the computing device and/or the adapter can modify a parameter associated with the communication link, at 22030. For example, in some embodiments, a communication mode can be altered (e.g., from a sniff mode in effect prior to receiving the signal to an active mode). In other embodiments, an advertising interval can be altered, and/or a communication interval can be altered. For example, it may be desirable to decrease a communication interval (e.g., the time between successive signals, portions of a signal and/or data packet transfers) when the medicament delivery device is readied for use to increase communication bandwidth and/or decrease the latency of the connection. In this way, more data and/or more timely data can be transferred between the adapter and the paired computing device during the delivery of a medicament.

Optionally, at 22040 the computing device can receive an indication that the medicament delivery device was actuated. For example, the adapter can include a sensor operable to detect the actuation of the medicament delivery device (which can be the same or a different sensor as discussed above). When the adapter senses the actuation, it can send a signal to the computing device, which can be received, at 22040. In response to receiving the indication of the actuation, the computing device and/or the adapter can optionally produce an audible output, at 22050. For example, the computing device output a verbal instruction that a medicament has been delivered, instruction to contact a doctor and/or emergency response, instructions for follow-up care, and so forth. In addition or alternatively, the computing device can be operable to send a signal to a remote device (e.g. similar to the remote device 1610 as shown and described with reference to FIG. 1) reporting the actuation of the medicament delivery device. Furthermore, in an embodiment where the computing device is a mobile phone, the computing device can be operable to initiate a telephone call, for example, to 911, an emergency contact, a doctor, etc.

Figure 47:
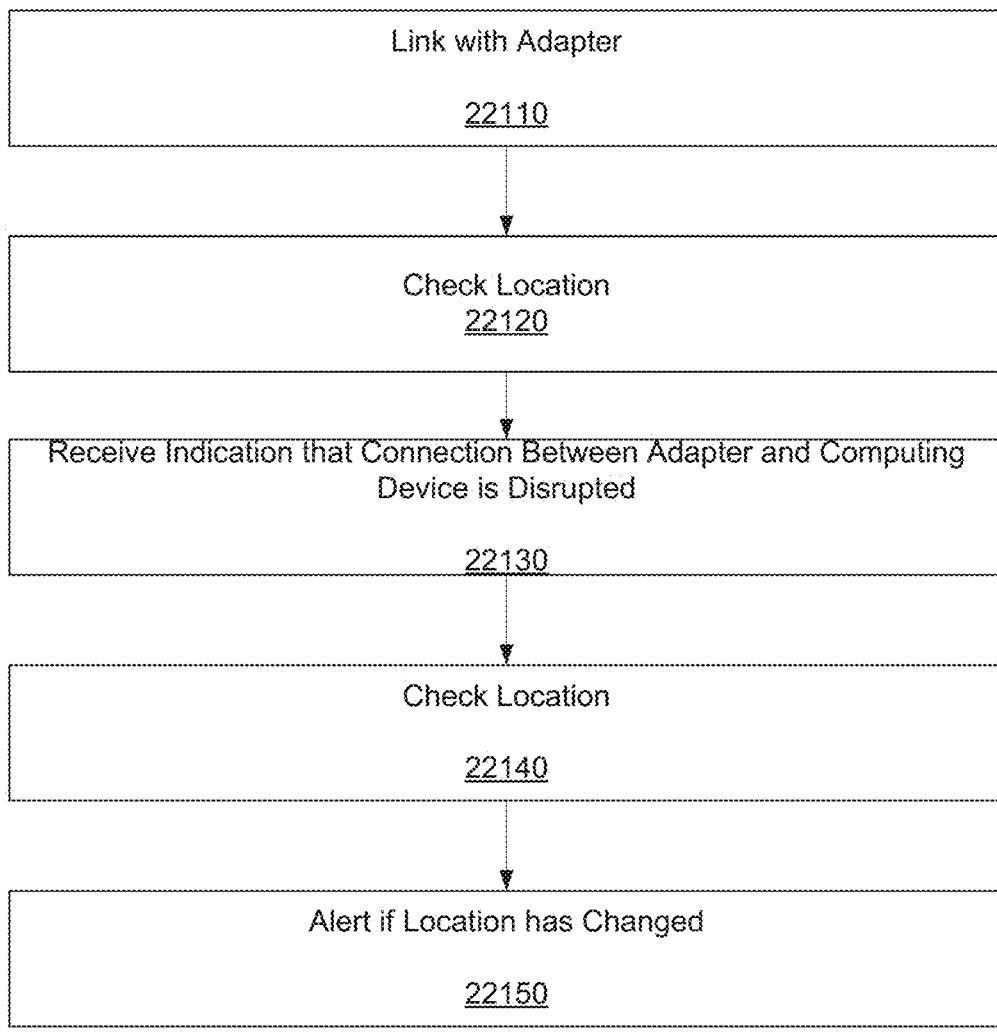

FIG. 47 is a flow chart illustrating a leash method that can be implemented by any of the leash modules shown and described herein. At 22110, a computing device (which can be similar to the computing device 1510) can establish a communication link, such as a Bluetooth® link, with an adapter (which can be similar to the adapter 1210), a medicament delivery device and/or a simulated medicament delivery device. Once a link is established, the computing device can check, record, and/or report its location (e.g., via GPS), at 22120.

The communication link can be maintained while the computing device and the adapter are within radio range. At 21130, the computing device can receive an indication at a first time that the connection has been lost. The indication can include a failure to receive an acknowledgement of a signal sent to the adapter device, the failure of the adapter device to send a data packet at an expected time, and/or any other suitable indication. In some instances, the indication of failure can be associated with radio interference, in other instances, the failure can be associated with a user carrying the computing device away from the adapter (or vice versa).

In embodiments where the adapter is coupled to or configured to be coupled to a medicament delivery device, it may be medically advisable that the medicament delivery device be available to the user at all times. If a medicament delivery device is rarely used, however, the user may have a tendency to forget to carry the medicament delivery device with him or her. The user may be much less likely to forget to carry a mobile phone (e.g., computing device). Thus if the computing device losses contact with the adapter, it may be an indication that the user has forgotten the medicament delivery device. The computing device can verify its location (e.g., via GPS), at 22140. If the location of the computing device is similar to the location received at 22120 (e.g., within a predetermined distance), this can indicate that the user is still near the adapter. Similarly, checking the location, at 22140 can include determining whether the computing device is located in a "home" region (e.g., a predetermined boundary or geographic area), which can indicate that the user is still near the adapter. The home region can be a predefined region, e.g., selected by the user. For example, the computing device can be operable to prompt or allow the user to define a home region, which can be an area where the user is likely to have access to a medicament delivery device (e.g., the user's house) and/or the computing device can be operable to infer a home region, for example, based on a common location of the computing device and/or a common location of a computing device during a particular period (e.g., the user can infer that a location of the computing device at 3:00 am is a home region).

If the location of the computing device at 22140 is different from the location at 22120 (e.g., by 300 feet, 1000 feet, ½ mile, 5 miles, and/or any other suitable distance) and/or the location of the computing device at 22150 is outside the home region, this can indicate that the medicament delivery device has been left behind, and an alert can be generated, at 22150. The alert can include an audible and/or visual alert to inform the user that connection has been lost. In addition or alternatively, the computing device can send a signal e.g., via WiFi or a cellular data network to a remote device, such that user compliance can be tracked and/or monitored.

Figure 48:
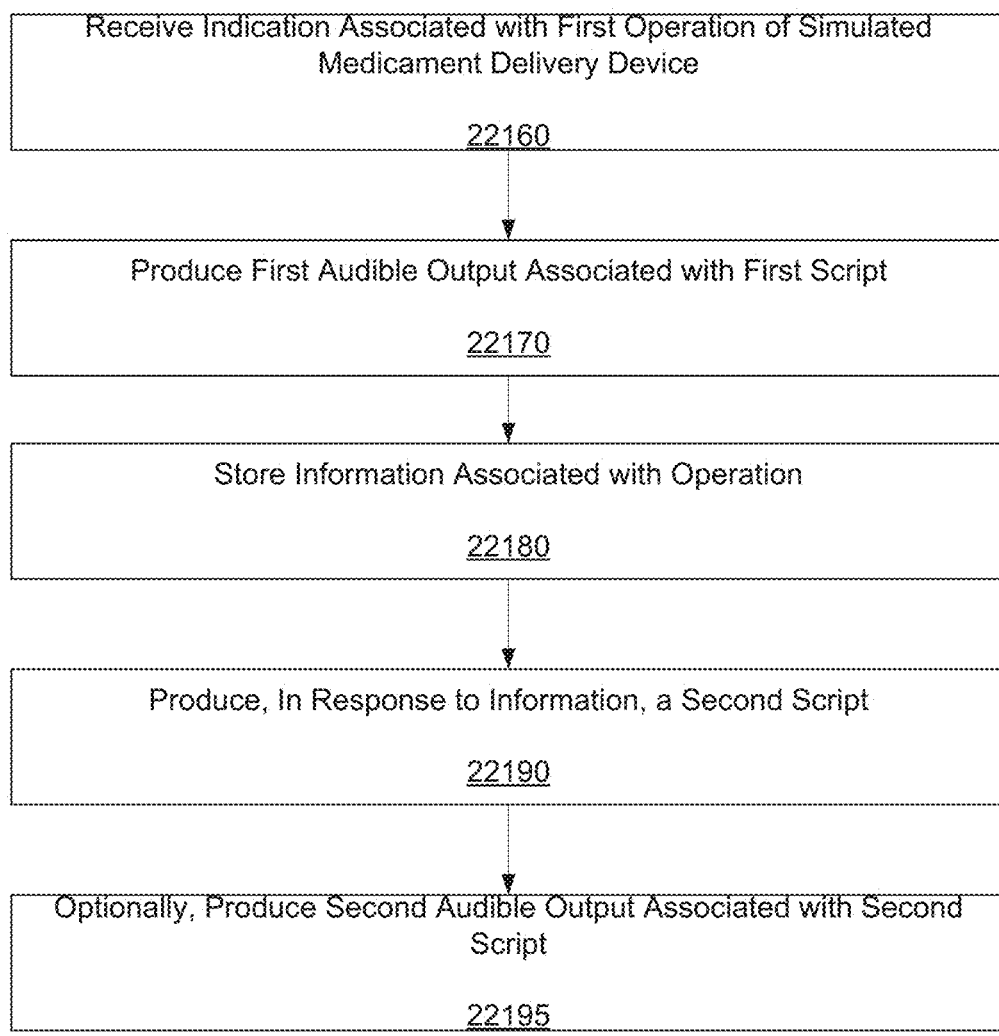
FIG. 48 is a flow chart of a method of using a simulated medicament delivery device, according to an embodiment.

FIG. 48 is a flow chart of a method of operation of a simulated medicament delivery device, according to an embodiment. A simulated medicament delivery device (also referred to herein as a "trainer") can be used to train a user on the operation of an actual medicament delivery device. A simulated delivery device can be structurally and/or functionally similar to any of the medicament delivery devices described herein, but may be devoid of a medicament a, needle, and/or components associated with delivery of the medicament. A simulated medicament delivery device can include a processor, memory, a battery, sensors and/or any other suitable components. In some embodiments a simulated medicament device can be resettable and/or reusable. A simulated medicament delivery device can be coupleable to an adapter, and/or can include any of the components of the adapters shown and described herein. For example, a simulated medicament device can include a Bluetooth® processor and can be operable to communicatively link with a computing device, as described herein.

At 22160, an indication associated with a first operation of a simulated medicament delivery device can be received. For example, a simulated medicament delivery device can include one or more sensors and/or switches operable to detect various operations, such as sensor operable to detect when a sleeve is removed, when a safety guard is removed, when an actuator is manipulated, the position of the simulated medicament delivery device, and/or any other suitable operation. The indication received, at 22160 can be any suitable operation associated with the use of a simulated medicament delivery device.

In response to receiving the indication, at 22160, a first audible output can be generated, at 22170. The audible output can be associated with a first script, and can be an acknowledgement of the operation, an instruction of a next operation, an instruction that an operation was not properly performed (e.g., operations performed out of sequence, operations performed with insufficient force, operations performed with the simulated medicament delivery device in an improper orientation, an instruction that the operation was not performed within an appropriate period of time, etc.), and so forth.

At 22180, information associated with the operation can be stored, for example in a memory (e.g., a memory coupled to the simulated medicament delivery device, a memory of an adapter, a memory in a remote database, etc.) The information stored, at 22180, can include an indication of which operation was performed, time data, orientation data, temperature data, and/or any other suitable information. The information stored, can be used to improve the training of the user. For example, the information stored can reveal a pattern of improper use. At 22190, a second script can be produced. The second script can, for example, reflect updated instructions based on errors identified from the information.

At 22195, a second audible output associated with the second script can optionally be generated. The second audible output can be based on information stored, at 22180, and/or the second operation. In this way, the second audible output can be based on patterns (e.g., the first operation and the second operation), elapsed time, and/or any other suitable characteristic. As an illustration, if the first operation and the second operation are each attempted manipulations of the actuator, the indication received at 22160, and the indication received, at 22190, are each indications that insufficient force was applied, the second script, and the second audible output, at 22195 can include an instruction that to apply additional force, as insufficient force has twice been applied.

Figure 51:
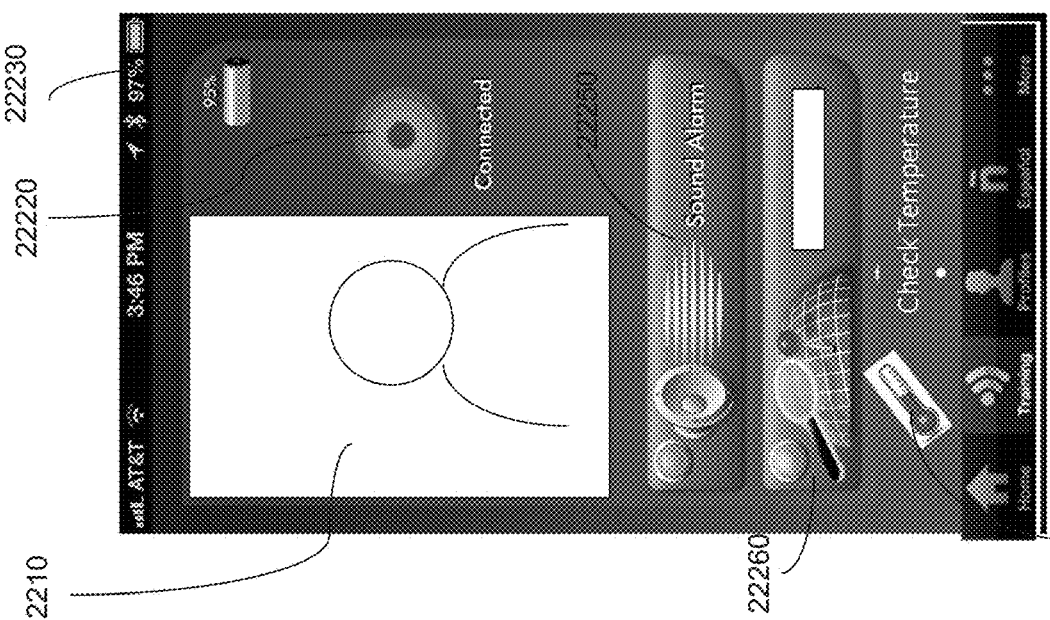
FIGS. 49-51 are screenshots of a user interface associated with methods, according to three embodiments.
Figure 50:
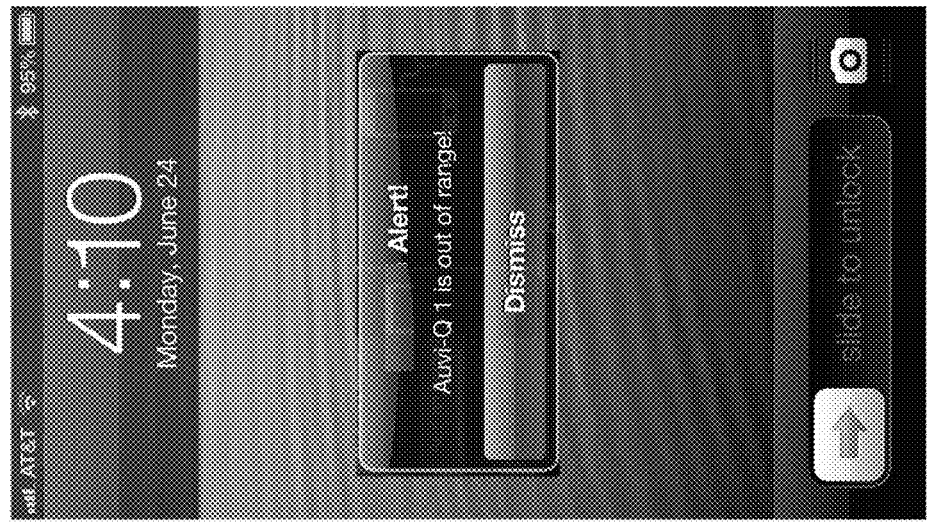
Figure 49:
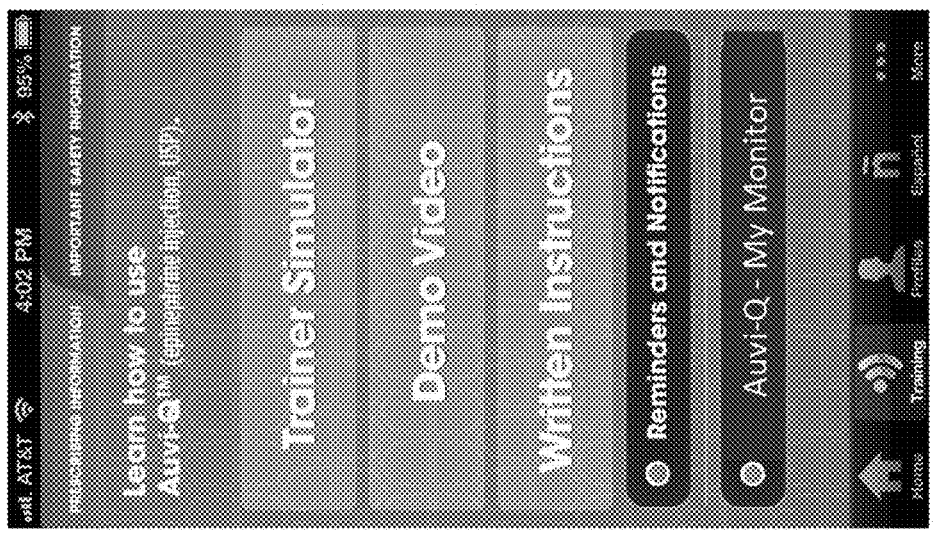

FIG. 49-51 are screenshots of instances of a user interface for an application. A processor, for example, a processor of a computing device such as a mobile phone communicatively linked to an adapter and/or medicament delivery device, can execute the application. The application can provide a user information associated with status, location, use, etc.

For example, as shown in FIG. 49, in some instances, the application can provide access to a trainer simulator, a demo video, written instructions, reminders and notifications, and/or a medicament delivery device monitor. For example, the instance of the application shown in FIG. 49 can enable a user to access a demonstration video. Such a video can aid a user in properly using a medicament delivery device. Similarly, written instructions, can provide convenient access to detailed information associated with a medicament delivery device. In some cases, owing to the size of a medicament delivery device, labeling real estate may be at a premium. An application can provide additional information, as well as interactive information, such as hyperlinks etc. The written instructions can also be updated remotely.

In addition, the application can be operable to provide reminders, for example, if the user is scheduled to use the medicament delivery device. In embodiments where the computing device is communicatively linked to the adapter, the application can receive signals from the adapter associated with use of the medicament delivery device. In this way, a reminder may only be issued if the user has not actually used the medicament delivery device according to a schedule.

The application can also generate alerts, for example if the medicament has expired, been recalled, or if the medicament delivery device has experienced a temperature unsuitable for the medicament. Any suitable methods for tracking the temperature history of the medicament delivery device can be employed, such as, for example, those methods disclosed in U.S. Pat. No. 8,361,029, entitled "Devices, Systems and Methods for Medicament Delivery" issued Jan. 29, 2013, the disclosure of which is incorporated herein by reference in its entirety. Similarly stated, a computing device can receive signals associated with the status of the medicament delivery device from the medicament delivery device and/or from a remote computing device and the application can notify the user of the status.

In some embodiments, the application can notify the user if the medicament delivery device is out of range, for example, generating an alert as shown in FIG. 50. As shown and described above with reference to FIG. 47, a lost communication link can be indicative that a user has forgotten to carry the medicament delivery device. Similarly stated, in some embodiments a computing device, such as a mobile phone, can execute the method (e.g., at a processor) shown and described with reference to FIG. 47. In such an embodiment, an application can alert the user of the lost communication link.

FIG. 51 depicts an instance of an application operable to monitor a medicament delivery device. The application can be personalized, as represented by a depiction of an avatar 22210 or photo of the user. The application can indicate a connection status 22220, for example indicating the presence and/or strength of a communication link. The application can also display, for example based on information received from an adapter, information associated with the charge state 22230 of a battery associated with the adapter and/or medicament delivery device and/or the current temperature 22240 of the medicament delivery device and/or temperature history of the medicament delivery device (which may be relevant to medicament stability). Furthermore, the application can enable the user to send a signal to the adapter to cause the adapter to emit a sound 22250, which may aid the user in locating the medicament delivery device and/or can cause the computing device to use radio-location techniques to aid the user in locating the adapter 22260.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although electronic circuit systems are shown and described above as outputting one or more outputs directed towards a single, immediate user, in some embodiments, a locator device and/or monitoring device can output multiple outputs directed towards multiple different classes of users. For example, in some embodiments, the locator device and/or monitoring device can output a first output to the immediate user and second output to a remotely located emergency response team. In such embodiments, the second output can be, for example, a phone call, SMS, a page, an e-mail or the like. For example, in some embodiments, the second output can be an e-mail to the parents and/or care-givers of a child. Moreover, such a second output can be transmitted either wirelessly or through a wired network.

Although the electronic circuit systems are shown and described above as outputting one or more outputs in response to one or more switches, in other embodiments an electronic circuit system can output an electronic output in response to any number of different inputs. For example, in some embodiments, an electronic circuit system can output an electronic output based on input from the user provided via a keyboard, a touch screen, a microphone or any other suitable input device. In this manner, the electronic outputs can be produced in response to direct feedback from the user.

The adapters, medicament delivery devices and simulated medicament delivery devices are described herein as being configured to produce one or more wireless signals in accordance with the methods described herein. Although the methods and apparatus are described herein as being configured to modify the communication mode and/or the communication interval associated with such wireless signals in response to a change in the status and/or configuration of a device (e.g., a medicament delivery device or a simulated medicament delivery device), in other embodiments, any of the apparatus and methods described herein can modify any aspect of the wireless signals based on such change in status and/or configuration. For example, in some embodiments a method can include modifying a power level of a wireless signal in response to a change in status and/or configuration of a medicament delivery device or a simulated medicament delivery device. In other embodiments, a method can include modifying the information contained within a wireless signal in response to a change in status and/or configuration of a medicament delivery device or a simulated medicament delivery device. For example, in some embodiments, a wireless signal can include information associated with a signal power level (e.g., TX Power) and/or an identification of a device. Such information can be changed in response to a change in status and/or configuration of a medicament delivery device or a simulated medicament delivery device.

In some embodiments, information included within a signal can include instructions to initiate a natural language user interface associated with (or running on) another device. Thus, any of the apparatus and methods described herein can be configured to send and/or can include the sending of a signal to initiate a natural language user interface associated with a remote computing device. For example, in some embodiments, the adapter 120 can be configured to send a wireless signal to initiate a natural language user interface associated with the monitor device 150. In such embodiments, the monitor device 150 can be, for example, a smart phone having a natural language user interface, such as, for example, Ski (from Apple) or any other "intelligent personal assistant." The adapter can be configured to initiate the user interface via the wireless connection by sending a signal. In some embodiments, the signal can be sent in response to a change in the status and/or configuration of the medicament delivery device and/or the simulated medicament delivery device. In this manner, the adapter 120 can initiate the interface to provide the user with additional resources during a time of activity with the medicament delivery device and/or the simulated medicament delivery device. Moreover, in such embodiments, the adapter 120 can also be configured to relay input to the user interface via the wireless connection between the adapter 120 and the monitor device 150. For example, in some embodiments, a user can input information via a microphone on the adapter 120 to send information to the user interface of the monitor device 150.

In some embodiments, a computing device can send signals based on and/or produced from a natural language interface that are received by a medicament delivery device, an adapter and/or a simulator of the types shown and described herein. For example, a system can include a computing device, such as a cell phone that has a natural language interface, and a medicament delivery device, such as a patch pump. In such embodiments, a user can provide voice commands to natural language interface of the cell phone. Such commands can include, for example, instructions to administer an additional dose, instructions to call a health-care professional or the like. In response, the cell phone can send, via a wireless connection of the types shown and described herein, a signal to the medicament delivery device. The device can then execute the instructions. In this manner, the capability of the cell phone can be leveraged to produce a voice-activated medicament delivery device.

Although the embodiments of FIGS. 40-42 are shown and described as receiving a signal from an access control device 310, in other embodiments, a user could enter a password PIN or other personally identifiable information to the kit 300 via a keyboard, touch screen, voice command and/or any other suitable device.

Although the kit 300 of FIGS. 40-42 is shown and described as containing a removable medicament container 360, in other embodiments, the kit 300 can dispense a medicament directly, and/or can dispense a medicament delivery device.

Although the adapters 120 and 14240 are shown and described above a receiving at least a portion of a medicament delivery device (or simulated medicament delivery device), any of the adapters described herein can be coupled to a medicament delivery device (or simulated medicament delivery device) in any suitable manner. For example, in some embodiments, any of the adapters described herein can be coupled to a medicament delivery device (or simulated device) via only one side (i.e., the adapter does not "receive" a portion of the device). For example, in other embodiments, any of the adapters described herein can be similar to the container shown and described with respect to the kit 300. In yet other embodiments, the adapter can be a wall-mounted box within which multiple medicament delivery devices, medicament containers and/or simulated medicament delivery devices can be stored.

Some embodiments described above include an adapter (or medicament delivery device) and a locator device operable to communicate with each other and/or locate each other. The monitoring device and/or the locator device can communicate via Bluetooth®, WiFi, a cellular telephone network, a satellite pager network, localized AM or FM radio signals, Broadcast AM, FM, or satellite radio, RFID signals, human audible or inaudible sound waves, IR, Zigbee™, X10, and/or any other suitable signal. In some embodiments, the monitoring device and/or the locator device can be operable to locate any other device via, audible, visual, radio, GPS, and/or any other suitable location technique. The monitoring device and or the locator device can aid a user in locating a medicament delivery device by, for example, causing the medicament delivery device and/or the locator device to emit a audible, visual, and/or tactile alert. The alert can vary in power, frequency, and/or any other suitable parameter as the monitoring device and/or the locator device are brought closer to the medicament delivery device.

Any of the radios, transmitters, receivers, and/or transceivers described herein can be operable to transmit, receive, repeat, and/or otherwise interact with electromagnetic signals. Electromagnetic signals can be of any suitable frequency. For example, the radios, transmitters, receivers, and transceivers can be operable to transmit and/or receive IEEE 802.11 signals, Bluetooth® signals, FM radio signals, AM radio signals, cellular telephone signals, satellite pager signals, RFID signals, GPS signals, and/or any other suitable electromagnetic signal.

Although some of the embodiments described herein include one "master device" (e.g., the monitoring device 150, which can be, for example, a smart phone) and one "slave device" (e.g., the adapter 120), in other embodiments, devices and methods can include and/or establish a piconet including any suitable number of master devices and/or slave devices. For example, in some embodiments, a monitor device 150 can be configured to establish a piconet with more than one adapter 120. In other embodiments, a monitor device can be configured to establish a piconet with an adapter 120 configured to receive a first medicament delivery device, a simulated medicament delivery device (or trainer) associated with the first medicament delivery device (e.g., a wireless-enabled trainer of the types shown and described herein) and a second medicament delivery device (e.g., a wireless-enabled medicament delivery device).

In some embodiments, a medicament delivery device is shown and described as an auto-injector. In other embodiments, the medicament delivery device can be a patch configured to adhere to the patient. The patch can release a medicament, for example, after receiving a signal that medical treatment is needed. The patch can receive the signal from, for example, a monitoring device. In other embodiments, the medicament delivery device can be an injector configured to be carried in a pocket of the patient's garments. The injector can be configured to inject a medicament, for example, after receiving a signal that medical treatment is needed.

In some embodiments, a locator device and/or a medicament delivery device can include an electronic circuit system and/or a sensor and be operable to output an electronic output. Such a sensor can include, for example, a proximity sensor (e.g., to determine the position of the medicament delivery device), a temperature sensor, a pressure sensor, an optical sensor or the like. For example, in some embodiments, the container can include a temperature sensor configured to sense the temperature of the medicament contained within the medicament delivery device. In this manner, the electronic circuit system can output an instruction and/or a status message when the medicament is too cold for effective delivery. For example, in some embodiments, when the medicament is too cold for effective delivery or the delivery of a cold medicament may cause unnecessary pain and discomfort (this may occur, for example, if the container is being used in an outdoor setting or requires refrigeration prior to use), the electronic circuit system can output a message, such as, for example, "Medicament is too cold—allow medicament to reach room temperature before using" and can alert the user when the proper temperature has been reached.

Although in some embodiments the electronic circuit systems are shown and described above as outputting a single output in response to an input (e.g., the removal of a medicament delivery device, the change in position of a hinged lid, etc.), in other embodiments, an electronic circuit system can output a sequence of electronic outputs in response to such an input. In some embodiments, for example, when a medicament delivery device is removed from a container, an electronic circuit system can output a predetermined sequence of use instructions over a predetermined time period. For example, upon removing the medicament delivery device, the first instruction can be an audible output indicating the type of medicament delivery device removed. After a predetermined time period, the electronic circuit system can then output a second instruction, which can be a visual output instructing the user in how to diagnose the patient and/or prepare the patient for the medicament. In a similar manner, the electronic circuit system can provide additional outputs to instruct the user in the use of the medicament delivery device. Moreover, in some embodiments, the electronic circuit system can output an output instructing the user in post-use procedures, such as for example, the disposal of the medicament delivery device, instructions for follow-up treatment or the like.

For example, although the electronic circuit systems are shown and described above as being configured to output primarily audible and visual outputs, in other embodiments, an electronic circuit system can be configured to produce any suitable output. For example, in some embodiments, an electronic circuit system can produce a haptic output, such as a vibratory output produced by a piezo-electric actuator. In other embodiments, an electronic circuit system can produce a thermal output, produced by a heating or cooling element.

Although some embodiments describe a recorded message output in English, in other embodiments, the electronic circuit system can output recorded speech in any language. In yet other embodiments, the electronic circuit system can output recorded speech in multiple languages. In yet other embodiments, the user can select the language in which the recorded speech is to be output.

Medicament delivery devices shown and described above can be single-use medical injectors, or any other suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system can output instructions associated with not only an initial use of the medicament delivery device, but also associated with repeated uses, dosage monitoring or the like. In other embodiments, a medicament delivery device can include a transdermal medicament delivery device, a wearable injector or pump that dispenses drug over several hours or days, an inhaler or a nasal medicament delivery device.

Any of the monitoring devices, adapters and/or locators described herein can be configured to send a signal in response to the detection of a potential emergency. For example, in some embodiments any of the devices described herein can be GPS-enabled, and can automatically dial an emergency number such as, for example, 911 (emergency dispatcher), and/or send information associated with the location of the device and/or the end user location through GPS satellite positioning or network based positioning (using cell phone towers).

Although various embodiments have been described as having particular features and/or combinations of components, other embodiments are possible having a combination of any features and/or components from any of embodiments where appropriate. For example, in some embodiments a kit can include an electronic circuit system, two or more medicament delivery devices and a movable portion. In such embodiments, each of the medicament delivery devices can be associated with a switch. Moreover, the movable portion can also be associated with a switch. In this manner, the electronic circuit system can be configured to output a first electronic output when the movable portion is moved, a second electronic output when the first medicament delivery device is removed from the container and a third electronic output when the second medicament delivery device is removed from the container.

As another example, although some embodiments are described as having a processor, a radio, a sensor, etc. disposed on an adapter and/or a cover, devices, structures, and/or modules associated with adapters and/or covers can be disposed on any suitable device. For example, in some embodiments, a housing of a medicament delivery device or simulated medicament delivery device can include a processor and/or radio. Similarly, some embodiments describe a kit having a processor, audible output, etc. Any devices, structures, and/or modules associated with a kit, however, can be associated with an adapter, cover, medicament delivery device, and/or simulated medicament delivery device.

The medicament delivery devices described herein, such as the medicament delivery device 100, the medicament delivery device 21990 and any others described herein, can be any suitable medicament delivery device. For example, a medicament delivery device according to an embodiment can include a pen injector, an auto-injector, a wearable injector or pump that dispenses drug over several hours or days, an inhaler or a transdermal delivery device. Where medicament delivery devices are described, it should be understood that alternative embodiments including a simulated medicament delivery device are possible, for example, the simulated medicament delivery devices shown and described in U.S. patent application Ser. No. 11/679,331 (and Patent Publication No. 2008/0059133), entitled "Medical Injector Simulation Device" filed Feb. 27, 2007, the disclosure of which is incorporated herein by reference in its entirety. A simulated medicament delivery device may be suitable to train a user in the operation of a medicament device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

In some embodiments the medicament delivery devices and/or medicament containers shown herein can include any suitable medicament, such as a vaccine. Such vaccines can include, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a cancer vaccine, a smallpox vaccine, a pneumococcal vaccine, a rotavirus vaccine, a varicella vaccine, a meningococcus vaccine and/or any combination thereof (e.g. tetanus, diphtheria and pertussis vaccine). In other embodiments, the medicament delivery devices and/or medicament containers shown herein can include epinephrine. In other embodiments, the medicament contained within any of the medicament delivery devices and/or medicament containers shown herein can be naloxone, including any of the naloxone formulations described in U.S. Pat. No. 8,627,816, entitled "Medicament Delivery Device for Administration of Opioid Antagonists Including Formulation for Naloxone," filed on Feb. 28, 2011.

In other embodiments, the medicament contained within any of the medicament delivery devices and/or medicament containers shown herein can include insulin, glucagon, human growth hormone (HGH), erythropoiesis-stimulating agents, adalimumab, other monoclonal Antibodies (mAbs'), Interferon and other chronic therapies, or the like. Such formulations can be produced using a general lyophilization process with glucagon (of recombinant or synthetic origin) using bulking agents, stabilizers, buffers, acidifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments any of the medicament delivery devices and/or medicament containers described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary andioedema, and other auto-immune diseases. In yet other embodiments, any of the medicament delivery devices and/or medicament containers described herein can be filled with and/or used to inject intranasal medicaments including small molecules such as epinephrine, naloxone, diazepam, midazolam, lorazepam or biologics, such as glucagon or human growth hormone, formulated for use in an auto injector, for the treatment of musculoskeletal diseases, growth disorders, diabetes or other disorders. Thus, although the medicament delivery devices shown herein are primarily injectors, in other embodiments, a medicament delivery device need not be a medical injector, but rather, can be an inhaler, a wearable pump, an intranasal delivery device or the like.

In other embodiments, any of the medicament delivery devices and/or medicament containers described herein can be filled with and/or used to inject an anti-thrombolytic, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the medicament delivery devices and/or medicament containers described herein can be filled with and/or used to inject recombinant hyaluronidase.

In other embodiments, any of the medicament delivery devices and/or medicament containers described herein can be filled with and/or used to inject depot medroxyprogesterone acetate for the treatment of infertility.

In other embodiments, any of the injectors described herein can be filled with and/or used to inject Benzodiazepines such as Midazolam, Anticoagulants, Hematopoietic agents, Adrenocortical steroids, Antidiabetic agents, Sex hormones, Somatostatin Analogs, Monoclonal Antibodies, Agents for Migraine, Antianxiety Agents, Antiemetic/Antivertigo Agents, Antipsychotic Agents, General Anesthetics, NSAIDs, Opioid Agonist-Antagonist, Opioid Analgesics, Skeletal Muscle Relaxants. Aminoglycosides, Antiprotozoals, Antiretroviral Agents, Antituberculosis Agents, Bacitracin, Cephalosporin and Related Antibiotics, Colistimethate sodium, Lincosamides, Monobactams, Penicillins, Polymyxin B Sulfate, Antirheumatologic Agents, Antimetabolites, Immune Globulins, Immulogic Agents, Monoclonal antibodies, Antimetabolites, Hematopoietic, and/or Hemin, and agents that block proprotein convertase subtilisin/kexin type 9 (PCSK9).

In other embodiments, any of the medicament delivery devices and/or medicament containers described herein can be filled with and/or used to inject environmental, food, and household allergen formulations for the treatment of allergic disease, specifically for use in immunotherapy.

In still other embodiments, the medicament contained within any of the medicament delivery devices and/or medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include a "configuration switch" (similar to any of the switches shown and described above, such as the switch 6972) that, when actuated during the assembly of the delivery device, can select an electronic output corresponding to the dose contained within the medicament container. In addition, in the case of multiple-dose delivery, the user can activate via physical movement, voice command or the like a switch located on the medicament delivery device in order to select the specific dose required.

What is claimed is:

1. An apparatus, comprising:
   a medicament delivery device; and
   an electronic circuit system including a processor, a power source, a radio, an audible output device, and a power module, the radio configured to transmit a short-range wireless signal to be received by a computing device, the audible output device configured to produce an audible output when the medicament delivery device is transitioned from a first configuration to a second configuration, the power module implemented in at least one of a memory or the processor, the power module configured to suppress transmission of the short-range wireless signal to conserve power of the power source.

2. The apparatus of claim 1, wherein the power module is configured to suppress transmission of the short-range wireless signal while allowing production of the audible output from the audible output device.

3. The apparatus of claim 1, wherein the power module is configured to suppress transmission of the short-range wireless signal when the audible output device is producing the audible output.

4. The apparatus of claim 1, wherein:
   the radio is configured to send the short-range wireless signal when the medicament delivery device is in the first configuration;
   the electronic circuit system includes a sensor configured to produce a transition signal when the medicament delivery device transitions from the first configuration to the second configuration, the audible output device configured to produce the audible output in response to the transition signal; and
   the power module is configured to suppress transmission of the short-range wireless signal during a time period when the audible output is being produced.

5. The apparatus of claim 4, wherein the sensor is at least one of a contact sensor, a switch, a microphone, a capacitance sensor or an optical sensor.

6. The apparatus of claim 1, wherein:
   the medicament delivery device is an auto-injector having an actuator configured to initiate delivery of a medicament and a lock member configured to limit movement of the actuator, the lock member in a first position relative to the actuator when the auto-injector is in the first configuration, the lock member in a second position relative to the actuator when the auto-injector is in the second configuration.

7. The apparatus of claim 1, further comprising:
   an adapter configured to receive at least a portion the medicament delivery device, the portion of the medicament delivery device being within the adapter when the medicament delivery device is in the first configuration, the portion of the medicament delivery device being outside of the adapter when the medicament delivery device is in the second configuration, the power source being electrically coupled to the radio when the medicament delivery device is in the first configuration and the second configuration.

8. The apparatus of claim 1, wherein the power source is a battery continuously providing power to the processor when the medicament delivery device is in each of the first configuration and the second configuration.

9. An apparatus, comprising:
   a medicament delivery device; and
   an electronic circuit system including a processor, a power source, a radio, a light output device, an audible output device, and a power module, the radio configured to transmit a short-range wireless signal to be received by a computing device, at least one of the light output device or the audible output device configured to produce an output when the medicament delivery device is transitioned from a first configuration to a second configuration, the power module implemented in at least one of a memory or the processor, the power module configured to suppress transmission of the short-range wireless signal to conserve power of the power source.

10. The apparatus of claim 9, wherein the medicament delivery device includes a housing, the apparatus further comprising:
    an adapter configured to receive at least a portion the housing, the portion of the housing being within the adapter when the medicament delivery device is in the first configuration, the portion of the housing being outside of the adapter when the medicament delivery device is in the second configuration, the power source being electrically coupled to the radio when the medicament delivery device is in the first configuration and the second configuration.

11. The apparatus of claim 10, wherein the electronic circuit system is coupled to either the housing or the adapter.

12. The apparatus of claim 9, wherein:
    the radio is configured to send the short-range wireless signal when the medicament delivery device is in the first configuration;
    the electronic circuit system includes a sensor configured to produce a transition signal when the medicament delivery device transitions from the first configuration to the second configuration, the audible output device configured to produce an audible output in response to the transition signal; and
    the power module is configured to suppress transmission of the short-range wireless signal during a time period when the audible output is being produced.

13. The apparatus of claim 9, wherein the power source is a battery continuously providing power to the processor when the medicament delivery device is in each of the first configuration and the second configuration.

14. A non-transitory processor-readable medium storing code representing instructions to be executed by a processor, the code comprising code to cause the processor to:

produce a first wireless signal characterized by a first communication interval when a medicament delivery device is in a first configuration;

receive an indication associated with the medicament delivery device being transitioned from the first configuration to a second configuration; and produce a second wireless signal characterized by a second communication interval in response to the indication, the second communication interval different from the first communication interval.

15. The non-transitory processor-readable medium of claim 14, wherein the first wireless signal and the second wireless signal are each produced in accordance with a wireless protocol to establish electronic communication with a computing device.

16. The non-transitory processor-readable medium of claim 14, wherein at least one of the first wireless signal or the second wireless signal includes information associated with a signal power level and an identification of the medicament delivery device.

17. The non-transitory processor-readable medium of claim 14, wherein:

the first communication interval is associated with a first communication mode between an electronic circuit system and a computing device; and the second communication interval is associated with a second communication mode between the electronic circuit system and the computing device, the second communication mode different than the first communication mode.

18. The non-transitory processor-readable medium of claim 14, wherein the indication is a first indication, at least one of the first wireless signal or the second wireless signal is associated with a first radio frequency channel, the code further comprising code to cause the processor to:

receive a second indication associated with the medicament delivery device being transitioned from the second configuration to a third configuration; and produce, in response to the second indication, a third wireless signal associated with a second radio frequency channel, the second radio frequency channel different from the first radio frequency channel.

19. The non-transitory processor-readable medium of claim 18, wherein:

the first radio frequency channel is an advertising channel associated with a wireless protocol; and the second radio frequency channel is a data channel associated with the wireless protocol.

20. The non-transitory processor-readable medium of claim 14, wherein the second wireless signal includes information associated with a strength of the second wireless signal and an identification of the medicament delivery device.

\* \* \* \* \*